(12) United States Patent
Combette et al.

(10) Patent No.: US 10,967,038 B2
(45) Date of Patent: Apr. 6, 2021

(54) USE OF CELL-PERMEABLE PEPTIDE INHIBITORS OF THE JNK SIGNAL TRANSDUCTION PATHWAY FOR THE TREATMENT OF CHRONIC OR NON-CHRONIC INFLAMMATORY EYE DISEASES

(71) Applicant: Xigen Inflammation Ltd., Limassol (CY)

(72) Inventors: Jean-Marc Combette, Saint-Cergues (FR); Catherine Deloche, Geneva (CH); Claire Abadie, Annecy (FR)

(73) Assignee: Xigen Inflammation Ltd., Limassol (CY)

(*) Notice: Subject to any disclaimer, the term of this patent is extended or adjusted under 35 U.S.C. 154(b) by 0 days.

(21) Appl. No.: 15/934,735

(22) Filed: Mar. 23, 2018

(65) Prior Publication Data

US 2019/0060392 A1 Feb. 28, 2019

Related U.S. Application Data

(60) Continuation of application No. 14/849,374, filed on Sep. 9, 2015, now abandoned, which is a division of application No. 13/879,059, filed as application No. PCT/EP2010/006284 on Oct. 14, 2010, now Pat. No. 9,150,618.

(51) Int. Cl.
*A61K 38/00* (2006.01)
*C07K 14/00* (2006.01)
*A61K 38/17* (2006.01)

(52) U.S. Cl.
CPC ........ *A61K 38/005* (2013.01); *A61K 38/1709* (2013.01); *C07K 14/001* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,595,756 A | 1/1997 | Bally et al. | |
| 6,620,914 B1 | 9/2003 | Waeber et al. | |
| 7,033,597 B2 | 4/2006 | Bonny | |
| 7,538,091 B2 | 5/2009 | Bonny | |
| 7,803,749 B2 | 9/2010 | Bonny | |
| 8,063,012 B2 | 11/2011 | Watt et al. | |
| 8,080,517 B2 | 12/2011 | Bonny | |
| 8,183,339 B1 | 5/2012 | Bonny | |
| 8,569,447 B2 | 10/2013 | Bonny | |
| 8,748,395 B2 | 6/2014 | Bonny | |
| 8,981,052 B2 | 3/2015 | Bonny | |
| 9,006,185 B2 | 4/2015 | Bonny | |
| 9,150,618 B2 * | 10/2015 | Combette | A61K 38/005 |
| 9,180,159 B2 | 11/2015 | Bonny | |
| 9,290,538 B2 | 3/2016 | Bonny | |
| 9,610,330 B2 | 4/2017 | Bonny | |
| 9,624,267 B2 | 4/2017 | Bonny | |
| 2002/0090696 A1 | 7/2002 | Miller et al. | |
| 2005/0019366 A1 | 1/2005 | Zeldis | |
| 2005/0043241 A1 | 2/2005 | Bonny | |
| 2006/0166881 A1 | 7/2006 | Hotchkiss et al. | |
| 2006/0178310 A1 | 8/2006 | Bonny | |
| 2007/0060514 A1 * | 3/2007 | Bonny | C07K 7/06 514/1.2 |
| 2008/0051410 A1 | 2/2008 | Watterson et al. | |
| 2008/0274956 A1 | 11/2008 | Bonny et al. | |
| 2009/0281036 A1 | 11/2009 | Meyer | |
| 2009/0305968 A1 | 12/2009 | Bonny | |
| 2010/0098635 A1 | 4/2010 | Lamping et al. | |
| 2010/0216716 A1 | 8/2010 | Bonny | |
| 2010/0256041 A1 | 10/2010 | Bonny et al. | |
| 2010/0331335 A1 | 12/2010 | Sham et al. | |
| 2011/0052566 A1 | 3/2011 | Rosenblum et al. | |
| 2011/0183688 A1 | 7/2011 | Bonny | |

(Continued)

FOREIGN PATENT DOCUMENTS

| CA | 2738951 A1 | 7/2010 |
|---|---|---|
| CN | 101263157 A | 9/2008 |

(Continued)

OTHER PUBLICATIONS

NIH, "Panuveitis", https://rarediseases.info.nih.gov/diseases/8577/panuveitis;2016, pp. 1-7 (Year: 2016).*
Garg, "Successful Management of Uveitis in a Patient With Unilateral Multifocal Choroiditis", Insert to Retina Today, 2019, pp. 1-8 (Year: 2019).*
Hollos et al., "JNK Regulation of Depression and Anxiety", Brain Plasticity, 2017/2018, pp. 145-155 (Year: 2017).*
Fung et al., "Multifocal Choroiditis Without Panuveitis", Retina, The Journal of Retinal and Vitreous Disease, 2014, pp. (Year: 2014).*
Essex et al.,"Idiopathic Multifocal Choroiditi: A Comment on Present and Past Nomenclature", Retina, The Journal of Retinal and Vitreous Disease, 2013, pp. 1-4 (Year: 2013).*

(Continued)

*Primary Examiner* — Lianko G Garyu
(74) *Attorney, Agent, or Firm* — Harness Dickey & Pierce P.L.C.

(57) ABSTRACT

The present invention refers to the use of protein kinase inhibitors and more specifically to the use of inhibitors of the protein kinase c-Jun amino terminal kinase, JNK inhibitor (poly-)peptides, chimeric peptides, or of nucleic acids encoding same as well as pharmaceutical compositions containing same, for the treatment of non-chronic or chronic inflammatory eye diseases, such as inflammatory diseases of the blephara, conjunctiva, cornea, sclera, the vitreous body, uvea, ciliary body, choroid, orbital bone, lacrimal gland, or iris, in particular wherein the inflammatory disease is selected from hordeolum, chalazion, conjunktivitis, keratitis, scieritis, episcleritis, endophthalmitis, panophtalmitis, irititis, uveitis, cyclitis, chorioiditis, orbital phlegmon, and myositis of the eye muscle etc.

2 Claims, 21 Drawing Sheets
Specification includes a Sequence Listing.

(56) References Cited

U.S. PATENT DOCUMENTS

| | | |
|---|---|---|
| 2012/0058137 A1 | 3/2012 | Bonny |
| 2012/0071483 A1 | 3/2012 | Cohen et al. |
| 2012/0142584 A1 | 6/2012 | Bonny |
| 2012/0148590 A1 | 6/2012 | Bonny |
| 2012/0328609 A1 | 12/2012 | Lewcock et al. |
| 2014/0057834 A1 | 2/2014 | Bonny |
| 2014/0309400 A1 | 10/2014 | Combette et al. |
| 2015/0133393 A1 | 5/2015 | Combette et al. |
| 2016/0089413 A1 | 3/2016 | Combette et al. |
| 2016/0115200 A1 | 4/2016 | Combette et al. |
| 2016/0199444 A1 | 7/2016 | Combette et al. |
| 2016/0264630 A1 | 9/2016 | Bonny |
| 2017/0056466 A1 | 3/2017 | Combette et al. |
| 2017/0128516 A1 | 5/2017 | Combette et al. |
| 2017/0137481 A1 | 5/2017 | Combette et al. |
| 2017/0290877 A1 | 10/2017 | Combette et al. |
| 2017/0320917 A1 | 11/2017 | Bonny |
| 2018/0170983 A1 | 6/2018 | Cornbette et al. |
| 2019/0060392 A1 | 2/2019 | Combette et al. |

FOREIGN PATENT DOCUMENTS

| | | | |
|---|---|---|---|
| CN | 1736901 B | 5/2010 | |
| EP | 84691 A1 | 8/1983 | |
| EP | 2627346 A1 | 8/2013 | |
| FR | 2767323 A1 | 2/1999 | |
| JP | 2002534479 A | 10/2002 | |
| JP | 2003511071 A | 3/2003 | |
| JP | 2003531871 A | 10/2003 | |
| JP | 2004-66595 A | 3/2004 | |
| JP | 2004-516811 A | 6/2004 | |
| JP | 2005512259 A | 4/2005 | |
| JP | 2005-525096 A | 8/2005 | |
| JP | 2006-501165 A | 1/2006 | |
| JP | 2006-502719 A | 1/2006 | |
| JP | 2006-512143 A | 4/2006 | |
| JP | 2006516546 A | 7/2006 | |
| JP | 2007-503617 A | 2/2007 | |
| JP | 2008-519785 A | 6/2008 | |
| JP | 2011-524861 A | 9/2011 | |
| JP | 2012-513427 A | 6/2012 | |
| JP | 5485265 B2 | 5/2014 | |
| JP | 2015502372 A | 1/2015 | |
| JP | 5711666 B2 | 5/2015 | |
| JP | 2015/197193 A | 11/2015 | |
| JP | 5824085 B2 | 11/2015 | |
| WO | 2001/043774 A1 | 6/2001 | |
| WO | 2001/098324 A1 | 12/2001 | |
| WO | 2004026406 A1 | 4/2004 | |
| WO | 2010072405 A1 | 7/2010 | |
| WO | 2010072406 A1 | 7/2010 | |
| WO | 2010091310 A1 | 8/2010 | |
| WO | WO-2010113753 A1 * | 10/2010 | .............. A61P 27/02 |
| WO | 2011/082328 A1 | 7/2011 | |
| WO | 2014/206564 A1 | 12/2014 | |
| WO | 2015197193 A3 | 2/2016 | |

OTHER PUBLICATIONS

Adhikary et al., "C-Jun NH2 terminal kinase (JNK) is an essential mediator of Toll-like receptor 2-induced corneal inflammation", Journal of Leukocyte Biology, 2008, pp. 991-997 (Year: 2008).*
Simó-Servat et al. Usefulness of the Vitreous Fluid Analysis in the Translational Research of Diabetic Retinopathy, Mediators of Inflammation, vol. 2012, Article ID 872978, 11 pages (Year: 2012).*
Bonny et al., "Cell-Permeable Peptide Inhibitors of JNK: Novel Blockers of beta-Cell Death", Diabetes, 2001, pp. 78-82 (Year: 2001).*
U.S. Appl. No. 14/891,067, filed Nov. 13, 2015.
U.S. Appl. No. 15/516,943, filed Apr. 5, 2017.
U.S. Appl. No. 15/217,326, filed Jul. 22, 2016.
U.S. Appl. No. 16/222,387, filed Dec. 17, 2018.
U.S. Appl. No. 16/430,697, filed Jun. 4, 2019.
U.S. Appl. No. 16/525,234, filed Jul. 29, 2019.
Chen et al., "The Role of c-Jun N-terminal Kinase (JNK) in Apoptosis induced by Ultraviolet C and gamma Radiation," J. of Bio. Chem., 271(50):31929-31936 (1996).
133:204452, Interaction of native RNAs with Tat peptides. Chemical Abstracs Database Sep. 29, 2000:1-3.
GenBank Database Accession No. AAD20443. islet-brain 1 [Homo sapiens]. GenBank Mar. 17, 1999: 1-2.
GenBank Database Accession No. AAD22543. islet-brain 1 (Rattus riorvegicus]. GenBank Mar. 1, 2006: 1-2.
GenBank Database Accession No. AF074091. Homo sapiens islet-brain 1 mRNA, complete cds. GenBank Mar. 17, 1999: 1-2.
GenBank Database Accession No. AF108959. Rattus norvegicus islet-brain 1 (IBI) rnRNA, complete cds. GenBank Mar. 1, 2006: 1-3.
GenBank Database Accession No. AF218778. Homo sapiens islet-brain 2 mRNA, complete cds. GenBank Mar. 2, 2006: 1-2.
Ausubel, Using Synthetic Oligonucleotides as Probes. Current Protocols in Molecular Biology 1988; suppl.: pp. 6,4,01-6.4.10.
Branden and Tooze, Prediction, Engineering and Design of Protein Structures. Introduction to Protein Structure, 1991:247.
Guichard et al., Partially Modified Retro-Inverso Pseudopeptides as Non-natural Ligands for the Human Class I Histocompatibility Molecule HLA-A2. Journal of Medicinal Chemistry May 10. 1996; 39(10): 2030-2039.
Hruby and Bonner; Chapter 11: Design of Novel Synthetic Peptides Including Cyclic Conformationally and Topgraphically Constrained Analogs, Peptide Synthesis Protocols, 1994 Humana Press Inc. : 201-239.
Manheimer, PH0878; 1g kappa chain V region. NCB I Sequence Viewer v2., GenBank May 30, 1997.
International Search Report and Written Opinion dated Apr. 27, 2010 issued in PCT/EP2009/009229.
International Search Report and Written Opinion dated Jun. 2, 2010 issued in PCT/EP2009/009228.
Q9WVI9, JIPI_Mouse Standard; PRT; 707 AA. Database UniProt 2003.
Cui et al., JNK pathway: diseases and therapeutic potential, Acta Pharmacol Sin. May 2007;28(5):601-608.
Josephson et al., High -Efficiency Intracellular Magnetic Labeling with Novel Superpararnagnetic-Tat Peptide Conjugates. Bioconjug Chem. Mar.-Apr. 1999;10(2):186-191.
Moschos et al., Lung Delivery Studies Using siRNA Conjugated to TAT(48-60) and Penetratin Reveal Peptide Induced Reduction in Gene Expression and Induction of Innate Immunity. Bioconjug Chem. Sep.-Oct. 2007:18 (5):1450-1459.
EMBL Sequence Database—R85141, Hillier et al., Homo Sapiens, The WashU -Merck EST Project, p. 1, XP-002076858, USA (Aug. 17, 1995).
Stedrnan's Online Dictionary Definition of "Inflammation", Obtained from www.pdrel.com, last viewed on Dec. 18, 2010, 2 pages.
Conti et al., "Atherosclerosis: a chronic inflammatory disease mediated by mast cells", Central European Journal of Immunology, 2015, pp. 380-386 (Year: 2015).
Rovina et al., "Inflammation and Immune Response in COPD: Where Do We Stand?", Mediators of Inflammation, 2013, pp. 1-9 Year: 2013).
Murdoch et al., "Chronic inflammation and asthma", Mutation Research, 2010, pp. 24-39 (Year: 2010).
Donath et al., Type 2 diabetes as an inflammatory disease, Nature Reviews—Immunology, 2011, pp. 98-107 (Year: 2011).
Todd et al., "GeneticProtection from the Inflammatory Disease Type 1 Diabetes in Humans and Animal Models", Immunity, pp. 387-395 (Year: 2001).
Dugan et al., "Role of c-Jun N-terminal Kinase (JNK) activation in micturition reflexes in cyclophosphamide (CYP)-induced cystitis in female rats," Journal of Molecular Neuroscience, 54(3):360-369 (2014).
Juszczak et al., "Animal models of overactive bladder: Cyclophosphamide (CYP)-induced cystitis in rats", N46, EAU 3rd North Eastern European Meeting (NEEM)/ European Urology Supplements 8 (2009) 583-584 (Year: 2009).

(56) References Cited

OTHER PUBLICATIONS

Chemical Abstracts Database, Accession No. 133:204452 CA, (Sep. 29, 2000), 3 pages; XP002554007.
Cerbone et al., "AS601245, an anti-inflammatory JNK inhibitor, and clofibrate have a synergistic effect in inducing cell responses and in affecting the gene expression profile in CaCo-2 colon cancer cells," PPAR Research, 2012: 269751, 1-16 (2012).
Budur et al., "A pharmacogenetics supported clinica trial to delay onset of mild cognitive impairment due to Alzheimer's disease using low dose pioglitazone: the tomorrow study," Neuropsychopharmacology, 39: S342 (2014).
Bloch et al., "Increased ERK and JNK activation and decreased ERK/JNK ratio are associated with long-term organ damage in patients with systemic lupus erythematosus," Rheumatology 53: 1034-1042 (2014).
Barichello et al., "Dexamethasone treatment reverses cognitive impairment but increases brain oxidative stress in rats submitted to pneumococcal meningitis," Oxidative Medicine and Cellular Longevity, 1-7 (2011).
Aisen et al., "A randomized controlled trial of prednisone in Alzheimer's disease," Neurology, 54: 588-593 (2000).
Melino et al., "The effect of the JNK inhibitor, JIP peptide, on human T lymphocyte proliferation and cytokine production," 181(10): 7300-7306 (2008).
Wang et al., "JNK inhibition as a potential strategy in treating Parkinson's disease," Drug News Perspect., 17 (10):646-654 (2004).
Weston et al., "The JNK signal transduction pathway," Curr. Opin. Cell Biol., 19(2):142-149, (2007).
Soejima et al., "Activation of MKK4 (SEK1), JNK, and C-Jun in Labial Salivary Infiltrating T Cells in Patients With Sjogren's Syndrome," Rheumatology International, 27(4): 329-333 (2006).
Shimazawa et al., "Inhibitor of double stranded RNA-dependent protein kinase protects against cell damage induced by ER stress," Neurosci Lett., 409(3):1 92-195 (2006).
Nakamura et al., "Expression of mitogen activated protein kinases in labial salivary glands of patients with Sjogren's syndrome," Annals of the Rheumatic Diseases, 58(6):382-385 (1999).
Manning et al., "Targeting JNK for therapeutic benefit: from junk to gold?" Nature Reviews Drug Discovery, 2: 554-565 (2003).
Hanyu et al., "Pioglitazone improved cognition in a pilot study on patients with Alzheimer's disease and mild cognitive impairmenl with diabetes mellitus," Journal of the American Geriatrics Society, 57(1):177-179 (2009).
Janin, "Protein—Protein Interactions" Encyclopedia of Molecular Biology (Creighton, ed.) 2027-2033 (1999).
Horvath et al., "Somatostatin Octa- and Heptapeptides, Structural and Biological Characteristics," Peptides (Ramage el al, ed) 483-484 (1996).
Neidle, S. ed., "Cancer Drug Design and Discovery," Elsevier/Academic Press, 427-431 (2008).
Auerbach et al., "Angiogenesis assays: Problems and pitfalls," Cancer and Metastasis Reviews, 19: 167-172 (2000).
Jain, R., "Barriers to Drug Delivery in Solid Tumors," Scientific American, 58-65 (1994).
Sporn et al., "Chemoprevention of cancer," Carcinogenesis, 21: 525-530 (2000).
Database UniProt, Retrieved from EBI, Database Accession No. Q9WVI9, Abstract (Feb. 28, 2003).
Guichard et al.; Horvath et al.; Hruby et al., Peptides 1996: Proceedings of the twenty-fourth European Peptide Symposium, Sep. 8-13, 1996, Edinburgh, Scotland; Ramage /Epton (Eds.), The European Peptide Society, Mayflower Scientific Ltd., Kingswinford, pp. 447-450 and 483-486 (1996).
Chung et al., "Endogenous Nerve Growth Factor Regulates Collagen Expression and Bladder Hypertrophy Through AKT and MAPK Pathways During Cystitis," Journal of Biological Chemistry, 285: 4206-4212 (2010).
Office Action dated Feb. 1, 2016 issued in U.S. Appl. No. 14/367,706, 24 pages.
Office Action dated Mar. 21, 2014 issued in U.S. Appl. No. 13/141,314, 21 pages.
Office Action dated Jul. 31, 2014 issued in U.S. Appl. No. 13/141,314, 17 pages.
Office Action dated Aug. 27, 2015 issued in U.S. Appl. No. 13/141,314, 9 pages.
Office Action dated Mar. 23, 2017 issued in U.S. Appl. No. 14/891,067, 14 pages.
Office Action dated Nov. 20, 2017 issued in U.S. Appl. No. 14/891,067, 12 pages.
Office Action dated Jun. 14, 2018 issued in U.S. Appl. No. 14/891,067, 15 pages.
Office Action dated Mar. 22, 2019 issued in U.S. Appl. No. 14/891,067, 17 pages.
Office Action dated Sep. 27, 2019 issued in U.S. Appl. No. 14/891,067, 10 pages.
Office Action dated Aug. 16, 2018 issued in U.S. Appl. No. 15/321,893, 8 pages.
Office Action dated Dec. 4, 2017 issued in U.S. Appl. No. 15/321,904, 14 pages.
Office Action dated Nov. 29, 2018 issued in U.S. Appl. No. 15/737,480, 16 pages.
Office Action dated Jan. 30, 2019 issued in U.S. Appl. No. 15/628,771, 17 pages.
Office Action dated Aug. 24, 2017 issued in U.S. Appl. No. 15/516,943, 14 pages.
Office Action dated Jun. 15, 2018 issued in U.S. Appl. No. 15/516,943, 9 pages.
Office Action dated Jan. 10, 2019 issued in U.S. Appl. No. 15/516,943, 10 pages.
Office Action dated Aug. 8, 2019 issued in U.S. Appl. No. 15/516,943, 11 pages.
Office Action dated Dec. 11, 2013 issued in U.S. Appl. No. 14/035,450, 9 pages.
Office Action dated Sep. 24, 2014 issued in U.S. Appl. No. 14/035,450, 7 pages.
Office Action dated Apr. 27, 2015 issued in U.S. Appl. No. 14/035,450, 10 pages.
Office Action dated Aug. 31, 2015 issued in U.S. Appl. No. 14/035,450, 10 pages.
Office Action dated May 2, 2016 issued in U.S. Appl. No. 14/035,450, 10 pages.
Office Action dated Oct. 23, 2017 in U.S. Appl. No. 15/217,326, 21 pages.
Office Action dated May 13, 2018 in U.S. Appl. No. 15/217,326, 16 pages.
Office Action dated Feb. 7, 2019 in U.S. Appl. No. 15/217,326, 14 pages.
Office Action dated Jan. 26, 2017 in U.S. Appl. No. 14/849,374, 19 pages.
Office Action dated Sep. 26, 2017 in U.S. Appl. No. 14/849,374, 16 pages.
Office Action dated Mar. 29, 2017 in U.S. Appl. No. 15/045,058, 43 pages.
Office Action dated Jul. 22, 2015 in U.S. Appl. No. 14/144,938, 12 pages.
Office Action dated Dec. 28, 2010 in U.S. Appl. No. 12/066,657, 27 pages.
Office Action dated Jun. 28, 2010 in U.S. Appl. No. 12/066,657, 9 pages.
Office Action dated Jul. 19, 2012 in U.S. Appl. No. 12/066,657, 13 pages.
Office Action dated Jul. 8, 2011 in U.S. Appl. No. 12/101,911, 14 pages.
Office Action dated Aug. 29, 2006 in U.S. Appl. No. 10/457,614, 21 pages.
Office Action dated Oct. 12, 2007 in U.S. Appl. No. 10/457,614, 17 pages.
Ohelke et al., Van Regenmortel et ai., Saito et al., Peptide Science-Present and Future, Edited by Y. Shimonishi, Kluwer Academic Publishers, Dordrecht, The Netherlands, pp. 782-787 and 805-807 (1999).

(56) References Cited

OTHER PUBLICATIONS

Guichard et al., Partially Modified Retro-inverson Psudopeptides as Non-natural Ligands for the Human Class I Histocompatibility Molecule, HLA-A2, Peptides (Ramage et al. ed) 449-450 (1996).
www.healthline.com—"What is Cystitis?", obtained Sep. 21, 2019; pp. 1-14 (Year: 2019).
Guichard et al., "Mimicry of an immunodominant Epitope of Foot and Mouth Disease Virus with Retro-inverson Isomers: A New Approach in the Design of Peptide Based Vaccines," Peptides (Ramage et al. ed) 447-448 (1996).
Sclip A et al. c-Jun N-terminal kinase regulates soluble Abeta oligomers and cognitive impairment in AD mouse model. J. Biol. Chem. 286(51), 43871-43880. (Year: 2011).
TgCRND8 Research Model, Alzforum, www.alzforum.org/research-models/tgcrnd8, retrieved Nov. 25, 2018. (Year: 2018).
XG—102 C-Terminal acid, Compound Summary for CID 72941992, PubChem, pubchem.ncbi.nlm.nih.gov / compound /72941992#section =Top, retrieved Nov. 24, 2018. (Year: 2018).
Sclip A et al. c-Jun N-terminal kinase has a key role in Alzheimer disease synaptic dysfunction in vivo. Cell Death and Disease, 5, e1019. Published online Jan. 23, 2014. (Year: 2014).
Sharma N et al. SP600125, a competitive inhibitor of JNK attenuates streptozotocin induced neurocognitive deficit and oxidative stress in rats, Pharmacology, Biochemistry and Behavior, 96, 386-394. (Year: 2010).
Dugan et al., "Role of c-Jun N-terminal Kinase (JNK) activation in micturition reflexes in cyclophosphamide (CYP)-induced cystitis in female rats", Society for Neuroscience Abstract Viewer and Itinerary Planner,2011,41st Ann. Meeting of the Society-for-Neuroscience Washington, DC, USA. Nov. 12-16, (Year: 2011).
U.S. Appl. No. 14/849,374, filed Sep. 9, 2015.
U.S. Appl. No. 13/879,059, filed Sep. 5, 2013.
U.S. Appl. No. 16/751,439, filed Jan. 24, 2020.

\* cited by examiner

| | | | | | |
|---|---|---|---|---|---|
| ccgcccagc | tcagtccgaa | tcccgtggcg | gcggcggcct | cctccacacg | cttccactct | 60
| cgccgccgcc | gccgccgccg | ccgtcttccg | tcgcgttctc | cgcccggatg | gtcaggctga | 120
| gcccgggaat | ggcggagcga | gagagcggcc | tgagcgggg | tgccggtcc | ctaccggccg | 180
| cttccccatt | cctgggactg | cacatcgt | cgcctccaa | tttcaggtc | acccatgata | 240
| tcagcctgga | ggagtttgag | gatgaagacc | tttcggagat | cactgatgag | tgtggcatca | 300
| gcctgcaytg | caaagacacc | ttgtctctcc | ggccccgcg | tgccgggcta | ctgtctgcgg | 360
| gtagcagcgg | tagcgcgggg | agccggctgc | aggcggagat | gctgcagatg | gacctgatcg | 420
| acgcggcaag | tgacactccg | ggcgctgagg | acgacgaaga | ggacgacgac | gagctgctg | 480
| cccaacggcc | aggagtgggg | cctccaaag | ccgagtctgg | ccaggagccg | gcgtcctgca | 540
| gccagggtca | gggccaggc | cccggcacag | gctgcggaga | cacctaccgg | cccaagaggc | 600
| ctaccacgct | caaccttttc | ccgcagtgc | cgcggtctg | ggacacgctg | aataataact | 660
| ctttaggcaa | aaagcacagt | tggcaggacc | gtgtgtctcg | atcatcctcc | cctctgaaga | 720
| cagggagca | gacgcttca | catgaactca | tctgcctgag | tgatgagctg | ccgccccagg | 780
| gcagtcctgt | tcccaccag | gatcgtggca | cttccaccga | cagccctgt | cgccgtactg | 840
| cagccaccca | gatggcactt | ccaagtggtc | cccctgccac | tgcacttggt | ggccggggcc | 900
| actcccatcg | agatcggtcc | atatcagcag | atytgcgct | ccaggcgact | gaggagatct | 960
| acctgacccc | agtgcagagg | ccccccagaa | ctgcagaacc | cacctccacc | ttcttgccac | 1020
| ccactgagag | ccggatgtct | gtcagtcgg | atcctgaccc | tgccgcttac | tctgtaactg | 1080
| cagggtgact | gcaccctcc | atcagtgaag | aggatgaggg | cttcgactgt | ctgtcatccc | 1140
| cagagcaagc | tgagctacca | gtgggagggt | ggcggggaag | cctcggggag | ccaccaccgc | 1200
| cttccactggc | ctcactgagc | tcggacacca | gcgcactgtc | ctacgactct | gtcaagtaca | 1260
| cactggtggt | ggatgagcat | gcccagcttg | agttggtgag | cctgcggcca | tgtttggag | 1320
| attacagtga | cgaaagcgac | tctgcactg | tctatgacaa | ctgtgcctct | gcctcctcgc | 1380
| cctacgagtc | agccattggt | gaggaatatg | aggaggcccc | tcaaccccgg | cctccacct | 1440
| gcctgtcaga | ggactccaca | cggatgagc | ctgacgtcca | cttcttcaag | aagtttctga | 1500
| atgtcttcat | gagtggccgc | tctgttcct | ccagtgccga | gtcctttggg | ctgtcctcct | 1560
| gtgtcatcaa | tggggaggag | catgagcaaa | cccattcggc | tatattcagg | tttgtgctc | 1620
| ggcatgaaga | tgaacttgag | ctggaagtgg | acgaccctct | gctggtggag | ctgcaggcag | 1680

Fig. 10

```
aagactattg gtatgaggcc tataacatgc gtactggagc ccgtggtgtc tttcctgcct    1740
actatgccat tgaggtcacc aaggagcctg agcacatggc agccctgcc  aaaaacagcg    1800
actggattga ccagttccgg gtgaagttcc tgggctctgt ccaggttcct tatcacaagg    1860
gcaatgatgt cctctgtgct gctatgcaaa agatgccac  cacccgccgg ctcaccgtgc    1920
actttaaccc gccctccagc tgtgtccttg aaatcagcgt tagggtgtc  aagatagtg    1980
tcaaagctga tgaagctcag gaggccaagg gaaataaatg tagccactt  ttccagctaa    2040
aaaacatctc tttctgtggg taccatccaa agaacaatcaa gtactttggg tttatcacta    2100
agcaccctgc tgaccaccgg tttgcctgcc atgtctttgt gtctgaagat tccaccaaag    2160
ccctggcaga gtctgtgggg cgtgcattc  agcagttcta caagcaattt gtggaatata    2220
cctgtcctac agaagatatc tacttggagt agcagcaacc cccctctctg cagcccctca    2280
gccccaggcc agtactagga cagctgactg ctgacaggat gttgtactgc cacgagagaa    2340
tggggagtg  agggctgttg gggtcgggg  gcagggattt gggagaaggc agatgcagtt    2400
tattgtaata tatgggtta  gattaatcta tggagacag  tacaggctct ctcggggctg    2460
gggaaggca  gggctgggt  gggggtcagg catctgcca  caaaggggtc ccctaggggac   2520
agaggcgctg caccatcctg ggcttgtttc atactagagg ccctggcttt ctggccttg    2580
ggtcctgcct tgacaaagcc cagcacctg  gaagtgtcac cttcccttgt ccacctcacc    2640
cagtgccctg agctcatgct gagccaagc  acctccgaag gacttccag  taaggaaatg    2700
gcaacatgtg acagtgagac cctgttctca tctgtgggc  tccggcagct ccgaccccca    2760
gcctggccag cacgctgacc ctggcaagct tgtgtgttca aagaaggaga gggccagc     2820
aagccctgcc tgccagggaa ggttccctct cagctggccc cagccactg  gtcactgtct    2880
tgtcacctgg ctactactat taaagtgcca tttcttgtct gaaaaaaaaa aaaaaaaaa    2940
aaaaaactc  gag                                                      2953
```

Fig. 10 (cont.)

Met Ala Arg Leu Ser Pro Gly Met Ala Glu Arg Glu Ser Gly Leu Ser
1               5                   10                  15

Gly Gly Ala Ala Ser Pro Pro Ala Ala Ser Pro Phe Leu Gly Leu His
            20                  25                  30

Ile Ala Ser Pro Pro Asn Phe Arg Leu Thr His Asp Ile Ser Leu Glu
            35                  40              45

Glu Phe Glu Asp Glu Asp Leu Ser Glu Ile Thr Asp Glu Cys Gly Ile
50                  55                  60

Ser Leu Gln Cys Lys Asp Thr Leu Ser Leu Arg Pro Pro Arg Ala Gly
65                  70                  75              80

Leu Leu Ser Ala Gly Ser Ser Gly Ser Ala Gly Ser Arg Leu Gln Ala
                85                  90                  95

Glu Met Leu Gln Met Asp Leu Ile Asp Ala Ala Ser Asp Thr Pro Gly
100                 105                 110

Ala Glu Asp Asp Asp Glu Glu Asp Asp Glu Leu Ala Ala Gln Arg Pro
115                 120                 125

Gly Val Gly Pro Ser Lys Ala Gly Leu Gln Gly Pro Ala Ser Arg
130                 135                 140

Ser Gln Gly Gln Gly Gly Pro Thr Thr Gly Cys Gly Asp Thr Tyr
145                 150                 155             160

Arg Pro Lys Arg Pro Thr Thr Leu Asn Leu Phe Pro Gln Val Pro Arg
                165                 170                 175

Ser Gln Asp Thr Leu Asn Asn Asn Ser Leu Gly Lys Lys His Ser Trp
                180                 185                 190

Gln Asp Arg Val Ser Arg Ser Ser Pro Leu Lys Thr Gly Glu Gln
                195                 200                 205

Thr Pro Pro His Glu His Ile Cys Leu Ser Asp Gly Leu Pro Pro Gln
210                 215                 220

Gly Ser Pro Val Pro Thr Gln Asp Arg Gly Thr Ser Thr Asp Ser Pro
225                 230                 235                 240

Cys Arg Arg Thr Ala Ala Thr Gln Met Ala Pro Pro Ser Gly Pro Pro
                245                 250                 255

Fig. 11

Ala Thr Ala Pro Gly Gly Arg Gly His Ser His Arg Asp Arg Ser Ile
260                 265                 270

Ser Ala Asp Val Arg Leu Glu Ala Thr Glu Glu Ile Tyr Leu Thr Pro
    275                 280                 285

Val Gln Arg Pro Asp Pro Ala Glu Pro Thr Ser Phe Leu Pro
290                 295                 300

Pro Thr Glu Ser Arg Met Ser Val Ser Ser Asp Pro Asp Pro Ala Ala
305                 310                 315                 320

Tyr Ser Val Thr Ala Gly Arg Pro His Pro Ser Ile Ser Glu Glu Asp
        325                 330                 335

Glu Gly Phe Asp Cys Leu Ser Ser Pro Gln Ala Glu Pro Pro Gly
    340                 345                 350

Gly Gly Trp Arg Gly Ser Leu Gly Leu Pro Pro Pro Pro Arg Ala
355                 360                 365

Ser Leu Ser Ser Asp Thr Ser Ala Leu Ser Tyr Asp Ser Val Lys Tyr
370                 375                 380

Thr Leu Val Val Asp Glu His Ala Gln Leu Glu Leu Val Ser Leu Arg
385                 390                 395                 400

Pro Cys Phe Gly Asp Tyr Ser Asp Glu Ser Ala Thr Val Tyr
        405                 410                 415

Asp Asn Cys Ala Ser Ala Ser Ser Pro Tyr Gly Ser Ala Ile Gly Glu
        420                 425                 430

Glu Tyr Glu Glu Ala Pro Gln Pro Arg Pro Pro Thr Cys Leu Ser Glu
    435                 440                 445

Asp Ser Thr Pro Asp Glu Pro Asp Val His Phe Ser Lys Lys Phe Leu
450                 455                 460

Asn Val Phe Met Ser Gly Arg Ser Arg Ser Ser Ala Glu Ser Phe
        465     470                 475                 480

Gly Leu Phe Ser Cys Val Ile Asn Gly Glu Glu His Glu Gln Thr His
        485                 490                 495

Arg Ala Ile Phe Arg Phe Val Pro Arg His Pro Asp Gly Leu Glu Leu
500                 505                 510

Fig. 11 (cont.)

Glu Val Asp Asp Pro Leu Val Glu Leu Gln Ala Glu Asp Tyr Trp
515                 520                 525

Tyr Glu Ala Tyr Asn Met Arg Thr Gly Ala Arg Gly Val Phe Pro Ala
530                 535                 540

Tyr Tyr Ala Ile Glu Val Thr Lys Glu Pro Glu His Met Ala Ala Leu
545                 550                 555                 560

Ala Lys Asn Ser Asp Trp Ile Asp Gln Phe Arg Val Lys Phe Leu Gly
565                 570                 575

Ser Val Gln Val Pro Tyr His Lys Gly Asn Asp Val Leu Cys Ala Ala
580                 585                 590

Met Gln Lys Ile Ala Thr Thr Arg Arg Leu Thr Val His Phe Asn Pro
595                 600                 605

Pro Ser Cys Val Leu Glu Ile Ser Val Arg Gly Val Lys Ile Gly
610                 615                 620

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
645                 650                 655

Asn Lys Tyr Phe Gly Phe Ile Thr Lys His Pro Ala Asp His Arg Phe
660                 665                 670

Ala Cys His Val Phe Val Ser Glu Asp Ser Thr Lys Ala Leu Ala Glu
675                 680                 685

Ser Val Gly Arg Ala Phe Gln Gln Phe Tyr Lys Gln Phe Val Glu Tyr
690                 695                 700

Thr Cys Pro Thr Glu Asp Ile Tyr Leu Glu
705                 710

Fig. 11 (cont.)

Met Ala Glu Arg Glu Ser Gly Gly Leu Gly Gly Ala Ala Ser Pro
1               5                   10                  15

Pro Ala Ala Ser Pro Phe Leu Gly Leu His Ile Ala Ser Pro Asn
            20                  25                  30

Phe Arg Leu Thr His Asp Ile Thr Ser Leu Glu Glu Phe Glu Asp Glu Asp
            35                  40                  45

Leu Ser Glu Gly Ile Thr Asp Gly Cys Gly Ile Ser Leu Gln Cys Lys Asp
            50                  55                  60

Thr Leu Ser Leu Arg Pro Pro Arg Ala Gly Leu Leu Ser Ala Gly Gly
65              70                  75                  80

Gly Gly Ala Gly Ser Arg Leu Gln Ala Gly Met Leu Gln Met Asp Leu
            85                  90                  95

Ile Asp Ala Thr Gly Asp Thr Pro Gly Ala Gly Asp Asp Glu Asp
            100                 105                 110

Asp Asp Glu Gly Glu Arg Ala Ala Arg Arg Pro Gly Ala Gly Pro Pro Lys
            115                 120                 125

Ala Glu Ser Gly Gln Glu Pro Gly Ser Arg Gly Gln Gly Gln Ser Gln
130                 135                 140

Gly Gln Ser Gln Gly Pro Gly Ser Asp Thr Tyr Arg Pro Lys Arg
            145                 150                 155             160

Pro Thr Thr Leu Asn Leu Phe Pro Gln Val Pro Arg Ser Gln Asp Thr
            165                 170                 175

Leu Asn Asn Asn Ser Leu Gly Lys Lys His Ser Trp Gln Asp Arg Val
            180                 185                 190

Ser Arg Ser Ser Ser Pro Leu Lys Thr Gly Glu Gln Thr Pro Pro His
            195                 200                 205

Glu His Ile Cys Leu Ser Asp Glu Leu Pro Pro Gln Ser Gly Pro Ala
210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Pro Ala Ala Pro Pro
            245                 250                 255

Fig. 12

Gly Gly Arg Gly His Ser His Arg Asp Arg Ile His Tyr Gln Ala Asp
260                 265                 270

Val Arg Leu Glu Ala Thr Glu Ile Tyr Leu Thr Pro Val Gln Arg
275                 280                 285

Pro Pro Asp Ala Ala Glu Pro Thr Ser Ala Phe Leu Pro Pro Thr Glu
290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Gly Gly Phe
            325                 330                 335

Asp Cys Leu Ser Ser Pro Glu Arg Ala Glu Pro Pro Gly Gly Gly Trp
340                 345                 350

Arg Gly Ser Leu Gly Glu Pro Pro Pro Pro Arg Ala Ser Leu Ser
355                 360                 365

Ser Asp Thr Ser Ala Leu Ser Tyr Asp Ser Val Lys Tyr Thr Leu Val
370                 375                 380

Val Asp Glu His Ala Gln Leu Val Ser Leu Arg Pro Cys Phe
385                 390                 395                 400

Gly Asp Tyr Ser Glu Ser Ala Thr Val Tyr Asp Asn Cys
        405                 410                 415

Ala Ser Val Ser Ser Pro Tyr Glu Ser Ala Ile Gly Glu Gly Tyr Glu
            420                 425                 430

Glu Ala Pro Arg Pro Gln Pro Pro Ala Cys Leu Ser Glu Asp Ser Thr
        435                 440                 445

Pro Asp Glu Pro Asp Val His Phe Ser Lys Lys Phe Leu Asn Val Phe
450                 455                 460

Met Ser Gly Arg Ser Arg Ser Ser Ser Ala Glu Ser Phe Gly Leu Phe
465                 470                 475                 480

Ser Cys Ile Asn Gly Glu Glu Gln Thr His Arg Ala Ile
            485                 490                 495

Phe Arg Phe Val Pro Arg His Glu Asp Glu Leu Glu Leu Gly Val Asp
500                 505                 510

Fig. 12 (cont.)

Asp Pro Leu Val Glu Leu Gln Ala Glu Asp Tyr Trp Tyr Glu Ala
515                 520                 525

Tyr Asn Met Arg Thr Gly Ala Arg Gly Val Phe Pro Ala Tyr Ala
530                 535                 540

Ile Glu Val Thr Lys Gln Pro Glu His Met Ala Ala Leu Ala Lys Asn
545                 550                 555                 560

Ser Asp Trp Val Asp Phe Gln Arg Val Lys Phe Leu Gly Ser Val Gln
565                 570                 575

Val Pro Tyr His Lys Gly Asn Asp Val Leu Cys Ala Ala Met Gln Lys
580                 585                 590

Ile Ala Thr Thr Arg Arg Leu Thr Val His Phe Asn Pro Pro Ser Ser
595                 600                 605

Cys Val Leu Glu Ile Ser Val Arg Gly Val Lys Ile Gly Val Lys Ala
610                 615                 620

Asp Asp Ser Gln Glu Lys Gly Asn Lys Cys Ser His Phe Phe Gln
625                 630                 635                 640

Leu Lys Asn Ile Ser Phe Cys Gly Tyr His Pro Lys Asn Asn Lys Tyr
645                 650                 655

Phe Gly Phe Ile Thr Lys His Pro Ala Asp His Arg Phe Ala Cys His
660                 665                 670

Val Phe Val Ser Glu Asp Ser Thr Lys Ala Leu Ala Glu Ser Val Gly
675                 680                 685

Arg Ala Phe Gln Gln Phe Tyr Lys Gln Phe Val Gln Phe Val Thr Cys Pro
690                 695                 700

Thr Glu Asp Ile Tyr Leu Glu
705                 710

Fig. 12 (cont.)

| | | | | | |
|---|---|---|---|---|---|
| atggcgggagc | gagaaagctgg | cggcctggaa | gggggggccg | tgtcccgcc | cgccgcctct | 60 |
| ccgttcctgg | ggctgcacat | cgcttgcct | cccaattca | ggctccacca | tgacattagc | 120 |
| ctggaggagt | ttgaggatga | agatcctctcg | gagatcactg | atgagtgtgg | catcagctta | 180 |
| cagtgcaaag | acaccctgtc | cttacgccc | ccgccgccg | ggctgtctc | tgcgggcggc | 240 |
| ggcggtcgg | ggagccggtt | gcaggccgag | atgctgcaga | tggacctgat | cgacgcacg | 300 |
| gggacactc | ccggggctga | ggacgacgag | gaggatgacg | acgaggagcg | cgcggcccgg | 360 |
| cggccgggag | cgggcccgcc | caaggccgag | tccggccagg | agtcggcgtc | ccggccag | 420 |
| ggccagagc | aaggccagag | ccaggccg | ggcagcaggg | acacgtaccg | gcccaagcgg | 480 |
| cccaccagc | tcaacctctt | tccgcaggtg | ccggtgtctc | aggacacact | gaataataat | 540 |
| tctctgggca | aaaagcacg | tggcaggat | cggtgtctc | gatcatcctc | accccctgaag | 600 |
| acaggggagc | agacactacc | gcatgaacac | atctgcctga | gcgatgagct | gcccccccag | 660 |
| agggctcccg | ccccaccac | agatcgaggc | accttcaccg | acagccctg | ccgccgagc | 720 |
| acagctacc | agatggcacc | tccgggtggt | cccctgctg | cccgccgtg | gggtcggggc | 780 |
| cactcgcatc | gagaccgaat | ccactaccag | gcgatgtgc | gactagaggc | cactgaggag | 840 |
| atctactga | cccagtgca | gaggccccca | gactgtcag | agcccacctc | cgccttcctg | 900 |
| ccgccactg | agagccggat | gtcagtcagc | tccgatccag | accctgccgc | ctaccccttc | 960 |
| acggcagggc | ggctgcaccc | ctccatcagt | gaagaggaag | agggcttcga | ctgcctgtcg | 1020 |
| tccccagagc | gggctgagcc | ccccaggcga | gggtgtcggg | ggagctggg | ggagctgccg | 1080 |
| ccacttccac | gggcctctct | gagctggaac | accagcgccc | tgtcctatga | ctctgtcaag | 1140 |
| tacacgctgg | tggtagatga | gcatgccaag | ctggagctgg | tgaggctgcg | gccgtgctcc | 1200 |
| ggagactaca | gtgacgagag | tgacctgcc | accgtctatg | acactgtgc | ctccgtctcc | 1260 |
| tcgccctatg | agtcggccat | cggagaggaa | tatgaagagg | ccccggcc | ccagccccct | 1320 |
| gcctgcctct | ccgaggactc | cacgccgat | gaaccgacg | tccatttctc | caagaaattc | 1380 |
| ctgaacgcct | tcatgagtgg | ccgctcccgc | tcctccagtg | ctgagtcctt | cgggtgttc | 1440 |
| tcctgcatca | tcaacgggga | ggagcaggag | cagaccacc | gggccatatt | caggtttgtg | 1500 |
| cctgcacacg | aagacgaact | tgagctggaa | gtggatgacc | ctctgctagt | ggagctccag | 1560 |
| gctgaagact | actggtacga | ggcctacaac | atgcgcactg | gtgccgggg | tgtcttcct | 1620 |
| gccattacg | ccatcgaggt | caccaaggag | cccgagcaca | tggcagccct | ggccaaaaac | 1680 |
| agtgactgg | tgaccagtt | ccgggtgaag | ttcctgggct | cagtccaggt | tccctatcac | 1740 |

Fig. 13

| | | | | | |
|---|---|---|---|---|---|
| aagggtaatg | acgtcctctg | tgctgctatg | taaaagattg | ctaccacccg | ccggctcacc | 1800
| gtgcacttta | acccgccctc | cagctgtgtc | ctggagatca | gcgtgcgggg | tgtgaagata | 1860
| ggcgtcaagg | ccgatgactc | ccaggaggcc | aagggaata | aatgtagcca | cttttccag | 1920
| ttaaaaaaca | tctcttttctg | cggatatcat | ccaaagaaca | acaagtactt | tgggttcatc | 1980
| accaagcacc | ccgccgacca | ccggtttgcc | tgccacgtct | ttgtgtctga | agactccacc | 2040
| aaagccctgg | cagagtccgt | ggggagagca | ttccagcagt | tctacaagca | gtttgtggag | 2100
| tacacctgcc | ccacagaaga | tatctacctg | gagtag | | | 2136

Fig. 13 (cont.)

SEQUENCE LISTING

```
<160> NUMBER OF SEQ ID NOS: 108

<210> SEQ ID NO 1
<211> LENGTH: 19
<212> TYPE: PRT
<213> ORGANISM: Artificial
<220> FEATURE:
<223> OTHER INFORMATION: Description of sequence: Peptide L-IB1(s) (see
      Table 1)

<400> SEQUENCE: 1

Arg Pro Lys Arg Pro Thr Thr Leu Asn Leu Phe Pro Gln Val Pro Arg
1               5                   10                  15
```

Ser Gln Asp

```
<210> SEQ ID NO 2
<211> LENGTH: 19
<212> TYPE: PRT
<213> ORGANISM: Artificial
<220> FEATURE:
<223> OTHER INFORMATION: Description of sequence: Peptide D-IB1(s) (see
      Table 1)
<220> FEATURE:
<221> NAME/KEY: MUTAGEN
<222> LOCATION: (1)..(19)
<223> OTHER INFORMATION: all amino acids are D-amino acids

<400> SEQUENCE: 2

Asp Gln Ser Arg Pro Val Gln Pro Phe Leu Asn Leu Thr Thr Pro Arg
1               5                   10                  15

Lys Pro Arg

<210> SEQ ID NO 3
<211> LENGTH: 19
<212> TYPE: PRT
<213> ORGANISM: Artificial
<220> FEATURE:
<223> OTHER INFORMATION: Description of sequence: Peptide L-IB (generic)
      (s) (see Table 1)
<220> FEATURE:
<221> NAME/KEY: misc_feature
<223> OTHER INFORMATION: Description of sequence: Description of
      sequence: general formula: NH2-Xnb-Xna-RPTTLXLXXXXXXXQD-Xnb-COOH
      (see Table 1)
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (2)..(2)
<223> OTHER INFORMATION: Xaa is Xna as defined in the general formula,
      wherein Xaa represents an amino acid residue, preferably selected
      from any (native) amino acid residue residue except serine and
      threonine
<220> FEATURE:
<221> NAME/KEY: REPEAT
<222> LOCATION: (2)..(2)
<223> OTHER INFORMATION: Xaa is Xna as defined in the general formula,
      wherein n is 0 or 1
<220> FEATURE:
<221> NAME/KEY: VARIANT
<222> LOCATION: (8)..(8)
<223> OTHER INFORMATION: Xaa represents an amino acid residue,
      preferably selected from any (native) amino acid residue;
<220> FEATURE:
<221> NAME/KEY: VARIANT
<222> LOCATION: (10)..(16)
<223> OTHER INFORMATION: Xaa represents an amino acid residue,
      preferably selected from any (native) amino acid residue;
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;
```

-continued

```
<400> SEQUENCE: 3

Xaa Xaa Arg Pro Thr Thr Leu Xaa Leu Xaa Xaa Xaa Xaa Xaa Xaa Xaa
1               5                   10                  15

Gln Asp Xaa

<210> SEQ ID NO 4
<211> LENGTH: 19
<212> TYPE: PRT
<213> ORGANISM: Artificial
<220> FEATURE:
<223> OTHER INFORMATION: Description of sequence: Peptide D-IB (generic)
      (s) (see Table 1)
<220> FEATURE:
<221> NAME/KEY: misc_feature
<223> OTHER INFORMATION: Description of sequence: general formula:
      NH2-Xnb-DQXXXXXXXLXLTTPR-Xna-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (4)..(10)
<223> OTHER INFORMATION: Xaa represents an amino acid residue,
      preferably selected from any (native) amino acid residue;
<220> FEATURE:
<221> NAME/KEY: VARIANT
<222> LOCATION: (12)..(12)
<223> OTHER INFORMATION: Xaa represents an amino acid residue,
      preferably selected from any (native) amino acid residue;
<220> FEATURE:
<221> NAME/KEY: REPEAT
<222> LOCATION: (18)..(18)
<223> OTHER INFORMATION: Xaa is Xna as defined in the general formula,
      wherein n is 0 or 1
<220> FEATURE:
<221> NAME/KEY: VARIANT
<222> LOCATION: (18)..(18)
<223> OTHER INFORMATION: Xaa is Xna as defined in the general formula,
      wherein Xaa represents an amino acid residue, preferably selected
      from any (native) amino acid residue residue except serine and
      Threonine
<220> FEATURE:
<221> NAME/KEY: VARIANT
<222> LOCATION: (18)..(18)
<223> OTHER INFORMATION: Xaa is Xna as defined in the general formula,
      wherein Xaa represents an amino acid residue, preferably selected
      from any (native) amino acid residue residue except serine and
      threonine
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;

<400> SEQUENCE: 4

Xaa Asp Gln Xaa Xaa Xaa Xaa Xaa Xaa Xaa Leu Xaa Leu Thr Thr Pro
```

```
1               5                  10                 15

Arg Xaa Xaa

<210> SEQ ID NO 5
<211> LENGTH: 10
<212> TYPE: PRT
<213> ORGANISM: Artificial
<220> FEATURE:
<223> OTHER INFORMATION: Description of sequence:  Peptide L-TAT (see
      Table 1)

<400> SEQUENCE: 5

Gly Arg Lys Lys Arg Arg Gln Arg Arg Arg
1               5                  10

<210> SEQ ID NO 6
<211> LENGTH: 10
<212> TYPE: PRT
<213> ORGANISM: Artificial
<220> FEATURE:
<223> OTHER INFORMATION: Description of sequence: Peptide D-TAT (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 6

Arg Arg Arg Gln Arg Arg Lys Lys Arg Gly
1               5                  10

<210> SEQ ID NO 7
<211> LENGTH: 11
<212> TYPE: PRT
<213> ORGANISM: Artificial
<220> FEATURE:
<223> OTHER INFORMATION: Description of sequence: Peptide L-generic-TAT
      (s) (see Table 1)
<220> FEATURE:
<221> NAME/KEY: misc_feature
<223> OTHER INFORMATION: General formula: NH2-Xnb-RKKRRQRRR-Xnb-COOH
      (see Table 1)
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
      wherein n is 0-5, 5-10, 10-15, 15-20, 20-30 or more for Xnb

<400> SEQUENCE: 7

Xaa Arg Lys Lys Arg Arg Gln Arg Arg Arg Xaa
1               5                  10

<210> SEQ ID NO 8
<211> LENGTH: 11
```

```
<212> TYPE: PRT
<213> ORGANISM: Artificial
<220> FEATURE:
<223> OTHER INFORMATION: Description of sequence: Peptide D-generic-TAT
      (s) (see Table 1)
<220> FEATURE:
<221> NAME/KEY: misc_feature
<223> OTHER INFORMATION: General formula: NH2-Xnb-RRRQRRKKR-Xnb-COOH
<220> FEATURE:
<221> NAME/KEY: MUTAGEN
<222> LOCATION: (1)..(10)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
      wherein n is 0-5, 5-10, 10-15, 15-20, 20-30 or more for Xnb

<400> SEQUENCE: 8

Xaa Arg Arg Arg Gln Arg Arg Lys Lys Arg Xaa
1               5                   10

<210> SEQ ID NO 9
<211> LENGTH: 31
<212> TYPE: PRT
<213> ORGANISM: Artificial
<220> FEATURE:
<223> OTHER INFORMATION: Description of sequence: L-TAT-IB1 (s) (see
      Table 1)

<400> SEQUENCE: 9

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 10
<211> LENGTH: 29
<212> TYPE: PRT
<213> ORGANISM: Artificial
<220> FEATURE:
<223> OTHER INFORMATION: Description of sequence: Peptide L-TAT
      (generic) (s) (see Table 1)
<220> FEATURE:
<221> NAME/KEY: misc_feature
<223> OTHER INFORMATION: Description of sequence: General formula:
      NH2-Xnb-RKKRRQRRR-Xnb-Xna-RPTTLXLXXXXXXXQD-Xnb-COOH
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
```

```
       wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
       wherein Xaa represents an amino acid residue, preferably selected
       from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
       wherein n is 0-5, 5-10, 10-15, 15-20, 20-30 or more for Xnb
<220> FEATURE:
<221> NAME/KEY: VARIANT
<222> LOCATION: (12)..(12)
<223> OTHER INFORMATION: Xaa is Xna as defined in the general formula,
       wherein Xaa represents an amino acid residue, preferably selected
       from any(native) amino acid residue residue except serine and
       Threonine
<220> FEATURE:
<221> NAME/KEY: REPEAT
<222> LOCATION: (12)..(12)
<223> OTHER INFORMATION: Xaa is Xna as defined in the general formula,
       wherein n is 0 or 1
<220> FEATURE:
<221> NAME/KEY: VARIANT
<222> LOCATION: (18)..(18)
<223> OTHER INFORMATION: Xaa represents an amino acid residue,
       preferably selected from any (native) amino acid residue;
<220> FEATURE:
<221> NAME/KEY: VARIANT
<222> LOCATION: (20)..(26)
<223> OTHER INFORMATION: Xaa represents an amino acid residue,
       preferably selected from any (native) amino acid residue;
<220> FEATURE:
<221> NAME/KEY: VARIANT
<222> LOCATION: (29)..(29)
<223> OTHER INFORMATION: Xaa is Xnb as defined in the general formula,
       wherein Xaa represents an amino acid residue, preferably selected
       from any (native) amino acid residue;
<220> FEATURE:
<221> NAME/KEY: REPEAT
<222> LOCATION: (29)..(29)
<223> OTHER INFORMATION: Xaa is Xnb as defined in the general formula,
       wherein n is 0-5, 5-10, 10-15, 15-20, 20-30 or more for Xnb

<400> SEQUENCE: 10

Xaa Arg Lys Lys Arg Arg Gln Arg Arg Xaa Xaa Arg Pro Thr Thr
1               5                   10                  15

Leu Xaa Leu Xaa Xaa Xaa Xaa Xaa Xaa Xaa Gln Asp Xaa
            20                  25

<210> SEQ ID NO 11
<211> LENGTH: 31
<212> TYPE: PRT
<213> ORGANISM: Artificial
<220> FEATURE:
<223> OTHER INFORMATION: Description of sequence: Peptid D-TAT-IB1 (s)
       (see Table 1)
<220> FEATURE:
<221> NAME/KEY: MUTAGEN
<222> LOCATION: (1)..(31)
<223> OTHER INFORMATION: all amino acids are D-amino acids

<400> SEQUENCE: 11

Asp Gln Ser Arg Pro Val Gln Pro Phe Leu Asn Leu Thr Thr Pro Arg
1               5                   10                  15

Lys Pro Arg Pro Pro Arg Arg Gln Arg Arg Lys Lys Arg Gly
            20                  25                  30

<210> SEQ ID NO 12
<211> LENGTH: 29
<212> TYPE: PRT
```

```
<213> ORGANISM: Artificial
<220> FEATURE:
<223> OTHER INFORMATION: Description of sequence: Peptid: D-TAT
      (generic) (s) (see Table 1)
<220> FEATURE:
<221> NAME/KEY: misc_feature
<223> OTHER INFORMATION: General formula:
      NH2-Xnb-DQXXXXXXXLXLTTPR-Xna-Xnb-RRRQRRKKR-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (4)..(10)
<223> OTHER INFORMATION: Xaa represents an amino acid residue,
      preferably selected from any (native) amino acid residue;
<220> FEATURE:
<221> NAME/KEY: VARIANT
<222> LOCATION: (12)..(12)
<223> OTHER INFORMATION: Xaa represents an amino acid residue,
      preferably selected from any (native) amino acid residue;
<220> FEATURE:
<221> NAME/KEY: VARIANT
<222> LOCATION: (18)..(18)
<223> OTHER INFORMATION: Xaa is Xna as defined in the general formula,
      wherein Xaa represents an amino acid residue, preferably selected
      from any (native) amino acid residue residue except serine and
      threonine
<220> FEATURE:
<221> NAME/KEY: REPEAT
<222> LOCATION: (18)..(18)
<223> OTHER INFORMATION: Xaa is Xna as defined in the general formula,
      wherein n is 0 or 1
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (29)..(29)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (29)..(29)
<223> OTHER INFORMATION: Xaa is Xnb as defined in the general formula,
      wherein n is 0-5, 5-10, 10-15, 15-20, 20-30 or more for Xnb

<400> SEQUENCE: 12

Xaa Asp Gln Xaa Xaa Xaa Xaa Xaa Xaa Xaa Leu Xaa Leu Thr Thr Pro
1               5                   10                  15

Arg Xaa Xaa Arg Arg Arg Gln Arg Arg Lys Lys Arg Xaa
            20                  25

<210> SEQ ID NO 13
<211> LENGTH: 29
```

```
<212> TYPE: PRT
<213> ORGANISM: Artificial
<220> FEATURE:
<223> OTHER INFORMATION: Description of sequence: peptide IB1-long (see
      Table 1)

<400> SEQUENCE: 13

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 14
<211> LENGTH: 27
<212> TYPE: PRT
<213> ORGANISM: Artificial
<220> FEATURE:
<223> OTHER INFORMATION: Description of sequence: Peptide IB2-long (see
      Table 1)

<400> SEQUENCE: 14

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 15
<211> LENGTH: 29
<212> TYPE: PRT
<213> ORGANISM: Artificial
<220> FEATURE:
<223> OTHER INFORMATION: Description of sequence: Peptide derived from
      c-Jun (see Table 1)

<400> SEQUENCE: 15

Gly Ala Tyr Gly Tyr Ser Asn Pro Lys Ile Leu Lys Gln Ser Met Thr
1               5                   10                  15

Leu Asn Leu Ala Asp Pro Val Gly Asn Leu Lys Pro His
            20                  25

<210> SEQ ID NO 16
<211> LENGTH: 29
<212> TYPE: PRT
<213> ORGANISM: Artificial
<220> FEATURE:
<223> OTHER INFORMATION: Description of sequence: Peptide derived from
      ATF2 (see Table 1)

<400> SEQUENCE: 16

Thr Asn Glu Asp His Leu Ala Val His Lys His Lys His Glu Met Thr
1               5                   10                  15

Leu Lys Phe Gly Pro Ala Arg Asn Asp Ser Val Ile Val
            20                  25

<210> SEQ ID NO 17
<211> LENGTH: 23
<212> TYPE: PRT
<213> ORGANISM: Artificial
<220> FEATURE:
<223> OTHER INFORMATION: Description of sequence: Peptide L-IB1 (see
      Table 1)

<400> SEQUENCE: 17

Asp Thr Tyr Arg Pro Lys Arg Pro Thr Thr Leu Asn Leu Phe Pro Gln
1               5                   10                  15
```

```
Val Pro Arg Ser Gln Asp Thr
            20

<210> SEQ ID NO 18
<211> LENGTH: 23
<212> TYPE: PRT
<213> ORGANISM: Artificial
<220> FEATURE:
<223> OTHER INFORMATION: Description of sequence: Peptide D-IB1 (see
      Table 1)
<220> FEATURE:
<221> NAME/KEY: MUTAGEN
<222> LOCATION: (1)..(23)
<223> OTHER INFORMATION: all amino acids are D-amino acids

<400> SEQUENCE: 18

Thr Asp Gln Ser Arg Pro Val Gln Pro Phe Leu Asn Leu Thr Thr Pro
1               5                   10                  15

Arg Lys Pro Arg Tyr Thr Asp
            20

<210> SEQ ID NO 19
<211> LENGTH: 19
<212> TYPE: PRT
<213> ORGANISM: Artificial
<220> FEATURE:
<223> OTHER INFORMATION: Description of sequence: Peptide L-IB (generic)
      (see Table 1)
<220> FEATURE:
<221> NAME/KEY: VARIANT
<222> LOCATION: (1)..(1)
<223> OTHER INFORMATION: Xaa is selected from any amino acid residue,
<220> FEATURE:
<221> NAME/KEY: VARIANT
<222> LOCATION: (7)..(7)
<223> OTHER INFORMATION: Xaa is selected from any amino acid residue,
<220> FEATURE:
<221> NAME/KEY: VARIANT
<222> LOCATION: (9)..(15)
<223> OTHER INFORMATION: Xaa is selected from any amino acid residue,
<220> FEATURE:
<221> NAME/KEY: VARIANT
<222> LOCATION: (18)..(18)
<223> OTHER INFORMATION: Xaa is selected from serine or threonine,
<220> FEATURE:
<221> NAME/KEY: VARIANT
<222> LOCATION: (19)..(19)
<223> OTHER INFORMATION: Xaa is selected from any amino acid residue,

<400> SEQUENCE: 19

Xaa Arg Pro Thr Thr Leu Xaa Leu Xaa Xaa Xaa Xaa Xaa Xaa Xaa Gln
1               5                   10                  15

Asp Xaa Xaa

<210> SEQ ID NO 20
<211> LENGTH: 19
<212> TYPE: PRT
<213> ORGANISM: Artificial
<220> FEATURE:
<223> OTHER INFORMATION: Description of sequence: Peptide D-IB (generic)
      (see Table 1)
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (2)..(2)
```

```
<223> OTHER INFORMATION: Xaa is selected from serine or threonine
<220> FEATURE:
<221> NAME/KEY: VARIANT
<222> LOCATION: (5)..(11)
<223> OTHER INFORMATION: Xaa is selected from any amino acid residue
<220> FEATURE:
<221> NAME/KEY: VARIANT
<222> LOCATION: (13)..(13)
<223> OTHER INFORMATION: Xaa is selected from any amino acid residue
<220> FEATURE:
<221> NAME/KEY: VARIANT
<222> LOCATION: (19)..(19)
<223> OTHER INFORMATION: Xaa is selected from any amino acid residue

<400> SEQUENCE: 20

Xaa Xaa Asp Gln Xaa Xaa Xaa Xaa Xaa Xaa Xaa Leu Xaa Leu Thr Thr
1               5                   10                  15

Pro Arg Xaa

<210> SEQ ID NO 21
<211> LENGTH: 17
<212> TYPE: PRT
<213> ORGANISM: Artificial
<220> FEATURE:
<223> OTHER INFORMATION: Description of sequence: Peptide L-generic-TAT
      (see Table 1)
<220> FEATURE:
<221> NAME/KEY: VARIANT
<222> LOCATION: (1)..(17)
<223> OTHER INFORMATION: Xaa is selected from any amino acid residue

<400> SEQUENCE: 21

Xaa Xaa Xaa Xaa Arg Lys Lys Arg Arg Gln Arg Arg Arg Xaa Xaa Xaa
1               5                   10                  15

Xaa

<210> SEQ ID NO 22
<211> LENGTH: 17
<212> TYPE: PRT
<213> ORGANISM: Artificial
<220> FEATURE:
<223> OTHER INFORMATION: Description of sequence: Peptide D-generic-TAT
      (see Table 1)
<220> FEATURE:
<221> NAME/KEY: MUTAGEN
<222> LOCATION: (1)..(17)
<223> OTHER INFORMATION: all amino acids are D-amino acids
<220> FEATURE:
<221> NAME/KEY: VARIANT
<222> LOCATION: (1)..(17)
<223> OTHER INFORMATION: Xaa is selected from any amino acid residue

<400> SEQUENCE: 22

Xaa Xaa Xaa Xaa Arg Arg Arg Gln Arg Arg Lys Lys Arg Xaa Xaa Xaa
1               5                   10                  15

Xaa

<210> SEQ ID NO 23
<211> LENGTH: 35
<212> TYPE: PRT
<213> ORGANISM: Artificial
<220> FEATURE:
<223> OTHER INFORMATION: Description of sequence: Peptide L-TAT-IB1 (see
      Table 1)

<400> SEQUENCE: 23

Gly Arg Lys Lys Arg Arg Gln Arg Arg Arg Pro Pro Asp Thr Tyr Arg
1               5                   10                  15
```

```
Pro Lys Arg Pro Thr Thr Leu Asn Leu Phe Pro Gln Val Pro Arg Ser
            20                  25                  30

Gln Asp Thr
        35
```

<210> SEQ ID NO 24
<211> LENGTH: 42
<212> TYPE: PRT
<213> ORGANISM: Artificial
<220> FEATURE:
<223> OTHER INFORMATION: Description of sequence: Peptide L-TAT IB
      (generic) (see Table 1)
<220> FEATURE:
<221> NAME/KEY: VARIANT
<222> LOCATION: (1)..(40)
<223> OTHER INFORMATION: Xaa is selected from any amino acid residue
<220> FEATURE:
<221> NAME/KEY: VARIANT
<222> LOCATION: (41)..(41)
<223> OTHER INFORMATION: Xaa is selected from serine or threonine
<220> FEATURE:
<221> NAME/KEY: VARIANT
<222> LOCATION: (42)..(42)
<223> OTHER INFORMATION: Xaa is selected from any amino acid residue

<400> SEQUENCE: 24

```
Xaa Xaa Xaa Xaa Xaa Xaa Xaa Arg Lys Lys Arg Arg Gln Arg Arg Arg
1               5                   10                  15

Xaa Xaa Xaa Xaa Xaa Xaa Xaa Xaa Arg Pro Thr Thr Leu Xaa Leu Xaa
            20                  25                  30

Xaa Xaa Xaa Xaa Xaa Xaa Gln Asp Xaa Xaa
        35                  40
```

<210> SEQ ID NO 25
<211> LENGTH: 35
<212> TYPE: PRT
<213> ORGANISM: Artificial
<220> FEATURE:
<223> OTHER INFORMATION: Description of sequence: Peptide D-TAT-IB1 (see
      Table 1)
<220> FEATURE:
<221> NAME/KEY: MUTAGEN
<222> LOCATION: (1)..(35)
<223> OTHER INFORMATION: all amino acids are D-amino acids

<400> SEQUENCE: 25

```
Thr Asp Gln Ser Arg Pro Val Gln Pro Phe Leu Asn Leu Thr Thr Pro
1               5                   10                  15

Arg Lys Pro Arg Tyr Thr Asp Pro Pro Arg Arg Arg Gln Arg Arg Lys
            20                  25                  30

Lys Arg Gly
        35
```

<210> SEQ ID NO 26
<211> LENGTH: 42
<212> TYPE: PRT
<213> ORGANISM: Artificial
<220> FEATURE:
<223> OTHER INFORMATION: Description of sequence: Peptide D-TAT IB
      (generic) (see Table 1)
<220> FEATURE:
<221> NAME/KEY: MUTAGEN
<222> LOCATION: (1)..(42)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:

-continued

```
<221> NAME/KEY: VARIANT
<222> LOCATION: (2)..(2)
<223> OTHER INFORMATION: Xaa is selected from serine or threonine
<220> FEATURE:
<221> NAME/KEY: VARIANT
<222> LOCATION: (3)..(42)
<223> OTHER INFORMATION: Xaa is selected from any amino acid residue

<400> SEQUENCE: 26

Xaa Xaa Asp Gln Xaa Xaa Xaa Xaa Xaa Xaa Leu Xaa Leu Thr Thr
1               5                   10                  15

Pro Arg Xaa Xaa Xaa Xaa Xaa Xaa Xaa Arg Arg Arg Gln Arg Arg
            20                  25                  30

Lys Lys Arg Xaa Xaa Xaa Xaa Xaa Xaa Xaa
            35                  40

<210> SEQ ID NO 27
<211> LENGTH: 30
<212> TYPE: PRT
<213> ORGANISM: Artificial
<220> FEATURE:
<223> OTHER INFORMATION: Description of sequence: chimeric peptide
      sequence L-TAT-IB1(s1) (see Table 1)

<400> SEQUENCE: 27

Arg Lys Lys Arg Arg Gln Arg Arg Pro Pro Arg Pro Lys Arg Pro
1               5                   10                  15

Thr Thr Leu Asn Leu Phe Pro Gln Val Pro Arg Ser Gln Asp
            20                  25                  30

<210> SEQ ID NO 28
<211> LENGTH: 30
<212> TYPE: PRT
<213> ORGANISM: Artificial
<220> FEATURE:
<223> OTHER INFORMATION: Description of sequence: chimeric peptide
      sequence L-TAT-IB1(s2) (see Table 1)
<220> FEATURE:
<221> NAME/KEY: VARIANT
<222> LOCATION: (11)..(11)
<223> OTHER INFORMATION: Xaa is selected from glycine or proline
<220> FEATURE:
<221> NAME/KEY: REPEAT
<222> LOCATION: (11)..(11)
<223> OTHER INFORMATION: Xaa is Xnc as defined in the general formula,
      wherein n is 0-5, 5-10, 10-15, 15-20, 20-30 or more for Xnc

<400> SEQUENCE: 28

Gly Arg Lys Lys Arg Arg Gln Arg Arg Arg Xaa Arg Pro Lys Arg Pro
1               5                   10                  15

Thr Thr Leu Asn Leu Phe Pro Gln Val Pro Arg Ser Gln Asp
            20                  25                  30

<210> SEQ ID NO 29
<211> LENGTH: 29
<212> TYPE: PRT
<213> ORGANISM: Artificial
<220> FEATURE:
<223> OTHER INFORMATION: Description of sequence: chimeric peptide
      sequence L-TAT-IB1(s3) (see Table 1)
<220> FEATURE:
<221> NAME/KEY: VARIANT
<222> LOCATION: (10)..(10)
<223> OTHER INFORMATION: Xaa is selected from glycine or proline
<220> FEATURE:
<221> NAME/KEY: REPEAT
<222> LOCATION: (10)..(10)
<223> OTHER INFORMATION: Xaa is Xnc as defined in the general formula,
      wherein n is 0-5, 5-10, 10-15, 15-20, 20-30 or more for Xnc
```

```
<400> SEQUENCE: 29

Arg Lys Lys Arg Arg Gln Arg Arg Xaa Arg Pro Lys Arg Pro Thr
1               5                   10                  15

Thr Leu Asn Leu Phe Pro Gln Val Pro Arg Ser Gln Asp
                20                  25

<210> SEQ ID NO 30
<211> LENGTH: 30
<212> TYPE: PRT
<213> ORGANISM: Artificial
<220> FEATURE:
<223> OTHER INFORMATION: Description of sequence: chimeric peptide
      sequence D-TAT-IB1(s1) (see Table 1)
<220> FEATURE:
<221> NAME/KEY: MUTAGEN
<222> LOCATION: (1)..(30)
<223> OTHER INFORMATION: all amino acids are D-amino acids

<400> SEQUENCE: 30

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg
                20                  25                  30

<210> SEQ ID NO 31
<211> LENGTH: 30
<212> TYPE: PRT
<213> ORGANISM: Artificial
<220> FEATURE:
<223> OTHER INFORMATION: Description of sequence: chimeric peptide
      sequence D-TAT-IB1(s2) (see Table 1)
<220> FEATURE:
<221> NAME/KEY: MUTAGEN
<222> LOCATION: (1)..(30)
<223> OTHER INFORMATION: all amino acids are D-amino acids
<220> FEATURE:
<221> NAME/KEY: VARIANT
<222> LOCATION: (20)..(20)
<223> OTHER INFORMATION: Xaa is selected from glycine or proline
<220> FEATURE:
<221> NAME/KEY: REPEAT
<222> LOCATION: (20)..(20)
<223> OTHER INFORMATION: Xaa is Xnc as defined in the general formula,
      wherein n is 0-5, 5-10, 10-15, 15-20, 20-30 or more for Xnc

<400> SEQUENCE: 31

Asp Gln Ser Arg Pro Val Gln Pro Phe Leu Asn Leu Thr Thr Pro Arg
1               5                   10                  15

Lys Pro Arg Xaa Arg Arg Arg Gln Arg Arg Lys Lys Arg Gly
                20                  25                  30

<210> SEQ ID NO 32
<211> LENGTH: 29
<212> TYPE: PRT
<213> ORGANISM: Artificial
<220> FEATURE:
<223> OTHER INFORMATION: Description of sequence: chimeric peptide
      sequence D-TAT-IB1(s3) (see Table 1)
<220> FEATURE:
<221> NAME/KEY: MUTAGEN
<222> LOCATION: (1)..(29)
<223> OTHER INFORMATION: all amino acids are D-amino acids
<220> FEATURE:
<221> NAME/KEY: VARIANT
<222> LOCATION: (20)..(20)
<223> OTHER INFORMATION: Xaa is selected from glycine or proline
<220> FEATURE:
<221> NAME/KEY: REPEAT
<222> LOCATION: (20)..(20)
```

```
<223> OTHER INFORMATION: Xaa is Xnc as defined in the general formula,
      wherein n is 0-5, 5-10, 10-15, 15-20, 20-30 or more for Xnc

<400> SEQUENCE: 32

Asp Gln Ser Arg Pro Val Gln Pro Phe Leu Asn Leu Thr Thr Pro Arg
1               5                   10                  15

Lys Pro Arg Xaa Arg Arg Arg Gln Arg Lys Lys Arg
            20                  25

<210> SEQ ID NO 33
<211> LENGTH: 13
<212> TYPE: PRT
<213> ORGANISM: Artificial
<220> FEATURE:
<223> OTHER INFORMATION: Description of sequence: L-IB1(s1) (see Table
      1)

<400> SEQUENCE: 33

Thr Leu Asn Leu Phe Pro Gln Val Pro Arg Ser Gln Asp
1               5                   10

<210> SEQ ID NO 34
<211> LENGTH: 13
<212> TYPE: PRT
<213> ORGANISM: Artificial
<220> FEATURE:
<223> OTHER INFORMATION: Description of sequence: L-IB1(s2) (see Table
      1)

<400> SEQUENCE: 34

Thr Thr Leu Asn Leu Phe Pro Gln Val Pro Arg Ser Gln
1               5                   10

<210> SEQ ID NO 35
<211> LENGTH: 13
<212> TYPE: PRT
<213> ORGANISM: Artificial
<220> FEATURE:
<223> OTHER INFORMATION: Description of sequence: L-IB1(s3) (see Table
      1)

<400> SEQUENCE: 35

Pro Thr Thr Leu Asn Leu Phe Pro Gln Val Pro Arg Ser
1               5                   10

<210> SEQ ID NO 36
<211> LENGTH: 13
<212> TYPE: PRT
<213> ORGANISM: Artificial
<220> FEATURE:
<223> OTHER INFORMATION: Description of sequence: L-IB1(s4) (see Table
      1)

<400> SEQUENCE: 36

Arg Pro Thr Thr Leu Asn Leu Phe Pro Gln Val Pro Arg
1               5                   10

<210> SEQ ID NO 37
<211> LENGTH: 13
<212> TYPE: PRT
<213> ORGANISM: Artificial
<220> FEATURE:
<223> OTHER INFORMATION: Description of sequence: L-IB1(s5) (see Table
      1)

<400> SEQUENCE: 37

Lys Arg Pro Thr Thr Leu Asn Leu Phe Pro Gln Val Pro
```

<210> SEQ ID NO 38
<211> LENGTH: 13
<212> TYPE: PRT
<213> ORGANISM: Artificial
<220> FEATURE:
<223> OTHER INFORMATION: Description of sequence: L-IB1(s6) (see Table 1)

<400> SEQUENCE: 38

Pro Lys Arg Pro Thr Thr Leu Asn Leu Phe Pro Gln Val
1               5                   10

<210> SEQ ID NO 39
<211> LENGTH: 13
<212> TYPE: PRT
<213> ORGANISM: Artificial
<220> FEATURE:
<223> OTHER INFORMATION: Description of sequence: L-IB1(s7) (see Table 1)

<400> SEQUENCE: 39

Arg Pro Lys Arg Pro Thr Thr Leu Asn Leu Phe Pro Gln
1               5                   10

<210> SEQ ID NO 40
<211> LENGTH: 12
<212> TYPE: PRT
<213> ORGANISM: Artificial
<220> FEATURE:
<223> OTHER INFORMATION: Description of sequence: L-IB1(s8) (see Table 1)

<400> SEQUENCE: 40

Leu Asn Leu Phe Pro Gln Val Pro Arg Ser Gln Asp
1               5                   10

<210> SEQ ID NO 41
<211> LENGTH: 12
<212> TYPE: PRT
<213> ORGANISM: Artificial
<220> FEATURE:
<223> OTHER INFORMATION: Description of sequence: L-IB1(s9) (see Table 1)

<400> SEQUENCE: 41

Thr Leu Asn Leu Phe Pro Gln Val Pro Arg Ser Gln
1               5                   10

<210> SEQ ID NO 42
<211> LENGTH: 12
<212> TYPE: PRT
<213> ORGANISM: Artificial
<220> FEATURE:
<223> OTHER INFORMATION: Description of sequence: L-IB1(s10) (see Table 1)

<400> SEQUENCE: 42

Thr Thr Leu Asn Leu Phe Pro Gln Val Pro Arg Ser
1               5                   10

<210> SEQ ID NO 43
<211> LENGTH: 12
<212> TYPE: PRT
<213> ORGANISM: Artificial
<220> FEATURE:
<223> OTHER INFORMATION: Description of sequence: L-IB1(s11) (see Table

1)

<400> SEQUENCE: 43

Pro Thr Thr Leu Asn Leu Phe Pro Gln Val Pro Arg
1               5                   10

<210> SEQ ID NO 44
<211> LENGTH: 12
<212> TYPE: PRT
<213> ORGANISM: Artificial
<220> FEATURE:
<223> OTHER INFORMATION: Description of sequence: L-IB1(s12) (see Table
      1)

<400> SEQUENCE: 44

Arg Pro Thr Thr Leu Asn Leu Phe Pro Gln Val Pro
1               5                   10

<210> SEQ ID NO 45
<211> LENGTH: 12
<212> TYPE: PRT
<213> ORGANISM: Artificial
<220> FEATURE:
<223> OTHER INFORMATION: Description of sequence: L-IB1(s13) (see Table
      1)

<400> SEQUENCE: 45

Lys Arg Pro Thr Thr Leu Asn Leu Phe Pro Gln Val
1               5                   10

<210> SEQ ID NO 46
<211> LENGTH: 12
<212> TYPE: PRT
<213> ORGANISM: Artificial
<220> FEATURE:
<223> OTHER INFORMATION: Description of sequence: L-IB1(s14) (see Table
      1)

<400> SEQUENCE: 46

Pro Lys Arg Pro Thr Thr Leu Asn Leu Phe Pro Gln
1               5                   10

<210> SEQ ID NO 47
<211> LENGTH: 12
<212> TYPE: PRT
<213> ORGANISM: Artificial
<220> FEATURE:
<223> OTHER INFORMATION: Description of sequence: L-IB1(s15) (see Table
      1)

<400> SEQUENCE: 47

Arg Pro Lys Arg Pro Thr Thr Leu Asn Leu Phe Pro
1               5                   10

<210> SEQ ID NO 48
<211> LENGTH: 11
<212> TYPE: PRT
<213> ORGANISM: Artificial
<220> FEATURE:
<223> OTHER INFORMATION: Description of sequence: L-IB1(s16) (see Table
      1)

<400> SEQUENCE: 48

Asn Leu Phe Pro Gln Val Pro Arg Ser Gln Asp
1               5                   10

<210> SEQ ID NO 49

```
<211> LENGTH: 11
<212> TYPE: PRT
<213> ORGANISM: Artificial
<220> FEATURE:
<223> OTHER INFORMATION: Description of sequence: L-IB1(s17) (see Table
      1)

<400> SEQUENCE: 49

Leu Asn Leu Phe Pro Gln Val Pro Arg Ser Gln
1               5                   10

<210> SEQ ID NO 50
<211> LENGTH: 11
<212> TYPE: PRT
<213> ORGANISM: Artificial
<220> FEATURE:
<223> OTHER INFORMATION: Description of sequence: L-IB1(s18) (see Table
      1)

<400> SEQUENCE: 50

Thr Leu Asn Leu Phe Pro Gln Val Pro Arg Ser
1               5                   10

<210> SEQ ID NO 51
<211> LENGTH: 11
<212> TYPE: PRT
<213> ORGANISM: Artificial
<220> FEATURE:
<223> OTHER INFORMATION: Description of sequence: L-IB1(s19) (see Table
      1)

<400> SEQUENCE: 51

Thr Thr Leu Asn Leu Phe Pro Gln Val Pro Arg
1               5                   10

<210> SEQ ID NO 52
<211> LENGTH: 11
<212> TYPE: PRT
<213> ORGANISM: Artificial
<220> FEATURE:
<223> OTHER INFORMATION: Description of sequence: L-IB1(s20) (see Table
      1)

<400> SEQUENCE: 52

Pro Thr Thr Leu Asn Leu Phe Pro Gln Val Pro
1               5                   10

<210> SEQ ID NO 53
<211> LENGTH: 11
<212> TYPE: PRT
<213> ORGANISM: Artificial
<220> FEATURE:
<223> OTHER INFORMATION: Description of sequence: L-IB1(s21) (see Table
      1)

<400> SEQUENCE: 53

Arg Pro Thr Thr Leu Asn Leu Phe Pro Gln Val
1               5                   10

<210> SEQ ID NO 54
<211> LENGTH: 11
<212> TYPE: PRT
<213> ORGANISM: Artificial
<220> FEATURE:
<223> OTHER INFORMATION: Description of sequence: L-IB1(s22) (see Table
      1)

<400> SEQUENCE: 54
```

Lys Arg Pro Thr Thr Leu Asn Leu Phe Pro Gln
1               5                   10

<210> SEQ ID NO 55
<211> LENGTH: 11
<212> TYPE: PRT
<213> ORGANISM: Artificial
<220> FEATURE:
<223> OTHER INFORMATION: Description of sequence: L-IB1(s23) (see Table
      1)

<400> SEQUENCE: 55

Pro Lys Arg Pro Thr Thr Leu Asn Leu Phe Pro
1               5                   10

<210> SEQ ID NO 56
<211> LENGTH: 11
<212> TYPE: PRT
<213> ORGANISM: Artificial
<220> FEATURE:
<223> OTHER INFORMATION: Description of sequence: L-IB1(s24) (see Table
      1)

<400> SEQUENCE: 56

Arg Pro Lys Arg Pro Thr Thr Leu Asn Leu Phe
1               5                   10

<210> SEQ ID NO 57
<211> LENGTH: 10
<212> TYPE: PRT
<213> ORGANISM: Artificial
<220> FEATURE:
<223> OTHER INFORMATION: Description of sequence: L-IB1(s25) (see Table
      1)

<400> SEQUENCE: 57

Leu Phe Pro Gln Val Pro Arg Ser Gln Asp
1               5                   10

<210> SEQ ID NO 58
<211> LENGTH: 10
<212> TYPE: PRT
<213> ORGANISM: Artificial
<220> FEATURE:
<223> OTHER INFORMATION: Description of sequence: L-IB1(s26) (see Table
      1)

<400> SEQUENCE: 58

Asn Leu Phe Pro Gln Val Pro Arg Ser Gln
1               5                   10

<210> SEQ ID NO 59
<211> LENGTH: 10
<212> TYPE: PRT
<213> ORGANISM: Artificial
<220> FEATURE:
<223> OTHER INFORMATION: Description of sequence: L-IB1(s27) (see Table
      1)

<400> SEQUENCE: 59

Leu Asn Leu Phe Pro Gln Val Pro Arg Ser
1               5                   10

<210> SEQ ID NO 60
<211> LENGTH: 10
<212> TYPE: PRT
<213> ORGANISM: Artificial
<220> FEATURE:

```
<223> OTHER INFORMATION: Description of sequence: L-IB1(s28) (see Table
      1)

<400> SEQUENCE: 60

Thr Leu Asn Leu Phe Pro Gln Val Pro Arg
1               5                   10

<210> SEQ ID NO 61
<211> LENGTH: 10
<212> TYPE: PRT
<213> ORGANISM: Artificial
<220> FEATURE:
<223> OTHER INFORMATION: Description of sequence: L-IB1(s29) (see Table
      1)

<400> SEQUENCE: 61

Thr Thr Leu Asn Leu Phe Pro Gln Val Pro
1               5                   10

<210> SEQ ID NO 62
<211> LENGTH: 10
<212> TYPE: PRT
<213> ORGANISM: Artificial
<220> FEATURE:
<223> OTHER INFORMATION: Description of sequence: L-IB1(s30) (see Table
      1)

<400> SEQUENCE: 62

Pro Thr Thr Leu Asn Leu Phe Pro Gln Val
1               5                   10

<210> SEQ ID NO 63
<211> LENGTH: 10
<212> TYPE: PRT
<213> ORGANISM: Artificial
<220> FEATURE:
<223> OTHER INFORMATION: Description of sequence: L-IB1(s31) (see Table
      1)

<400> SEQUENCE: 63

Arg Pro Thr Thr Leu Asn Leu Phe Pro Gln
1               5                   10

<210> SEQ ID NO 64
<211> LENGTH: 10
<212> TYPE: PRT
<213> ORGANISM: Artificial
<220> FEATURE:
<223> OTHER INFORMATION: Description of sequence: L-IB1(s32) (see Table
      1)

<400> SEQUENCE: 64

Lys Arg Pro Thr Thr Leu Asn Leu Phe Pro
1               5                   10

<210> SEQ ID NO 65
<211> LENGTH: 10
<212> TYPE: PRT
<213> ORGANISM: Artificial
<220> FEATURE:
<223> OTHER INFORMATION: Description of sequence: L-IB1(s33) (see Table
      1)

<400> SEQUENCE: 65

Pro Lys Arg Pro Thr Thr Leu Asn Leu Phe
1               5                   10
```

```
<210> SEQ ID NO 66
<211> LENGTH: 10
<212> TYPE: PRT
<213> ORGANISM: Artificial
<220> FEATURE:
<223> OTHER INFORMATION: Description of sequence: L-IB1(s34) (see Table
      1)

<400> SEQUENCE: 66

Arg Pro Lys Arg Pro Thr Thr Leu Asn Leu
1               5                   10

<210> SEQ ID NO 67
<211> LENGTH: 13
<212> TYPE: PRT
<213> ORGANISM: Artificial
<220> FEATURE:
<223> OTHER INFORMATION: Description of sequence: D-IB1(s1) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 67

Gln Pro Phe Leu Asn Leu Thr Thr Pro Arg Lys Pro Arg
1               5                   10

<210> SEQ ID NO 68
<211> LENGTH: 13
<212> TYPE: PRT
<213> ORGANISM: Artificial
<220> FEATURE:
<223> OTHER INFORMATION: Description of sequence: D-IB1(s2) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 68

Val Gln Pro Phe Leu Asn Leu Thr Thr Pro Arg Lys Pro
1               5                   10

<210> SEQ ID NO 69
<211> LENGTH: 13
<212> TYPE: PRT
<213> ORGANISM: Artificial
<220> FEATURE:
<223> OTHER INFORMATION: Description of sequence: D-IB1(s3) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 69

Pro Val Gln Pro Phe Leu Asn Leu Thr Thr Pro Arg Lys
1               5                   10

<210> SEQ ID NO 70
<211> LENGTH: 13
<212> TYPE: PRT
<213> ORGANISM: Artificial
<220> FEATURE:
<223> OTHER INFORMATION: Description of sequence: D-IB1(s4) (see Table
      1)
<220> FEATURE:
<221> NAME/KEY: MUTAGEN
<222> LOCATION: (1)..(13)
<223> OTHER INFORMATION: all amino acids are D-amino acids
```

```
<400> SEQUENCE: 70

Arg Pro Val Gln Pro Phe Leu Asn Leu Thr Thr Pro Arg
1               5                   10

<210> SEQ ID NO 71
<211> LENGTH: 13
<212> TYPE: PRT
<213> ORGANISM: Artificial
<220> FEATURE:
<223> OTHER INFORMATION: Description of sequence: D-IB1(s5) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 71

Ser Arg Pro Val Gln Pro Phe Leu Asn Leu Thr Thr Pro
1               5                   10

<210> SEQ ID NO 72
<211> LENGTH: 13
<212> TYPE: PRT
<213> ORGANISM: Artificial
<220> FEATURE:
<223> OTHER INFORMATION: Description of sequence: D-IB1(s6) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 72

Gln Ser Arg Pro Val Gln Pro Phe Leu Asn Leu Thr Thr
1               5                   10

<210> SEQ ID NO 73
<211> LENGTH: 13
<212> TYPE: PRT
<213> ORGANISM: Artificial
<220> FEATURE:
<223> OTHER INFORMATION: Description of sequence: D-IB1(s7) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 73

Asp Gln Ser Arg Pro Val Gln Pro Phe Leu Asn Leu Thr
1               5                   10

<210> SEQ ID NO 74
<211> LENGTH: 12
<212> TYPE: PRT
<213> ORGANISM: Artificial
<220> FEATURE:
<223> OTHER INFORMATION: Description of sequence: D-IB1(s8) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 74

Pro Phe Leu Asn Leu Thr Thr Pro Arg Lys Pro Arg
1               5                   10
```

```
<210> SEQ ID NO 75
<211> LENGTH: 12
<212> TYPE: PRT
<213> ORGANISM: Artificial
<220> FEATURE:
<223> OTHER INFORMATION: Description of sequence: D-IB1(s9) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 75

Gln Pro Phe Leu Asn Leu Thr Thr Pro Arg Lys Pro
1               5                   10

<210> SEQ ID NO 76
<211> LENGTH: 12
<212> TYPE: PRT
<213> ORGANISM: Artificial
<220> FEATURE:
<223> OTHER INFORMATION: Description of sequence: D-IB1(s10) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 76

Val Gln Pro Phe Leu Asn Leu Thr Thr Pro Arg Lys
1               5                   10

<210> SEQ ID NO 77
<211> LENGTH: 12
<212> TYPE: PRT
<213> ORGANISM: Artificial
<220> FEATURE:
<223> OTHER INFORMATION: Description of sequence: D-IB1(s11) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 77

Pro Val Gln Pro Phe Leu Asn Leu Thr Thr Pro Arg
1               5                   10

<210> SEQ ID NO 78
<211> LENGTH: 12
<212> TYPE: PRT
<213> ORGANISM: Artificial
<220> FEATURE:
<223> OTHER INFORMATION: Description of sequence: D-IB1(s12) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 78

Arg Pro Val Gln Pro Phe Leu Asn Leu Thr Thr Pro
1               5                   10

<210> SEQ ID NO 79
<211> LENGTH: 12
<212> TYPE: PRT
<213> ORGANISM: Artificial
<220> FEATURE:
<223> OTHER INFORMATION: Description of sequence: D-IB1(s13) (see Table
      1)
```

```
<220> FEATURE:
<221> NAME/KEY: MUTAGEN
<222> LOCATION: (1)..(12)
<223> OTHER INFORMATION: all amino acids are D-amino acids

<400> SEQUENCE: 79

Ser Arg Pro Val Gln Pro Phe Leu Asn Leu Thr Thr
1               5                   10

<210> SEQ ID NO 80
<211> LENGTH: 12
<212> TYPE: PRT
<213> ORGANISM: Artificial
<220> FEATURE:
<223> OTHER INFORMATION: Description of sequence: D-IB1(s14) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 80

Gln Ser Arg Pro Val Gln Pro Phe Leu Asn Leu Thr
1               5                   10

<210> SEQ ID NO 81
<211> LENGTH: 12
<212> TYPE: PRT
<213> ORGANISM: Artificial
<220> FEATURE:
<223> OTHER INFORMATION: Description of sequence: D-IB1(s15) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 81

Asp Gln Ser Arg Pro Val Gln Pro Phe Leu Asn Leu
1               5                   10

<210> SEQ ID NO 82
<211> LENGTH: 11
<212> TYPE: PRT
<213> ORGANISM: Artificial
<220> FEATURE:
<223> OTHER INFORMATION: Description of sequence: D-IB1(s16) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 82

Phe Leu Asn Leu Thr Thr Pro Arg Lys Pro Arg
1               5                   10

<210> SEQ ID NO 83
<211> LENGTH: 11
<212> TYPE: PRT
<213> ORGANISM: Artificial
<220> FEATURE:
<223> OTHER INFORMATION: Description of sequence: D-IB1(s17) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 83
```

Pro Phe Leu Asn Leu Thr Thr Pro Arg Lys Pro
1               5                   10

<210> SEQ ID NO 84
<211> LENGTH: 11
<212> TYPE: PRT
<213> ORGANISM: Artificial
<220> FEATURE:
<223> OTHER INFORMATION: Description of sequence: D-IB1(s18) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 84

Gln Pro Phe Leu Asn Leu Thr Thr Pro Arg Lys
1               5                   10

<210> SEQ ID NO 85
<211> LENGTH: 11
<212> TYPE: PRT
<213> ORGANISM: Artificial
<220> FEATURE:
<223> OTHER INFORMATION: Description of sequence: D-IB1(s19) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 85

Val Gln Pro Phe Leu Asn Leu Thr Thr Pro Arg
1               5                   10

<210> SEQ ID NO 86
<211> LENGTH: 11
<212> TYPE: PRT
<213> ORGANISM: Artificial
<220> FEATURE:
<223> OTHER INFORMATION: Description of sequence: D-IB1(s20) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 86

Pro Val Gln Pro Phe Leu Asn Leu Thr Thr Pro
1               5                   10

<210> SEQ ID NO 87
<211> LENGTH: 11
<212> TYPE: PRT
<213> ORGANISM: Artificial
<220> FEATURE:
<223> OTHER INFORMATION: Description of sequence: D-IB1(s21) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 87

Arg Pro Val Gln Pro Phe Leu Asn Leu Thr Thr
1               5                   10

<210> SEQ ID NO 88
<211> LENGTH: 11
<212> TYPE: PRT

```
<213> ORGANISM: Artificial
<220> FEATURE:
<223> OTHER INFORMATION: Description of sequence: D-IB1(s22) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 88

Ser Arg Pro Val Gln Pro Phe Leu Asn Leu Thr
1               5                   10

<210> SEQ ID NO 89
<211> LENGTH: 11
<212> TYPE: PRT
<213> ORGANISM: Artificial
<220> FEATURE:
<223> OTHER INFORMATION: Description of sequence: D-IB1(s23) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 89

Gln Ser Arg Pro Val Gln Pro Phe Leu Asn Leu
1               5                   10

<210> SEQ ID NO 90
<211> LENGTH: 11
<212> TYPE: PRT
<213> ORGANISM: Artificial
<220> FEATURE:
<223> OTHER INFORMATION: Description of sequence: D-IB1(s24) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 90

Asp Gln Ser Arg Pro Val Gln Pro Phe Leu Asn
1               5                   10

<210> SEQ ID NO 91
<211> LENGTH: 10
<212> TYPE: PRT
<213> ORGANISM: Artificial
<220> FEATURE:
<223> OTHER INFORMATION: Description of sequence: D-IB1(s25) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 91

Asp Gln Ser Arg Pro Val Gln Pro Phe Leu
1               5                   10

<210> SEQ ID NO 92
<211> LENGTH: 10
<212> TYPE: PRT
<213> ORGANISM: Artificial
<220> FEATURE:
<223> OTHER INFORMATION: Description of sequence: D-IB1(s26) (see Table
      1)
<220> FEATURE:
<221> NAME/KEY: MUTAGEN
<222> LOCATION: (1)..(10)
```

```
<223> OTHER INFORMATION: all amino acids are D-amino acids

<400> SEQUENCE: 92

Gln Ser Arg Pro Val Gln Pro Phe Leu Asn
1               5                   10

<210> SEQ ID NO 93
<211> LENGTH: 10
<212> TYPE: PRT
<213> ORGANISM: Artificial
<220> FEATURE:
<223> OTHER INFORMATION: Description of sequence: D-IB1(s27) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 93

Ser Arg Pro Val Gln Pro Phe Leu Asn Leu
1               5                   10

<210> SEQ ID NO 94
<211> LENGTH: 10
<212> TYPE: PRT
<213> ORGANISM: Artificial
<220> FEATURE:
<223> OTHER INFORMATION: Description of sequence: D-IB1(s28) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 94

Arg Pro Val Gln Pro Phe Leu Asn Leu Thr
1               5                   10

<210> SEQ ID NO 95
<211> LENGTH: 10
<212> TYPE: PRT
<213> ORGANISM: Artificial
<220> FEATURE:
<223> OTHER INFORMATION: Description of sequence: D-IB1(s29) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 95

Pro Val Gln Pro Phe Leu Asn Leu Thr Thr
1               5                   10

<210> SEQ ID NO 96
<211> LENGTH: 10
<212> TYPE: PRT
<213> ORGANISM: Artificial
<220> FEATURE:
<223> OTHER INFORMATION: Description of sequence: D-IB1(s30) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 96

Val Gln Pro Phe Leu Asn Leu Thr Thr Pro
1               5                   10
```

```
<210> SEQ ID NO 97
<211> LENGTH: 10
<212> TYPE: PRT
<213> ORGANISM: Artificial
<220> FEATURE:
<223> OTHER INFORMATION: Description of sequence: D-IB1(s31) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 97

Gln Pro Phe Leu Asn Leu Thr Thr Pro Arg
1               5                   10

<210> SEQ ID NO 98
<211> LENGTH: 10
<212> TYPE: PRT
<213> ORGANISM: Artificial
<220> FEATURE:
<223> OTHER INFORMATION: Description of sequence: D-IB1(s32) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 98

Pro Phe Leu Asn Leu Thr Thr Pro Arg Lys
1               5                   10

<210> SEQ ID NO 99
<211> LENGTH: 10
<212> TYPE: PRT
<213> ORGANISM: Artificial
<220> FEATURE:
<223> OTHER INFORMATION: Description of sequence: D-IB1(s33) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 99

Phe Leu Asn Leu Thr Thr Pro Arg Lys Pro
1               5                   10

<210> SEQ ID NO 100
<211> LENGTH: 10
<212> TYPE: PRT
<213> ORGANISM: Artificial
<220> FEATURE:
<223> OTHER INFORMATION: Description of sequence: D-IB1(s34) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 100

Leu Asn Leu Thr Thr Pro Arg Lys Pro Arg
1               5                   10

<210> SEQ ID NO 101
<211> LENGTH: 20
<212> TYPE: DNA
<213> ORGANISM: Artificial
<220> FEATURE:
<223> OTHER INFORMATION: Primer specific for GAPDH (Forward)
```

<400> SEQUENCE: 101
atgcccccat gtttgtgatg                                                    20

<210> SEQ ID NO 102
<211> LENGTH: 2953
<212> TYPE: DNA
<213> ORGANISM: Rattus norvegicus

<400> SEQUENCE: 102

| | | | | | |
|---|---|---|---|---|---|
| ccgcccagc | tcagtccgaa | ccccgcggcg | gcggcggcct | cctccacacg | cctccacctc | 60 |
| cgccgccgcc | gccgccgccg | ccgcctcccg | cgccgctctc | cgcccggatg | gccaggctga | 120 |
| gcccgggaat | ggcggagcga | gagagcggcc | tgagcggggg | tgccgcgtcc | ccaccggccg | 180 |
| cttccccatt | cctgggactg | cacatcgcgt | cgcctcccaa | tttcaggctc | acccatgata | 240 |
| tcagcctgga | ggagtttgag | gatgaagacc | tttcggagat | cactgatgag | tgtggcatca | 300 |
| gcctgcagtg | caaagacacc | ttgtctctcc | ggccccgcg | cgccgggcta | ctgtctgcgg | 360 |
| gtagcagcgg | tagcgcgggg | agccggctgc | aggcggagat | gctgcagatg | gacctgatcg | 420 |
| acgcggcaag | tgacactccg | ggcgccgagg | acgacgaaga | ggacgacgac | gagctcgctg | 480 |
| cccaacggcc | aggagtgggg | ccttccaaag | ccgagtctgg | ccaggagccg | gcgtctcgca | 540 |
| gccagggtca | gggccagggc | cccggcacag | gctgcggaga | cacctaccgg | cccaagaggc | 600 |
| ctaccacgct | caacctttc | ccgcaggtgc | cgcggtctca | ggacacgctg | aataataact | 660 |
| ctttaggcaa | aaagcacagt | tggcaggacc | gtgtgtctcg | atcatcctcc | cctctgaaga | 720 |
| caggggagca | gacgcctcca | catgaacata | tctgcctgag | tgatgagctg | ccgccccagg | 780 |
| gcagtcctgt | tcccacccag | gatcgtggca | cttccaccga | cagcccttgt | cgccgtactg | 840 |
| cagccaccca | gatggcacct | ccaagtggtc | cccctgccac | tgcacctggt | ggccggggcc | 900 |
| actcccatcg | agatcggtcc | atatcagcag | atgtgcggct | cgaggcgact | gaggagatct | 960 |
| acctgacccc | agtgcagagg | cccccagacc | ctgcagaacc | cacctccacc | ttcttgccac | 1020 |
| ccactgagag | ccggatgtct | gtcagctcgg | atcctgaccc | tgccgcttac | tctgtaactg | 1080 |
| cagggcgacc | gcacccttcc | atcagtgaag | aggatgaggg | cttcgactgt | ctgtcatccc | 1140 |
| cagagcaagc | tgagccacca | ggtgaggggt | ggcgggaag | cctcggggag | ccaccaccgc | 1200 |
| ctccacgggc | ctcactgagc | tcggacacca | gcgcactgtc | ctacgactct | gtcaagtaca | 1260 |
| cactggtggt | ggatgagcat | gcccagcttg | agttggtgag | cctgcggcca | tgttttggag | 1320 |
| attacagtga | cgaaagcgac | tctgccactg | tctatgacaa | ctgtgcctct | gcctcctcgc | 1380 |
| cctacgagtc | agccattggt | gaggaatatg | aggaggcccc | tcaacccggg | cctcccacct | 1440 |
| gcctgtcaga | ggactccaca | ccggatgagc | ctgacgtcca | cttctctaag | aagtttctga | 1500 |
| atgtcttcat | gagtggccgc | tctcgttcct | ccagtgccga | gtcctttggg | ctgttctcct | 1560 |
| gtgtcatcaa | tggggaggag | catgagcaaa | cccatcgggc | tatattcagg | tttgtgcctc | 1620 |
| ggcatgaaga | tgaacttgag | ctggaagtgg | acgaccctct | gctggtggag | ctgcaggcag | 1680 |
| aagactattg | gtatgaggcc | tataacatgc | gcactggagc | ccgtggtgtc | tttcctgcct | 1740 |
| actatgccat | tgaggtcacc | aaggagcctg | agcacatggc | agcccttgcc | aaaaacagcg | 1800 |
| actggattga | ccagttccgg | gtgaagttcc | tgggctctgt | ccaggttcct | tatcacaagg | 1860 |
| gcaatgatgt | cctctgtgct | gctatgcaaa | agatcgccac | cacccgccgg | ctcaccgtgc | 1920 |
| actttaaccc | gccctccagc | tgtgtccttg | aaatcagcgt | taggggtgtc | aagataggtg | 1980 |

```
tcaaagctga tgaagctcag gaggccaagg gaaataaatg tagccacttt ttccagctaa    2040
aaaacatctc tttctgtggg taccatccaa agaacaacaa gtactttggg tttatcacta    2100
agcaccctgc tgaccaccgg tttgcctgcc atgtctttgt gtctgaagat tccaccaaag    2160
ccctggcaga gtctgtgggg cgtgcatttc agcagttcta caagcaattt gtggaatata    2220
cctgtcctac agaagatatc tacttggagt agcagcaacc cccctctctg cagcccctca    2280
gccccaggcc agtactagga cagctgactg ctgacaggat gttgtactgc cacgagagaa    2340
tgggggagtg agggctgttg gggtcggggg gcaggggttt ggggagaggc agatgcagtt    2400
tattgtaata tatggggtta gattaatcta tggaggacag tacaggctct ctcggggctg    2460
gggaagggca gggctggggt gggggtcagg catctggcca caagggggtc ccctagggac    2520
agaggcgctg caccatcctg gcttgtttc atactagagg ccctggcttt ctggctcttg     2580
ggtcctgcct tgacaaagcc cagccacctg gaagtgtcac cttcccttgt ccacctcacc    2640
cagtgccctg agctcatgct gagcccaagc acctccgaag gactttccag taaggaaatg    2700
gcaacatgtg acagtgagac cctgttctca tctgtgggc tccggcagct ccgaccccca     2760
gcctggccag cacgctgacc ctggcaagct tgtgtgttca agaaggaga gggccacagc     2820 aagccctgcc tgccagggaa ggttccctct cagctggccc cagccaactg gtcactgtct    2880
tgtcacctgg ctactactat taaagtgcca tttcttgtct gaaaaaaaa aaaaaaaaa     2940 aaaaaaactc gag                                                      2953
```

<210> SEQ ID NO 103
<211> LENGTH: 714
<212> TYPE: PRT
<213> ORGANISM: Rattus norvegicus

<400> SEQUENCE: 103

```
Met Ala Arg Leu Ser Pro Gly Met Ala Glu Arg Glu Ser Gly Leu Ser
1               5                   10                  15

Gly Gly Ala Ala Ser Pro Ala Ala Ser Pro Phe Leu Gly Leu His
            20                  25                  30

Ile Ala Ser Pro Pro Asn Phe Arg Leu Thr His Asp Ile Ser Leu Glu
        35                  40                  45

Glu Phe Glu Asp Glu Asp Leu Ser Glu Ile Thr Asp Glu Cys Gly Ile
    50                  55                  60

Ser Leu Gln Cys Lys Asp Thr Leu Ser Leu Arg Pro Pro Arg Ala Gly
65                  70                  75                  80

Leu Leu Ser Ala Gly Ser Ser Gly Ser Ala Gly Ser Arg Leu Gln Ala
                85                  90                  95

Glu Met Leu Gln Met Asp Leu Ile Asp Ala Ala Ser Asp Thr Pro Gly
            100                 105                 110

Ala Glu Asp Asp Glu Glu Asp Asp Glu Leu Ala Ala Gln Arg Pro
        115                 120                 125

Gly Val Gly Pro Ser Lys Ala Glu Ser Gly Gln Glu Pro Ala Ser Arg
    130                 135                 140

Ser Gln Gly Gln Gly Gln Gly Pro Gly Thr Gly Cys Gly Asp Thr Tyr
145                 150                 155                 160

Arg Pro Lys Arg Pro Thr Thr Leu Asn Leu Phe Pro Gln Val Pro Arg
                165                 170                 175

Ser Gln Asp Thr Leu Asn Asn Asn Ser Leu Gly Lys Lys His Ser Trp
            180                 185                 190

Gln Asp Arg Val Ser Arg Ser Ser Ser Pro Leu Lys Thr Gly Glu Gln
```

-continued

```
            195                 200                 205
Thr Pro Pro His Glu His Ile Cys Leu Ser Asp Glu Leu Pro Pro Gln
210                 215                 220
Gly Ser Pro Val Pro Thr Gln Asp Arg Gly Thr Ser Thr Asp Ser Pro
225                 230                 235                 240
Cys Arg Arg Thr Ala Ala Thr Gln Met Ala Pro Pro Ser Gly Pro Pro
                245                 250                 255
Ala Thr Ala Pro Gly Gly Arg Gly His Ser His Arg Asp Arg Ser Ile
        260                 265                 270
Ser Ala Asp Val Arg Leu Glu Ala Thr Glu Glu Ile Tyr Leu Thr Pro
        275                 280                 285
Val Gln Arg Pro Pro Asp Pro Ala Glu Pro Thr Ser Thr Phe Leu Pro
        290                 295                 300
Pro Thr Glu Ser Arg Met Ser Val Ser Ser Asp Pro Asp Pro Ala Ala
305                 310                 315                 320
Tyr Ser Val Thr Ala Gly Arg Pro His Pro Ser Ile Ser Glu Glu Asp
                325                 330                 335
Glu Gly Phe Asp Cys Leu Ser Ser Pro Glu Gln Ala Glu Pro Pro Gly
                340                 345                 350
Gly Gly Trp Arg Gly Ser Leu Gly Glu Pro Pro Pro Pro Arg Ala
        355                 360                 365
Ser Leu Ser Ser Asp Thr Ser Ala Leu Ser Tyr Asp Ser Val Lys Tyr
370                 375                 380
Thr Leu Val Val Asp Glu His Ala Gln Leu Glu Leu Val Ser Leu Arg
385                 390                 395                 400
Pro Cys Phe Gly Asp Tyr Ser Asp Glu Ser Asp Ser Ala Thr Val Tyr
                405                 410                 415
Asp Asn Cys Ala Ser Ala Ser Ser Pro Tyr Glu Ser Ala Ile Gly Glu
                420                 425                 430
Glu Tyr Glu Glu Ala Pro Gln Pro Arg Pro Pro Thr Cys Leu Ser Glu
        435                 440                 445
Asp Ser Thr Pro Asp Glu Pro Asp Val His Phe Ser Lys Lys Phe Leu
450                 455                 460
Asn Val Phe Met Ser Gly Arg Ser Arg Ser Ser Ser Ala Glu Ser Phe
465                 470                 475                 480
Gly Leu Phe Ser Cys Val Ile Asn Gly Glu Glu His Glu Gln Thr His
                485                 490                 495
Arg Ala Ile Phe Arg Phe Val Pro Arg His Glu Asp Glu Leu Glu Leu
                500                 505                 510
Glu Val Asp Asp Pro Leu Leu Val Glu Leu Gln Ala Glu Asp Tyr Trp
        515                 520                 525
Tyr Glu Ala Tyr Asn Met Arg Thr Gly Ala Arg Gly Val Phe Pro Ala
        530                 535                 540
Tyr Tyr Ala Ile Glu Val Thr Lys Glu Pro Glu His Met Ala Ala Leu
545                 550                 555                 560
Ala Lys Asn Ser Asp Trp Ile Asp Gln Phe Arg Val Lys Phe Leu Gly
                565                 570                 575
Ser Val Gln Val Pro Tyr His Lys Gly Asn Asp Val Leu Cys Ala Ala
                580                 585                 590
Met Gln Lys Ile Ala Thr Thr Arg Arg Leu Thr Val His Phe Asn Pro
        595                 600                 605
Pro Ser Ser Cys Val Leu Glu Ile Ser Val Arg Gly Val Lys Ile Gly
610                 615                 620
```

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
            645                 650                 655

Asn Lys Tyr Phe Gly Phe Ile Thr Lys His Pro Ala Asp His Arg Phe
        660                 665                 670

Ala Cys His Val Phe Val Ser Glu Asp Ser Thr Lys Ala Leu Ala Glu
        675                 680                 685

Ser Val Gly Arg Ala Phe Gln Gln Phe Tyr Lys Gln Phe Val Glu Tyr
        690                 695                 700

Thr Cys Pro Thr Glu Asp Ile Tyr Leu Glu
705                 710

<210> SEQ ID NO 104
<211> LENGTH: 711
<212> TYPE: PRT
<213> ORGANISM: Homo sapiens

<400> SEQUENCE: 104

Met Ala Glu Arg Glu Ser Gly Gly Leu Gly Gly Gly Ala Ala Ser Pro
1               5                   10                  15

Pro Ala Ala Ser Pro Phe Leu Gly Leu His Ile Ala Ser Pro Pro Asn
            20                  25                  30

Phe Arg Leu Thr His Asp Ile Ser Leu Glu Glu Phe Glu Asp Glu Asp
        35                  40                  45

Leu Ser Glu Ile Thr Asp Glu Cys Gly Ile Ser Leu Gln Cys Lys Asp
50                  55                  60

Thr Leu Ser Leu Arg Pro Pro Arg Ala Gly Leu Leu Ser Ala Gly Gly
65                  70                  75                  80

Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Glu Asp
            100                 105                 110

Asp Asp Glu Glu Arg Ala Ala Arg Arg Pro Gly Ala Gly Pro Pro Lys
        115                 120                 125

Ala Glu Ser Gly Gln Glu Pro Ala Ser Arg Gly Gln Gly Gln Ser Gln
    130                 135                 140

Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
                165                 170                 175

Leu Asn Asn Asn Ser Leu Gly Lys Lys His Ser Trp Gln Asp Arg Val
            180                 185                 190

Ser Arg Ser Ser Ser Pro Leu Lys Thr Gly Glu Gln Thr Pro Pro His
        195                 200                 205

Glu His Ile Cys Leu Ser Asp Glu Leu Pro Pro Gln Ser Gly Pro Ala
    210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Pro Ala Ala Pro Pro
                245                 250                 255

Gly Gly Arg Gly His Ser His Arg Asp Arg Ile His Tyr Gln Ala Asp
            260                 265                 270

Val Arg Leu Glu Ala Thr Glu Glu Ile Tyr Leu Thr Pro Val Gln Arg

```
              275                 280                 285
     Pro Pro Asp Ala Ala Glu Pro Thr Ser Ala Phe Leu Pro Pro Thr Glu
         290                 295                 300

Ser Arg Met Ser Val Ser Ser Asp Pro Asp Pro Ala Ala Tyr Pro Ser
     305                 310                 315                 320

Thr Ala Gly Arg Pro His Pro Ser Ile Ser Glu Glu Glu Glu Gly Phe
                     325                 330                 335

Asp Cys Leu Ser Ser Pro Glu Arg Ala Glu Pro Pro Gly Gly Gly Trp
                 340                 345                 350

Arg Gly Ser Leu Gly Glu Pro Pro Pro Arg Ala Ser Leu Ser
                     355                 360                 365

Ser Asp Thr Ser Ala Leu Ser Tyr Asp Ser Val Lys Tyr Thr Leu Val
         370                 375                 380

Val Asp Glu His Ala Gln Leu Glu Leu Val Ser Leu Arg Pro Cys Phe
     385                 390                 395                 400

Gly Asp Tyr Ser Asp Glu Ser Asp Ser Ala Thr Val Tyr Asp Asn Cys
                     405                 410                 415

Ala Ser Val Ser Ser Pro Tyr Glu Ser Ala Ile Gly Glu Glu Tyr Glu
                     420                 425                 430

Glu Ala Pro Arg Pro Gln Pro Pro Ala Cys Leu Ser Glu Asp Ser Thr
                 435                 440                 445

Pro Asp Glu Pro Asp Val His Phe Ser Lys Lys Phe Leu Asn Val Phe
     450                 455                 460

Met Ser Gly Arg Ser Arg Ser Ser Ser Ala Glu Ser Phe Gly Leu Phe
     465                 470                 475                 480

Ser Cys Ile Ile Asn Gly Glu Glu Gln Glu Gln Thr His Arg Ala Ile
                     485                 490                 495

Phe Arg Phe Val Pro Arg His Glu Asp Glu Leu Glu Leu Glu Val Asp
                 500                 505                 510

Asp Pro Leu Leu Val Glu Leu Gln Ala Glu Asp Tyr Trp Tyr Glu Ala
                 515                 520                 525

Tyr Asn Met Arg Thr Gly Ala Arg Gly Val Phe Pro Ala Tyr Tyr Ala
         530                 535                 540

Ile Glu Val Thr Lys Glu Pro Glu His Met Ala Ala Leu Ala Lys Asn
     545                 550                 555                 560

Ser Asp Trp Val Asp Gln Phe Arg Val Lys Phe Leu Gly Ser Val Gln
                     565                 570                 575

Val Pro Tyr His Lys Gly Asn Asp Val Leu Cys Ala Ala Met Gln Lys
                 580                 585                 590

Ile Ala Thr Thr Arg Arg Leu Thr Val His Phe Asn Pro Pro Ser Ser
                     595                 600                 605

Cys Val Leu Glu Ile Ser Val Arg Gly Val Lys Ile Gly Val Lys Ala
                 610                 615                 620

Asp Asp Ser Gln Glu Ala Lys Gly Asn Lys Cys Ser His Phe Phe Gln
     625                 630                 635                 640

Leu Lys Asn Ile Ser Phe Cys Gly Tyr His Pro Lys Asn Asn Lys Tyr
                     645                 650                 655

Phe Gly Phe Ile Thr Lys His Pro Ala Asp His Arg Phe Ala Cys His
                     660                 665                 670

Val Phe Val Ser Glu Asp Ser Thr Lys Ala Leu Ala Glu Ser Val Gly
                 675                 680                 685

Arg Ala Phe Gln Gln Phe Tyr Lys Gln Phe Val Glu Tyr Thr Cys Pro
                 690                 695                 700
```

Thr Glu Asp Ile Tyr Leu Glu
705                 710

<210> SEQ ID NO 105
<211> LENGTH: 2136
<212> TYPE: DNA
<213> ORGANISM: Homo sapiens

<400> SEQUENCE: 105

| | | | | | |
|---|---|---|---|---|---|
| atggcggagc | gagaaagcgg | cggcctggga | gggggggccg | cgtccccgcc | cgccgcctcc | 60
| ccgttcctgg | ggctgcacat | cgcttcgcct | cccaatttca | ggctcaccca | tgacatcagc | 120
| ctggaggagt | ttgaggatga | agacctctcg | agatcactg | atgagtgtgg | catcagctta | 180
| cagtgcaaag | acaccctgtc | cttacggcc | ccgcgcgccg | ggctgctctc | tgcgggcggc | 240
| ggcggcgcgg | ggagccggtt | gcaggccgag | atgctgcaga | tggacctgat | cgacgcgacg | 300
| ggggacactc | ccggggccga | ggacgacgag | gaggacgacg | acgaggagcg | cgcggcccgg | 360
| cggccgggag | cggggccgcc | caaggccgag | tccggccagg | agccggcgtc | ccgcggccag | 420
| ggccagagcc | aaggccagag | ccagggcccg | ggcagcgggg | acacgtaccg | gccaagcgg | 480
| cccaccacgc | tcaacctctt | tccgcaggtg | ccgcggtctc | aggacacact | gaataataat | 540
| tctctgggca | aaaagcacag | ttggcaggat | cgggtgtctc | gatcatcctc | acccctgaag | 600
| acaggggagc | agacaccacc | gcatgaacac | atctgcctga | gcgatgagct | gccccccag | 660
| agcggccccg | cccccaccac | agatcgaggc | acctccaccg | acagcccttg | ccgccgcagc | 720
| acagccaccc | agatggcacc | tccgggtggt | cccctgctg | cccgcctgg | ggtcggggc | 780
| cactcgcatc | gagaccgaat | ccactaccag | gccgatgtgc | gactagaggc | cactgaggag | 840
| atctacctga | cccagtgca | gaggccccca | gacgctgcag | agcccactc | cgccttcctg | 900
| ccgcccactg | agagccggat | gtcagtcagc | tccgatccag | accctgccgc | ctacccctcc | 960
| acggcagggc | ggccgcaccc | ctccatcagt | gaagaggaag | agggcttcga | ctgcctgtcg | 1020
| tccccagagc | gggctgagcc | ccaggcggga | gggtggcggg | ggagcctggg | ggagccgccg | 1080
| ccacctccac | gggcctctct | gagctcggac | accagcgccc | tgtcctatga | ctctgtcaag | 1140
| tacacgctgg | tggtagatga | gcatgcacag | ctggagctgg | tgagcctgcg | gccgtgcttc | 1200
| ggagactaca | gtgacgagag | tgactctgcc | accgtctatg | acaactgtgc | ctccgtctcc | 1260
| tcgccctatg | agtcggccat | cggagaggaa | tatgaggagg | cccgcggcc | ccagcccct | 1320
| gcctgcctct | ccgaggactc | cacgcctgat | gaacccgacg | tccatttctc | caagaaattc | 1380
| ctgaacgtct | tcatgagtgg | ccgctcccgc | tcctccagtg | ctgagtcctt | cgggctgttc | 1440
| tcctgcatca | tcaacgggga | ggagcaggag | cagacccacc | gggccatatt | caggtttgtg | 1500
| cctcgacacg | aagacgaact | tgagctggaa | gtggatgacc | ctctgctagt | ggagctccag | 1560
| gctgaagact | actggtacga | ggcctacaac | atgcgcactg | gtgccgggg | tgtctttcct | 1620
| gcctattacg | ccatcgaggt | caccaaggag | cccgagcaca | tggcagccct | ggccaaaaac | 1680
| agtgactggg | tggaccagtt | ccgggtgaag | ttcctgggct | cagtccaggt | tccctatcac | 1740
| aagggcaatg | acgtcctctg | tgctgctatg | caaaagattg | ccaccacccg | ccggctcacc | 1800
| gtgcacttta | acccgccctc | cagctgtgtc | ctggagatca | gcgtgcgggg | tgtgaagata | 1860
| ggcgtcaagg | ccgatgactc | ccaggaggcc | aagggggaata | aatgtagcca | cttttttccag | 1920
| ttaaaaaaca | tctctttctg | cggatatcat | ccaaagaaca | caagtacttt | ggggttcatc | 1980
| accaagcacc | ccgccgacca | ccggtttgcc | tgccacgtct | ttgtgtctga | agactccacc | 2040

```
aaagccctgg cagagtccgt ggggagagca ttccagcagt tctacaagca gtttgtggag    2100
tacacctgcc ccacagaaga tatctacctg gagtag                              2136

<210> SEQ ID NO 106
<211> LENGTH: 20
<212> TYPE: DNA
<213> ORGANISM: Artificial Sequence
<220> FEATURE:
<223> OTHER INFORMATION: Primer specific for GAPDH (Reverse)

<400> SEQUENCE: 106
atggcatgga ctgtggtcat                                                  20

<210> SEQ ID NO 107
<211> LENGTH: 26
<212> TYPE: DNA
<213> ORGANISM: Artificial Sequence
<220> FEATURE:
<223> OTHER INFORMATION: Primier specific for iNOS (Forward)

<400> SEQUENCE: 107
tttctcttca aagtcaaatc ctacca                                           26

<210> SEQ ID NO 108
<211> LENGTH: 23
<212> TYPE: DNA
<213> ORGANISM: Artificial Sequence
<220> FEATURE:
<223> OTHER INFORMATION: Primer specific for iNOS (Reverse)

<400> SEQUENCE: 108
tgtgtctgca gatgtgctga aac                                              23
```

USE OF CELL-PERMEABLE PEPTIDE INHIBITORS OF THE JNK SIGNAL TRANSDUCTION PATHWAY FOR THE TREATMENT OF CHRONIC OR NON-CHRONIC INFLAMMATORY EYE DISEASES

SEQUENCE LISTING SUBMISSION VIA EFS-WEB

A computer readable text file, entitled "067802-5030-01_SequenceListing.txt," created on or about 3 Sep. 2015, with a file size of about 62 kb contains the sequence listing for this application and is hereby incorporated by reference in its entirety.

The present invention refers to the use of protein kinase inhibitors and more specifically to the use of inhibitors of the protein kinase c-Jun amino terminal kinase, JNK inhibitor (poly-)peptides, chimeric peptides, or of nucleic acids encoding same as well as pharmaceutical compositions containing same, for the treatment of non-chronic or chronic inflammatory eye diseases, such as hordeolum, chalazion, conjunktivitis, keratitis, scleritis, episcleritis, endophthalmitis, panophtalmitis, irititis, uveitis, cyclitis, chorioiditis, orbital phlegmon, and/or myositis of the eye muscle, etc.

The number of ophthalmological (eye) diseases, particularly of non-chronic and chronic ophthalmological (eye) diseases represents a considerable challenge for the public health care systems. Ophthalmological diseases are diseases that pertain to the eye. The present invention focuses on non-chronic or chronic inflammatory eye diseases. These include for example inflammatory diseases of the blephara, conjunctiva, cornea, sclera, the vitreous body, uvea, ciliary body, choroid, orbital bone, lacrimal gland, iris, etc. Examples of such inflammatory diseases are hordeolum, chalazion, conjunktivitis, keratitis, scleritis, episcleritis, endophthalmitis, panophtalmitis, irititis, uveitis, cyclitis, chorioiditis, orbital phlegmon, and/or myositis of the eye muscle.

The c-Jun NH2-terminal kinases (JNKs) have been identified as stress-activated protein kinases that phosphorylate c-Jun on two sites in its NH2-terminal activation domain. The JNK pathway is activated by certain cytokines, mitogens, osmotic stress and irradiation. The phosphorylation of the c-Jun component of the activator protein AP-1 transcription factor results in pro-inflammatory cytokines production. During inflammation, leukocytes infiltration and rolling result from the early activation of the vascular endothelium that releases important chemotactic factors such as RANTES, IL-8, ICAM and VCAM. Infiltrating cells in turn release distinct sets of pro- or anti-inflammatory products that contribute to tissue damages and inflammation. Many of the gene products involved in the inflammatory response are regulated by the transcription factor activator protein-1 (AP-1), and the c-Jun NH2-terminal kinase (JNK) pathway: COX-2, cyclooxygenase-2; IFN-g, interferon-gamma; iNOS, inducible nitric oxide synthase; TNF-a, tumor-necrosis factor-alpha; MCP-1, membrane cofactor protein-1; MIP-1, major intrinsic protein-1; IL-2, interleukin-2, .... In lipopolysaccharide (LPS)-stimulated monocytes and tissue macrophages, TNF-a is produced through the JNK pathway activation and modulated by its inhibition.

JNK inhibitors have been therefore used in various models of inflammation and shown to exert anti-inflammatory and beneficial effects in inflammatory diseases such arthritis and asthma.

The object of the present invention is thus to provide alternative or improved therapies, which allow new and preferably improved cure of non-chronic or chronic (inflammatory) eye diseases, such as hordeolum, chalazion, conjunktivitis, keratitis, scleritis, episcleritis, endophthalmitis, panophtalmitis, irititis, uveitis, cyclitis, chorioiditis, orbital phlegmon, myositis of the eye muscle, etc.

This object is solved by the use of a JNK inhibitor (poly-)peptide comprising less than 150 amino acids in length for the preparation of a pharmaceutical composition for treating non-chronic or chronic inflammatory eye diseases in a subject.

The term "non-chronic or chronic inflammatory eye disease" as used herein typically denotes non-chronic or chronic inflammatory diseases that pertain to the eye. This includes diseases of the blephara, conjunctiva, cornea, sclera, the vitreous body, uvea, ciliary body, choroid, orbital bone, lacrimal gland, iris, etc. Preferably included in this respect are hordeolum, chalazion, conjunktivitis, keratitis, scleritis, episcleritis, endophthalmitis, panophtalmitis, irititis, uveitis, cyclitis, chorioiditis, orbital phlegmon, myositis of the eye muscle. Particularly preferred in the context of the present invention is the treatment of uveitis, for example treatment of anterior uveitis, intermediate uveitis, posterior uveitis and panuveitis.

The present inventors surprisingly found, that JNK inhibitor (poly-)peptides s are particularly suitable for treating such chronic or non-chronic inflammatory eye diseases in a subject. This was neither obvious nor suggested by the prior art, even though JNK inhibitor (poly-)peptides in general have been known from the art.

In the context of the present invention, a JNK inhibitor (poly-)peptide may be typically derived from a human or rat IB1 sequence, preferably from an amino acid sequence as defined or encoded by any of sequences according to SEQ ID NO: 102 (depicts the IB1 cDNA sequence from rat and its predicted amino acid sequence), SEQ ID NO: 103 (depicts the IB1 protein sequence from rat encoded by the exon-intron boundary of the rIB1 gene-splice donor), SEQ ID NO: 104 (depicts the IB1 protein sequence from *Homo sapiens*), or SEQ ID NO: 105 (depicts the IB1 cDNA sequence from *Homo sapiens*), more preferably from an amino acid sequence as defined or encoded by any of sequences according to SEQ ID NO: 104 (depicts the IB1 protein sequence from *Homo sapiens*), or SEQ ID NO: 105 (depicts the IB1 cDNA sequence from *Homo sapiens*), or from any fragments or variants thereof. In other words, the JNK inhibitor (poly-)peptide comprises a fragment, variant, or variant of such fragment of a human or rat IB1 sequence. Human or rat IB sequences are defined or encoded, respectively, by the sequences according to SEQ ID NO: 102, SEQ ID NO: 103, SEQ ID NO: 104 or SEQ ID NO: 105.

Preferably, such a JNK inhibitor (poly-)peptide as used herein comprises a total length of less than 150 amino acid residues, preferably a range of 5 to 150 amino acid residues, more preferably 10 to 100 amino acid residues, even more preferably 10 to 75 amino acid residues and most preferably a range of 10 to 50 amino acid residues, e.g. 10 to 30, 10 to 20, or 10 to 15 amino acid residues.

More preferably, such a JNK inhibitor (poly-)peptide and the above ranges may be selected from any of the above mentioned sequences, even more preferably from an amino acid sequence as defined according to SEQ ID NO: 104 or as encoded by SEQ ID NO: 105, even more preferably in the region between nucleotides 420 and 980 of SEQ ID NO: 105 or amino acids 105 and 291 of SEQ ID NO: 104, and most preferably in the region between nucleotides 561 and 647 of SEQ ID NO: 105 or amino acids 152 and 180 of SEQ ID NO: 104.

According to a particular embodiment, a JNK inhibitor (poly-)peptide as used herein typically binds JNK and/or inhibits the activation of at least one JNK activated transcription factor, e.g. c-Jun or ATF2 (see e.g. SEQ ID NOs: 15 and 16, respectively) or Elk1.

Likewise, the JNK inhibitor (poly-)peptide as used herein preferably comprises or consists of at least one amino acid sequence according to any one of SEQ ID NOs: 1 to 4, 13 to 20 and 33 to 100, or a fragment, derivative or variant thereof. More preferably, the JNK inhibitor (poly-) peptide as used herein may contain 1, 2, 3, 4 or even more copies of an amino acid sequence according to SEQ ID NOs: 1 to 4, 13 to 20 and 33 to 100, or a variant, fragment or derivative thereof. If present in more than one copy, these amino acid sequences according to SEQ ID NOs: 1 to 4, 13 to 20 and 33 to 100, or variants, fragments, or derivatives thereof as used herein may be directly linked with each other without any linker sequence or via a linker sequence comprising 1 to 10, preferably 1 to 5 amino acids. Amino acids forming the linker sequence are preferably selected from glycine or proline as amino acid residues. More preferably, these amino acid sequences according to SEQ ID NOs: 1 to 4, 13 to 20 and 33 to 100, or fragments, variants or derivatives thereof, as used herein, may be separated by each other by a hinge of two, three or more proline residues.

The JNK inhibitor (poly-)peptides as used herein may be composed of L-amino acids, D-amino acids, or a combination of both. Preferably, the JNK inhibitor (poly-)peptides as used herein comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK inhibitor sequences as used herein in a blockwise, a non-blockwise or in an alternate manner.

According to one preferred embodiment the JNK inhibitor (poly-)peptides as used herein may be exclusively composed of L-amino acids. The JNK inhibitor (poly-)peptides as used herein may then comprise or consist of at least one native JNK inhibitor sequence" according to SEQ ID NO: 1 or 3. In this context, the term "native" or "native JNK inhibitor sequence(s)" is referred to non-altered JNK inhibitor (poly-) peptide sequences according to any of SEQ ID NOs: 1 or 3, as used herein, entirely composed of L-amino acids.

Accordingly, the JNK inhibitor (poly-)peptide as used herein may comprise or consist of at least one (native) amino acid sequence $NH_2$—$X_n^b$—$X_n^a$-RPTTLXLXXXXX-XXQD-$X_n^b$—COOH (L-IB generic (s)) [SEQ ID NO: 3] and/or the JNK binding domain (JBDs) of IB1 XRPT-TLXLXXXXXXXQDS/TX (L-IB (generic)) [SEQ ID NO: 19]. In this context, each X typically represents an amino acid residue, preferably selected from any (native) amino acid residue. $X_n^a$ typically represents one amino acid residue, preferably selected from any amino acid residue except serine or threonine, wherein n (the number of repetitions of X) is 0 or 1. Furthermore, each $X_n^b$ may be selected from any amino acid residue, wherein n (the number of repetitions of X) is 0-5, 5-10, 10-15, 15-20, 20-30 or more, provided that if n (the number of repetitions of X) is 0 for $X_n^a$, $X_n^b$ does preferably not comprise a serine or threonine at its C-terminus, in order to avoid a serine or threonine at this position. Preferably, $X_n^b$ represents a contiguous stretch of peptide residues derived from SEQ ID NO: 1 or 3. $X_n^a$ and $X_n^b$ may represent either D or L amino acids. Additionally, the JNK inhibitor (poly-)peptide as used herein may comprise or consist of at least one (native) amino acid sequence selected from the group comprising the JNK binding domain of IB1 DTYRPKRPTTLNLFPQVPRSQDT (L-IB1) [SEQ ID NO: 17]. More preferably, the JNK inhibitor (poly-) peptide as used herein further may comprise or consist of at least one (native) amino acid sequence $NH_2$—RPKRPT-TLNLFPQVPRSQD-COOH (L-IB1(s)) [SEQ ID NO: 1]. Furthermore, the JNK inhibitor (poly-)peptide as used herein may comprise or consist of at least one (native) amino acid sequence selected from the group comprising the JNK binding domain of IB1 L-IB1(s1) ($NH_2$-TLNLFPQVPR-SQD-COOH, SEQ ID NO: 33); L-IB1(s2) ($NH_2$-TTLNLFPQVPRSQ-COOH, SEQ ID NO: 34); L-IB1(s3) ($NH_2$-PTTLNLFPQVPRS—COOH, SEQ ID NO: 35); L-IB1(s4) ($NH_2$—RPTTLNLFPQVPR—COOH, SEQ ID NO: 36); L-IB1(s5) ($NH_2$—KRPTTLNLFPQVP—COOH, SEQ ID NO: 37); L-IB1(s6) ($NH_2$—PKRPTTLNLFPQV—COOH, SEQ ID NO: 38); L-IB1(s7) ($NH_2$—RPKRPT-TLNLFPQ-COOH, SEQ ID NO: 39); L-IB1(s8) ($NH_2$-LNLFPQVPRSQD-COOH, SEQ ID NO: 40); L-IB1(s9) ($NH_2$-TLNLFPQVPRSQ-COOH, SEQ ID NO: 41); L-IB1 (s10) ($NH_2$-TTLNLFPQVPRS—COOH, SEQ ID NO: 42); L-IB1(s11) ($NH_2$-PTTLNLFPQVPR—COOH, SEQ ID NO: 43); L-IB1(s12) ($NH_2$—RPTTLNLFPQVP—COOH, SEQ ID NO: 44); L-IB1(s13) ($NH_2$-KRPTTLNLFPQV—COOH, SEQ ID NO: 45); L-IB1(s14) ($NH_2$-PKRPT-TLNLFPQ-COOH, SEQ ID NO: 46); L-IB1(s15) ($NH_2$—RPKRPTTLNLFP—COOH, SEQ ID NO: 47); L-IB1(s16) ($NH_2$-NLFPQVPRSQD-COOH, SEQ ID NO: 48); L-IB1 (s17) ($NH_2$-LNLFPQVPRSQ-COOH, SEQ ID NO: 49); L-IB1(s18) ($NH_2$-TLNLFPQVPRS—COOH, SEQ ID NO: 50); L-IB1(s19) ($NH_2$-TTLNLFPQVPR—COOH, SEQ ID NO: 51); L-IB1(s20) PTTLNLFPQVP—COOH, SEQ ID NO: 52); L-IB1(s21) ($NH_2$—RPTTLNLFPQV—COOH, SEQ ID NO: 53); L-IB1(s22) ($NH_2$—KRPTTLNLFPQ-COOH, SEQ ID NO: 54); L-IB1(s23) ($NH_2$-PKRPT-TLNLFP—COOH, SEQ ID NO: 55); L-IB1(s24) ($NH_2$—RPKRPTTLNLF—COOH, SEQ ID NO: 56); L-IB1(s25) ($NH_2$-LFPQVPRSQD-COOH, SEQ ID NO: 57); L-IB1 (s26) ($NH_2$-NLFPQVPRSQ-COOH, SEQ ID NO: 58); L-IB1(s27) ($NH_2$-LNLFPQVPRS—COOH, SEQ ID NO: 59); L-IB1(s28) ($NH_2$-TLNLFPQVPR—COOH, SEQ ID NO: 60); L-IB1(s29) ($NH_2$-TTLNLFPQVP—COOH, SEQ ID NO: 61); L-IB1(s30) ($NH_2$-PTTLNLFPQV—COOH, SEQ ID NO: 62); L-IB1(s31) ($NH_2$—RPTTLNLFPQ-COOH, SEQ ID NO: 63); L-IB1(s32) ($NH_2$—KRPT-TLNLFP—COOH, SEQ ID NO: 64); L-IB1(s33) ($NH_2$-PKRPTTLNLF—COOH, SEQ ID NO: 65); and L-IB1(s34) ($NH_2$—RPKRPTTLNL-COOH, SEQ ID NO: 66).

Additionally, the JNK inhibitor (poly-)peptide as used herein may comprise or consist of at least one (native) amino acid sequence selected from the group comprising the (long) JNK binding domain (JBDs) of IB1 PGTGCGD-TYRPKRPTTLNLFPQVPRSQDT (IB1-long) [SEQ ID NO: 13], the (long) JNK binding domain of IB2 IPSPS-VEEPHKHRPTTLRLTTLGAQDS (IB2-long) [SEQ ID NO: 14], the JNK binding domain of c-Jun GAYGYSNP-KILKQSMTLNLADPVGNLKPH (c-Jun) [SEQ ID NO: 15], the JNK binding domain of ATF2 TNEDHLAVHKHKHEMTLKFGPARNDSVIV (ATF2) [SEQ ID NO: 16] (see e.g. FIGS. 1A-1C). In this context, an alignment revealed a partially conserved 8 amino acid sequence (see e.g. FIG. 1A) and a further comparison of the JBDs of IB1 and IB2 revealed two blocks of seven and three amino acids that are highly conserved between the two sequences.

According to another preferred embodiment the JNK inhibitor (poly-)peptides as used herein may be composed in part or exclusively of D-amino acids as defined above. More preferably, these JNK inhibitor (poly-)peptides composed of D-amino acids are non-native D retro-inverso sequences of the above (native) JNK inhibitor sequences. The term "retro-inverso (poly-) peptides" refers to an isomer of a linear peptide sequence in which the direction of the sequence is reversed and the chirality of each amino acid residue is inverted (see e.g. Jameson et al., Nature, 368,744-746 (1994); Brady et al., Nature, 368,692-693 (1994)). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or peptide as used according to the present invention may be converted into an D retro-inverso sequence or peptide by synthesizing a reverse of the sequence or peptide for the corresponding native L-amino acid sequence or peptide.

The D retro-inverso (poly-)peptides as used herein and as defined above have a variety of useful properties. For example, D retro-inverso (poly-)peptides as used herein enter cells as efficiently as L-amino acid sequences as used herein, whereas the D retro-inverso sequences as used herein are more stable than the corresponding L-amino acid sequences.

Accordingly, the JNK inhibitor (poly-)peptides as used herein may comprise or consist of at least one D retro-inverso sequence according to the amino acid sequence $NH_2—X_n^b$-DQXXXXXXXXLXLTTPR—$X_n^a$—$X_n^b$—COOH (D-IB1 generic (s)) [SEQ ID NO: 4] and/or XS/TDQXXXXXXXXLXLTTPRX (D-IB (generic)) [SEQ ID NO: 20]. As used in this context, X, $X_n^a$ and $X_n^b$ are as defined above (preferably, representing D amino acids), wherein $X_n^b$ preferably represents a contiguous stretch of residues derived from SEQ ID NO: 2 or 4. Additionally, the JNK inhibitor (poly-)peptides as used herein may comprise or consist of at least one D retro-inverso sequence according to the amino acid sequence comprising the JNK binding domain (JBDs) of IB1 TDQSRPVQPFLNLTTPRKPRYTD (D-IB1) [SEQ ID NO: 18]. More preferably, the JNK inhibitor (poly-)peptides as used herein may comprise or consist of at least one D retro-inverso sequence according to the amino acid sequence $NH_2$-DQSRPVQPFLNLTTPRKPR—COOH (D-IB1(s)) [SEQ ID NO: 2]. Furthermore, the JNK inhibitor (poly-)peptides as used herein may comprise or consist of at least one D retro-inverso sequence according to the amino acid sequence comprising the JNK binding domain (JBDs) of IB1 D-IB1(s1) ($NH_2$-QPFLNLTTPRKPR—COOH, SEQ ID NO: 67); D-IB1(s2) ($NH_2$—VQPFLNLTTPRKP—COOH, SEQ ID NO: 68); D-IB1(s3) ($NH_2$—PVQPFLNLTTPRK—COOH, SEQ ID NO: 69); D-IB1(s4) ($NH_2$—RPVQPFLNLTTPR—COOH, SEQ ID NO: 70); D-M1(s5) ($NH_2$—SRPVQPFLNLTTP—COOH, SEQ ID NO: 71); D-IB1(s6) ($NH_2$-QSRPVQPFLNLTT-COOH, SEQ ID NO: 72); D-IB1(s7) ($NH_2$-DQSRPVQPFLNLT-COOH, SEQ ID NO: 73); D-IB1(s8) ($NH_2$—PFLNLTTPRKPR—COOH, SEQ ID NO: 74); D-IB1(s9) ($NH_2$-QPFLNLTTPRKP—COOH, SEQ ID NO: 75); D-IB1(s10) ($NH_2$—VQPFLNLTTPRK—COOH, SEQ ID NO: 76); D-IB1(s11) ($NH_2$—PVQPFLNLTTPR—COOH, SEQ ID NO: 77); D-IB1(s12) ($NH_2$—RPVQPFLNLTTP—COOH, SEQ ID NO: 78); D-IB1(s13) ($NH_2$—SRPVQPFLNLTT-COOH, SEQ ID NO: 79); D-IB1(s14) ($NH_2$-QSRPVQPFLNLT-COOH, SEQ ID NO: 80); D-IB1(s15) ($NH_2$-DQSRPVQPFLNL-COOH, SEQ ID NO: 81); D-IB1(s16) ($NH_2$—FLNLTTPRKPR—COOH, SEQ ID NO: 82); D-IB1(s17) ($NH_2$—PFLNLTTPRKP—COOH, SEQ ID NO: 83); D-IB1(s18) ($NH_2$-QPFLNLTTPRK—COOH, SEQ ID NO: 84); D-IB1(s19) ($NH_2$—VQPFLNLTTPR—COOH, SEQ ID NO: 85); D-IB1(s20) ($NH_2$—PVQPFLNLTTP—COOH, SEQ ID NO: 86); D-IB1(s21) ($NH_2$—RPVQPFLNLTT-COOH, SEQ ID NO: 87); D-IB1(s22) ($NH_2$—SRPVQPFLNLT-COOH, SEQ ID NO: 88); D-IB1(s23) ($NH_2$-QSRPVQPFLNL-COOH, SEQ ID NO: 89); D-IB1(s24) ($NH_2$-DQSRPVQPFLN—COOH, SEQ ID NO: 90); D-IB1(s25) ($NH_2$-DQSRPVQPFL-COOH, SEQ ID NO: 91); D-IB1(s26) ($NH_2$-QSRPVQPFLN-COOH, SEQ ID NO: 92); D-M1(s27) ($NH_2$—SRPVQPFLNL-COOH, SEQ ID NO: 93); D-IB1(s28) ($NH_2$—RPVQPFLNLT-COOH, SEQ ID NO: 94); D-IB1(s29) ($NH_2$—PVQPFLNLTT-COOH, SEQ ID NO: 95); D-IB1(s30) ($NH_2$—VQPFLNLTTP—COOH, SEQ ID NO: 96); D-IB1(s31) ($NH_2$-QPFLNLTTPR—COOH, SEQ ID NO: 97); D-IB1(s32) ($NH_2$—PFLNLTTPRK—COOH, SEQ ID NO: 98); D-IB1(s33) ($NH_2$—FLNLTTPRKP—COOH, SEQ ID NO: 99); and D-IB1(s34) ($NH_2$-LNLTTPRKPR—COOH, SEQ ID NO: 100).

The JNK inhibitor (poly-)peptides as used herein and as disclosed above are presented in Table 1 (SEQ ID NO:s 1-4, 13-20 and 33-100). The table presents the name of the JNK inhibitor (poly-) peptides/sequences as used herein, as well as their sequence identifier number, their length, and amino acid sequence. Furthermore, Table 1 shows sequences as well as their generic formulas, e.g. for SEQ ID NO's: 1, 2, 5, 6, 9 and 11 and SEQ ID NO's: 3, 4, 7, 8, 10 and 12, respectively. Table 1 furthermore discloses the chimeric sequences SEQ ID NOs: 9-12 and 23-32 (see below), L-IB1 sequences SEQ ID NOs: 33 to 66 and D-IB1 sequences SEQ ID NOs: 67 to 100.

TABLE 1

| SEQUENCE/PEPTIDE NAME | SEQ ID NO | AA | SEQUENCE |
| --- | --- | --- | --- |
| L-IB$_1$(s) | 1 | 19 | RPKRPTTLNLFPQVPRSQD ($NH_2$-RPKRPTTLNLFPQVPRSQD-COOH) |
| D-IB$_1$(s) | 2 | 19 | DQSRPVQPFLNLTTPRKPR ($NH_2$-DQSRPVQPFLNLTTPRKPR-COOH) |
| L-IB(generic)(s) | 3 | 19 | $NH_2$-$X_n^b$-$X_n^a$-RPTTLXLXXXXXXXXQD-$X_n^b$-COOH |
| D-IB(generic)(s) | 4 | 19 | $NH_2$-$X_n^b$-DQXXXXXXXXLXLTTPR-$X_n^a$-$X_n^b$-COOH |
| L-TAT | 5 | 10 | GRKKRRQRRR ($NH_2$-GRKKRRQRRR-COOH) |

TABLE 1-continued

| SEQUENCE/PEPTIDE NAME | SEQ ID NO | AA | SEQUENCE |
| --- | --- | --- | --- |
| D-TAT | 6 | 10 | RRRQRRKKRG<br>(NH$_2$-RRRQRRKKRG-COOH) |
| L-generic-TAT(s) | 7 | 11 | NH$_2$-X$_n^b$-RKKRRQRRR-X$_n^b$-COOH |
| D-generic-TAT(s) | 8 | 11 | NH$_2$-X$_n^b$-RRRQRRKKR-X$_n^b$-COOH |
| L-TAT-IB$_1$(s) | 9 | 31 | GRKKRRQRRRPPRPKRPTTLNLFPQVPRSQD<br>(NH$_2$-GRKKRRQRRRPPRPKRPTTLNLFPQVPRSQD-COOH) |
| L-TAT-IB(generic)(s) | 10 | 29 | NH$_2$-X$_n^b$-RKKRRQRRR-X$_n^b$-X$_n^a$-RPTTLXLXXXXXXXQD-X$_n^b$-COOH |
| D-TAT-IB$_1$(s) | 11 | 31 | DQSRPVQPFLNLTTPRKPRPPRRRQRRKKRG<br>(NH$_2$-DQSRPVQPFLNLTTPRKPRPPRRRQRRKKRG-COOH) |
| D-TAT-IB(generic)(s) | 12 | 29 | (NH$_2$-X$_n^b$-DQXXXXXXXLXLTTPR-X$_n^a$-X$_n^b$-RRRQRRKKR-X$_n^b$-COOH) |
| IB1-long | 13 | 29 | PGTGCGDTYRPKRPTTLNLFPQVPRSQDT<br>(NH$_2$-PGTGCGDTYRPKRPTTLNLFPQVPRSQDT-COOH) |
| IB2-long | 14 | 27 | IPSPSVEEPHKHRPTTLRLTTLGAQDS<br>(NH$_2$-IPSPSVEEPHKHRPTTLRLTTLGAQDS-COOH) |
| c-Jun | 15 | 29 | GAYGYSNPKILKQSMTLNLADPVGNLKPH<br>(NH$_2$-GAYGYSNPKILKQSMTLNLADPVGNLKPH-COOH) |
| ATF$_2$ | 16 | 29 | TNEDHLAVHKHKHEMTLKFGPARNDSVIV<br>(NH$_2$-TNEDHLAVHKHKHEMTLKFGPARNDSVIV-COOH) |
| L-IB$_1$ | 17 | 23 | DTYRPKRPTTLNLFPQVPRSQDT<br>(NH$_2$-DTYRPKRPTTLNLFPQVPRSQDT-COOH) |
| D-IB$_1$ | 18 | 23 | TDQSRPVQPFLNLTTPRKPRYTD<br>(NH$_2$-TDQSRPVQPFLNLTTPRKPRYTD-COOH) |
| L-IB(generic) | 19 | 19 | XRPTTLXLXXXXXXXQDS/TX<br>(NH$_2$-XRPTTLXLXXXXXXXQDS/TX-COOH) |
| D-IB(generic) | 20 | 19 | XS/TDQXXXXXXXLXLTTPRX<br>(NH$_2$-XS/TDQXXXXXXXLXLTTPRX-COOH) |
| L-generic-TAT | 21 | 17 | XXXXRKKRRQRRRXXXX<br>(NH$_2$-XXXXRKKRRQRRRXXXX-COOH) |
| D-generic-TAT | 22 | 17 | XXXXRRRQRRKKRXXXX<br>(NH$_2$-XXXXRRRQRRKKRXXXX-COOH) |
| L-TAT-IB$_1$ | 23 | 35 | GRKKRRQRRRPPDTYRPKRPTTLNLFPQVPRSQDT<br>(NH$_2$-GRKKRRQRRRPPDTYRPKRPTTLNLFPQVPRSQDT-COOH) |
| L-TAT-IB(generic) | 24 | 42 | XXXXXXXRKKRRQRRRXXXXXXXXRPTTLXLXXXXXXXQDS/TX<br>(NH$_2$-<br>XXXXXXXRKKRRQRRRXXXXXXXXRPTTLXLXXXXXXXQDS/TX-COOH) |
| D-TAT-IB$_1$ | 25 | 35 | TDQSRPVQPFLNLTTPRKPRYTDPPRRRQRRKKRG<br>(NH$_2$-TDQSRPVQPFLNLTTPRKPRYTDPPRRRQRRKKRG-COOH) |
| D-TAT-IB(generic) | 26 | 42 | XT/SDQXXXXXXXLXLTTPRXXXXXXXXRRRQRRKKRXXXXXXXX<br>(NH$_2$-<br>XT/SDQXXXXXXXLXLTTPRXXXXXXXXRRRQRRKKRXXXXXXXX-<br>COOH) |
| L-TAT-IB$_1$(s1) | 27 | 30 | RKKRRQRRRPPRPKRPTTLNLFPQVPRSQD<br>(NH$_2$-RKKRRQRRRPPRPKRPTTLNLFPQVPRSQD-COOH) |
| L-TAT-IB$_1$(s2) | 28 | 30 | GRKKRRQRRRX$_n^c$RPKRPTTLNLFPQVPRSQD<br>(NH$_2$-GRKKRRQRRRX$_n^c$RPKRPTTLNLFPQVPRSQD-COOH) |
| L-TAT-IB$_1$(s3) | 29 | 29 | RKKRRQRRRX$_n^c$RPKRPTTLNLFPQVPRSQD<br>(NH$_2$-RKKRRQRRRX$_n^c$RPKRPTTLNLFPQVPRSQD-COOH) |
| D-TAT-IB$_1$(s1) | 30 | 30 | DQSRPVQPFLNLTTPRKPRPPRRRQRRKKR<br>(NH$_2$-DQSRPVQPFLNLTTPRKPRPPRRRQRRKKR-COOH) |
| D-TAT-IB$_1$(s2) | 31 | 30 | DQSRPVQPFLNLTTPRKPRX$_n^c$RRRQRRKKRG<br>(NH$_2$-DQSRPVQPFLNLTTPRKPRX$_n^c$RRRQRRKKRG-COOH) |

TABLE 1-continued

| SEQUENCE/PEPTIDE NAME | SEQ ID NO | AA | SEQUENCE |
| --- | --- | --- | --- |
| D-TAT-IB$_1$(s3) | 32 | 29 | DQSRPVQPFLNLTTPRKPRX$_n$$^c$RRRQRRKKR (NH$_2$-DQSRPVQPFLNLTTPRKPRX$_n$$^c$RRRQRRKKR-COOH) |
| L-IB$_1$(s1) | 33 | 13 | TLNLFPQVPRSQD (NH$_2$-TLNLFPQVPRSQD-COOH) |
| L-IB$_1$(s2) | 34 | 13 | TTLNLFPQVPRSQ (NH$_2$-TTLNLFPQVPRSQ-COOH) |
| L-IB$_1$(s3) | 35 | 13 | PTTLNLFPQVPRS (NH$_2$-PTTLNLFPQVPRS-COOH) |
| L-IB$_1$(s4) | 36 | 13 | RPTTLNLFPQVPR (NH$_2$-RPTTLNLFPQVPR-COOH) |
| L-IB$_1$(s5) | 37 | 13 | KRPTTLNLFPQVP (NH$_2$-KRPTTLNLFPQVP-COOH) |
| L-IB$_1$(s6) | 38 | 13 | PKRPTTLNLFPQV (NH$_2$-PKRPTTLNLFPQV-COOH) |
| L-IB$_1$(s7) | 39 | 13 | RPKRPTTLNLFPQ (NH$_2$-RPKRPTTLNLFPQ-COOH) |
| L-IB$_1$(s8) | 40 | 12 | LNLFPQVPRSQD (NH$_2$-LNLFPQVPRSQD-COOH) |
| L-IB$_1$(s9) | 41 | 12 | TLNLFPQVPRSQ (NH$_2$-TLNLFPQVPRSQ-COOH) |
| L-IB$_1$(s10) | 42 | 12 | TTLNLFPQVPRS (NH$_2$-TTLNLFPQVPRS-COOH) |
| L-IB$_1$(s11) | 43 | 12 | PTTLNLFPQVPR (NH$_2$-PTTLNLFPQVPR-COOH) |
| L-IB$_1$(s12) | 44 | 12 | RPTTLNLFPQVP (NH$_2$-RPTTLNLFPQVP-COOH) |
| L-IB$_1$(s13) | 45 | 12 | KRPTTLNLFPQV (NH$_2$-KRPTTLNLFPQV-COOH) |
| L-IB$_1$(s14) | 46 | 12 | PKRPTTLNLFPQ (NH$_2$-PKRPTTLNLFPQ-COOH) |
| L-IB$_1$(s15) | 47 | 12 | RPKRPTTLNLFP (NH$_2$-RPKRPTTLNLFP-COOH) |
| L-IB$_1$(s16) | 48 | 11 | NLFPQVPRSQD (NH$_2$-NLFPQVPRSQD-COOH) |
| L-IB$_1$(s17) | 49 | 11 | LNLFPQVPRSQ (NH$_2$-LNLFPQVPRSQ-COOH) |
| L-IB$_1$(s18) | 50 | 11 | TLNLFPQVPRS (NH$_2$-TLNLFPQVPRS-COOH) |
| L-IB$_1$(s19) | 51 | 11 | TTLNLFPQVPR (NH$_2$-TTLNLFPQVPR-COOH) |
| L-IB$_1$(s20) | 52 | 11 | PTTLNLFPQVP (NH$_2$-PTTLNLFPQVP-COOH) |
| L-IB$_1$(s21) | 53 | 11 | RPTTLNLFPQV (NH$_2$-RPTTLNLFPQV-COOH) |
| L-IB$_1$(s22) | 54 | 11 | KRPTTLNLFPQ (NH$_2$-KRPTTLNLFPQ-COOH) |
| L-IB$_1$(s23) | 55 | 11 | PKRPTTLNLFP (NH$_2$-PKRPTTLNLFP-COOH) |
| L-IB$_1$(s24) | 56 | 11 | RPKRPTTLNLF (NH$_2$-RPKRPTTLNLF-COOH) |

TABLE 1-continued

| SEQUENCE/PEPTIDE NAME | SEQ ID NO | AA | SEQUENCE |
|---|---|---|---|
| L-IB$_1$(s25) | 57 | 10 | LFPQVPRSQD<br>(NH$_2$-LFPQVPRSQD-COOH) |
| L-IB$_1$(s26) | 58 | 10 | NLFPQVPRSQ<br>(NH$_2$-NLFPQVPRSQ-COOH) |
| L-IB$_1$(s27) | 59 | 10 | LNLFPQVPRS<br>(NH$_2$-LNLFPQVPRS-COOH) |
| L-IB$_1$(s28) | 60 | 10 | TLNLFPQVPR<br>(NH$_2$-TLNLFPQVPR-COOH) |
| L-IB$_1$(s29) | 61 | 10 | TTLNLFPQVP<br>(NH$_2$-TTLNLFPQVP-COOH) |
| L-IB$_1$(s30) | 62 | 10 | PTTLNLFPQV<br>(NH$_2$-PTTLNLFPQV-COOH) |
| L-IB$_1$(s31) | 63 | 10 | RPTTLNLFPQ<br>(NH$_2$-RPTTLNLFPQ-COOH) |
| L-IB$_1$(s32) | 64 | 10 | KRPTTLNLFP<br>(NH$_2$-KRPTTLNLFP-COOH) |
| L-IB$_1$(s33) | 65 | 10 | PKRPTTLNLF<br>(NH$_2$-PKRPTTLNLF-COOH) |
| L-IB$_1$(s34) | 66 | 10 | RPKRPTTLNL<br>(NH$_2$-RPKRPTTLNL-COOH) |
| D-IB$_1$(s1) | 67 | 13 | QPFLNLTTPRKPR<br>(NH$_2$-QPFLNLTTPRKPR-COOH) |
| D-IB$_1$(s2) | 68 | 13 | VQPFLNLTTPRKP<br>(NH$_2$-VQPFLNLTTPRKP-COOH) |
| D-IB$_1$(s3) | 69 | 13 | PVQPFLNLTTPRK<br>(NH$_2$-PVQPFLNLTTPRK-COOH) |
| D-IB$_1$(s4) | 70 | 13 | RPVQPFLNLTTPR<br>(NH$_2$-RPVQPFLNLTTPR-COOH) |
| D-IB$_1$(s5) | 71 | 13 | SRPVQPFLNLTTP<br>(NH$_2$-SRPVQPFLNLTTP-COOH) |
| D-IB$_1$(s6) | 72 | 13 | QSRPVQPFLNLTT<br>(NH$_2$-QSRPVQPFLNLTT-COOH) |
| D-IB$_1$(s7) | 73 | 13 | DQSRPVQPFLNLT<br>(NH$_2$-DQSRPVQPFLNLT-COOH) |
| D-IB$_1$(s8) | 74 | 12 | PFLNLTTPRKPR<br>(NH$_2$-PFLNLTTPRKPR-COOH) |
| D-IB$_1$(s9) | 75 | 12 | QPFLNLTTPRKP<br>(NH$_2$-QPFLNLTTPRKP-COOH) |
| D-IB$_1$(s10) | 76 | 12 | VQPFLNLTTPRK<br>(NH$_2$-VQPFLNLTTPRK-COOH) |
| D-IB$_1$(s11) | 77 | 12 | PVQPFLNLTTPR<br>(NH$_2$-PVQPFLNLTTPR-COOH) |
| D-IB$_1$(s12) | 78 | 12 | RPVQPFLNLTTP<br>(NH$_2$-RPVQPFLNLTTP-COOH) |
| D-IB$_1$(s13) | 79 | 12 | SRPVQPFLNLTT<br>(NH$_2$-SRPVQPFLNLTT-COOH) |
| D-IB$_1$(s14) | 80 | 12 | QSRPVQPFLNLT<br>(NH$_2$-QSRPVQPFLNLT-COOH) |
| D-IB$_1$(s15) | 81 | 12 | DQSRPVQPFLNL<br>(NH$_2$-DQSRPVQPFLNL-COOH) |
| D-IB$_1$(s16) | 82 | 11 | FLNLTTPRKPR<br>(NH$_2$-FLNLTTPRKPR-COOH) |

TABLE 1-continued

| SEQUENCE/PEPTIDE NAME | SEQ ID NO | AA | SEQUENCE |
|---|---|---|---|
| D-IB₁(s17) | 83 | 11 | PFLNLTTPRKP (NH₂-PFLNLTTPRKP-COOH) |
| D-IB₁(s18) | 84 | 11 | QPFLNLTTPRK (NH₂-QPFLNLTTPRK-COOH) |
| D-IB₁(s19) | 85 | 11 | VQPFLNLTTPR (NH₂-VQPFLNLTTPR-COOH) |
| D-IB₁(s20) | 86 | 11 | PVQPFLNLTTP (NH₂-PVQPFLNLTTP-COOH) |
| D-IB₁(s21) | 87 | 11 | RPVQPFLNLTT (NH₂-RPVQPFLNLTT-COOH) |
| D-IB₁(s22) | 88 | 11 | SRPVQPFLNLT (NH₂-SRPVQPFLNLT-COOH) |
| D-IB₁(s23) | 89 | 11 | QSRPVQPFLNL (NH₂-QSRPVQPFLNL-COOH) |
| D-IB₁(s24) | 90 | 11 | DQSRPVQPFLN (NH₂-DQSRPVQPFLN-COOH) |
| D-IB₁(s25) | 91 | 10 | DQSRPVQPFL (NH₂-DQSRPVQPFL-COOH) |
| D-IB₁(s26) | 92 | 10 | QSRPVQPFLN (NH₂-QSRPVQPFLN-COOH) |
| D-IB₁(s27) | 93 | 10 | SRPVQPFLNL (NH₂-SRPVQPFLNL-COOH) |
| D-IB₁(s28) | 94 | 10 | RPVQPFLNLT (NH₂-RPVQPFLNLT-COOH) |
| D-IB₁(s29) | 95 | 10 | PVQPFLNLTT (NH₂-PVQPFLNLTT-COOH) |
| D-IB₁(s30) | 96 | 10 | VQPFLNLTTP (NH₂-VQPFLNLTTP-COOH) |
| D-IB₁(s31) | 97 | 10 | QPFLNLTTPR (NH₂-QPFLNLTTPR-COOH) |
| D-IB₁(s32) | 98 | 10 | PFLNLTTPRK (NH₂-PFLNLTTPRK-COOH) |
| D-IB₁(s33) | 99 | 10 | FLNLTTPRKP (NH₂-FLNLTTPRKP-COOH) |
| D-IB₁(s34) | 100 | 10 | LNLTTPRKPR (NH₂-LNLTTPRKPR-COOH) |

It will be understood by a person skilled in the art that a given sequence herein which is composed exclusively of D-amino acids is identified by "D-name". For example, SEQ ID NO:100 has the sequence/peptide name "D-IB1 (s34)". The given amino acid sequence is LNLTTPRKPR (SEQ ID NO:100). However, all amino acids are here D-amino acids.

It will be also understood by a person skilled in the art that the terms "entirely composed of L-amino acids"; "exclusively composed of D-amino acids" "entirely composed of D-amino acids" and/or "exclusively composed of D-amino acids" and the like refer to sequences which need not (but may) exclude the presence of glycine residues. Glycine is the only amino acid which is non-chiral. Therefore, the terms "entirely composed of L-amino acids"; "exclusively composed of D-amino acids" "entirely composed of D-amino acids" and/or "exclusively composed of D-amino acids" are intended to make clear that L-amino acids or D-amino acids, respectively, are used where possible. Nevertheless, if presence of a glycine is necessary or favored at a given position in the amino acid sequence, then it may remain there. A good example is L-TAT (SEQ ID NO:5). As used herein said sequence is considered to be exclusively composed of L-amino acids "although" said sequence comprises a non chiral glycine residue. Likewise, D-TAT (SEQ ID NO:6), as used herein, may be considered to be exclusively composed of D-amino acids "although" said sequence comprises a non chiral glycine residue.

According to another preferred embodiment, the JNK inhibitor (poly-)peptide as used herein comprises or consists of at least one variant, fragment and/or derivative of the above defined native or non-native amino acid sequences according to SEQ ID NOs: 1-4, 13-20 and 33-100.

Preferably, these variants, fragments and/or derivatives retain biological activity of the above disclosed native or non-native JNK inhibitor (poly-)peptides as used herein, particularly of native or non-native amino acid sequences according to SEQ ID NOs: 1-4, 13-20 and 33-100, i.e. binding JNK and/or inhibiting the activation of at least one JNK activated transcription factor, e.g. c-Jun, ATF2 or Elk1. Functionality may be tested by various tests, e.g. binding tests of the peptide to its target molecule or by biophysical methods, e.g. spectroscopy, computer modeling, structural analysis, etc. Particularly, an JNK inhibitor (poly-)peptide or variants, fragments and/or derivatives thereof as defined above may be analyzed by hydrophilicity analysis (see e.g. Hopp and Woods, 1981. Proc Natl Acad Sci USA 78: 3824-3828) that can be utilized to identify the hydrophobic and hydrophilic regions of the peptides, thus aiding in the design of substrates for experimental manipulation, such as in binding experiments, or for antibody synthesis. Secondary structural analysis may also be performed to identify regions of an JNK inhibitor (poly-)peptide or of variants, fragments and/or derivatives thereof as used herein that assume specific structural motifs (see e.g. Chou and Fasman, 1974, Biochem 13: 222-223). Manipulation, translation, secondary structure prediction, hydrophilicity and hydrophobicity profiles, open reading frame prediction and plotting, and determination of sequence homologies can be accomplished using computer software programs available in the art. Other methods of structural analysis include, e.g. X-ray crystallography (see e.g. Engstrom, 1974. Biochem Exp Biol 11: 7-13), mass spectroscopy and gas chromatography (see e.g. METHODS IN PROTEIN SCIENCE, 1997, J. Wiley and Sons, New York, N.Y.) and computer modeling (see e.g. Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

Accordingly, the JNK inhibitor (poly-)peptide as used herein may comprise or consist of at least one variant of (native or non-native) amino acid sequences according to SEQ ID NOs: 1-4, 13-20 and 33-100. In the context of the present invention, a "variant of a (native or non-native) amino acid sequence according to SEQ ID NOs: 1-4, 13-20 and 33-100" is preferably a sequence derived from any of the sequences according to SEQ ID NOs: 1-4, 13-20 and 33-100, wherein the variant comprises amino acid alterations of the amino acid sequences according to SEQ ID NOs: 1-4, 13-20 and 33-100. Such alterations typically comprise 1 to 20, preferably 1 to 10 and more preferably 1 to 5 substitutions, additions and/or deletions of amino acids according to SEQ ID NOs: 1-4, 13-20 and 33-100, wherein the variant exhibits a sequence identity with any of the sequences according to SEQ ID NOs: 1-4, 13-20 and 33-100 of at least about 30%, 50%, 70%, 80%, 90%, 95%, 98% or even at least about 99%.

If variants of (native or non-native) amino acid sequences according to SEQ ID NOs: 1-4, 13-20 and 33-100 as defined above and used herein are obtained by substitution of specific amino acids, such substitutions preferably comprise conservative amino acid substitutions. Conservative amino acid substitutions may include synonymous amino acid residues within a group which have sufficiently similar physicochemical properties, so that a substitution between members of the group will preserve the biological activity of the molecule (see e.g. Grantham, R. (1974), Science 185, 862-864). It is evident to the skilled person that amino acids may also be inserted and/or deleted in the above-defined sequences without altering their function, particularly if the insertions and/or deletions only involve a few amino acids, e.g. less than twenty, and preferably less than ten, and do not remove or displace amino acids which are critical to functional activity. Moreover, substitutions shall be avoided in variants as used herein, which lead to additional threonines at amino acid positions which are accessible for a phosphorylase, preferably a kinase, in order to avoid inactivation of the JNK-inhibitor (poly-)peptide as used herein or of the chimeric peptide as used herein in vivo or in vitro.

Preferably, synonymous amino acid residues, which are classified into the same groups and are typically exchangeable by conservative amino acid substitutions, are defined in Table 2.

TABLE 2

| Preferred Groups of Synonymous Amino Acid Residues | |
|---|---|
| Amino Acid | Synonymous Residue |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, (Thr), Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, (Thr), Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, (Thr), Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

A specific form of a variant of SEQ ID NOs: 1-4, 13-20 and 33-100 as used herein is a fragment of the (native or non-native) amino acid sequences according to SEQ ID NOs: 1, 1-4, 13-20 and 33-100" as used herein, which is typically altered by at least one deletion as compared to SEQ ID NOs 1-4, 13-20 and 33-100. Preferably, a fragment comprises at least 4 contiguous amino acids of any of SEQ ID NOs: 1-4, 13-20 and 33-100, a length typically sufficient to allow for specific recognition of an epitope from any of these sequences. Even more preferably, the fragment comprises 4 to 18, 4 to 15, or most preferably 4 to 10 contiguous amino acids of any of SEQ ID NOs: 1-4, 13-20 and 33-100, wherein the lower limit of the range may be 4, or 5, 6, 7, 8, 9, or 10. Deleted amino acids may occur at any position of SEQ ID NOs: 1-4, 13-20 and 33-100, preferably N- or C-terminally.

Furthermore, a fragment of the (native or non-native) amino acid sequences according to SEQ ID NOs: 1-4, 13-20 and 33-100, as described above, may be defined as a sequence sharing a sequence identity with any of the sequences according to SEQ ID NOs: 1-4, 13-20 and 33-100 as used herein of at least about 30%, 50%, 70%, 80%, 90%, 95%, 98%, or even 99%.

The JNK inhibitor (poly-)peptides/sequences as used herein may further comprise or consist of at least one derivative of (native or non-native) amino acid sequences according to SEQ ID NOs: 1-4, 13-20 and 33-100 as defined above. In this context, a "derivative of an (native or non-native) amino acid sequence according to SEQ ID NOs: 1-4, 13-20 and 33-100" is preferably an amino acid sequence derived from any of the sequences according to SEQ ID NOs: 1-4, 13-20 and 33-100, wherein the derivative comprises at least one modified L- or D-amino acid (forming non-natural amino acid(s)), preferably 1 to 20, more preferably 1 to 10, and even more preferably 1 to 5 modified L- or D-amino acids. Derivatives of variants or fragments also fall under the scope of the present invention.

"A modified amino acid" in this respect may be any amino acid which is altered e.g. by different glycosylation in various organisms, by phosphorylation or by labeling specific amino acids. Such a label is then typically selected from the group of labels comprising:
  (i) radioactive labels, i.e. radioactive phosphorylation or a radioactive label with sulphur, hydrogen, carbon, nitrogen, etc.;
  (ii) colored dyes (e.g. digoxygenin, etc.);
  (iii) fluorescent groups (e.g. fluorescein, etc.);
  (iv) chemolumminescent groups;
  (v) groups for immobilization on a solid phase (e.g. His-tag, biotin, strep-tag, flag-tag, antibodies, antigen, etc.); and
  (vi) a combination of labels of two or more of the labels mentioned under (i) to (v).

In the above context, an amino acid sequence having a sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted.

For sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences, particularly as used herein, are well known in the art. Thus for instance, programs available in the Wisconsin Sequence Analysis Package, version 9.1 (Devereux et al., 1984, Nucleic Acids Res. 12, 387-395.), for example the programs BESTFIT and GAP, may be used to determine the % identity between two polynucleotides and the % identity and the % homology between two polypeptide sequences. BESTFIT uses the "local homology" algorithm of (Smith and Waterman (1981), J. Mol. Biol. 147, 195-197.) and finds the best single region of similarity between two sequences. Other programs for determining identity and/or similarity between sequences are also known in the art, for instance the BLAST family of programs (Altschul et al., 1990, J. Mol. Biol. 215, 403-410), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U. S. A 85, 2444-2448.).

JNK-inhibitor (poly-)peptides/sequences as used according to the present invention and as defined above may be obtained or produced by methods well-known in the art, e.g. by chemical synthesis or by genetic engineering methods as discussed below. For example, a peptide corresponding to a portion of an JNK inhibitor sequence as used herein including a desired region of said JNK inhibitor sequence, or that mediates the desired activity in vitro or in vivo, may be synthesized by use of a peptide synthesizer.

JNK inhibitor (poly-)peptide as used herein and as defined above, may be furthermore be modified by a trafficking (poly-)peptide, allowing the JNK inhibitor (poly-)peptide as used herein and as defined above to be transported effectively into the cells. Such modified JNK inhibitor (poly-)peptides are preferably provided and used as chimeric (poly-)peptides.

According to a second aspect the present invention therefore provides the use of a chimeric (poly-) peptide including at least one first domain and at least one second domain, for the preparation of a pharmaceutical composition for treating non-chronic or chronic inflammatory eye diseases in a subject, wherein the first domain of the chimeric peptide comprises a trafficking sequence, while the second domain of the chimeric (poly-)peptide comprises an JNK inhibitor sequence as defined above, preferably of any of sequences according to SEQ ID NO: 1-4, 13-20 and 33-100 or a derivative or a fragment thereof.

Typically, chimeric (poly-)peptides as used according to the present invention have a length of at least 25 amino acid residues, e.g. 25 to 250 amino acid residues, more preferably 25 to 200 amino acid residues, even more preferably 25 to 150 amino acid residues, 25 to 100 and most preferably amino acid 25 to 50 amino acid residues.

As a first domain the chimeric (poly-)peptide as used herein preferably comprises a trafficking sequence, which is typically selected from any sequence of amino acids that directs a peptide (in which it is present) to a desired cellular destination. Thus, the trafficking sequence, as used herein, typically directs the peptide across the plasma membrane, e.g. from outside the cell, through the plasma membrane, and into the cytoplasm. Alternatively, or in addition, the trafficking sequence may direct the peptide to a desired location within the cell, e.g. the nucleus, the ribosome, the endoplasmic reticulum (ER), a lysosome, or peroxisome, by e.g. combining two components (e.g. a component for cell permeability and a component for nuclear location) or by one single component having e.g. properties of cell membrane transport and targeted e.g. intranuclear transport. The trafficking sequence may additionally comprise another component, which is capable of binding a cytoplasmic component or any other component or compartment of the cell (e.g. endoplasmic reticulum, mitochondria, gloom apparatus, lysosomal vesicles). Accordingly, e.g. the trafficking sequence of the first domain and the JNK inhibitor sequence of the second domain may be localized in the cytoplasm or any other compartment of the cell. This allows to determine localization of the chimeric peptide in the cell upon uptake.

Preferably, the trafficking sequence (being included in the first domain of the chimeric peptide as used herein) has a length of 5 to 150 amino acid sequences, more preferably a length of 5 to 100 and most preferably a length of from 5 to 50, 5 to 30 or even 5 to 15 amino acids.

More preferably, the trafficking sequence (contained in the first domain of the chimeric peptide as used herein) may occur as a continuous amino acid sequence stretch in the first domain. Alternatively, the trafficking sequence in the first domain may be splitted into two or more fragments, wherein all of these fragments resemble the entire trafficking sequence and may be separated from each other by 1 to 10, preferably 1 to 5 amino acids, provided that the trafficking sequence as such retains its carrier properties as disclosed above. These amino acids separating the fragments of the trafficking sequence may e.g. be selected from amino acid sequences differing from the trafficking sequence. Alternatively, the first domain may contain a trafficking sequence composed of more than one component, each component with its own function for the transport of the cargo JNK inhibitor sequence of the second domain to e.g. a specific cell compartment.

The trafficking sequence as defined above may be composed of L-amino acids, D-amino acids, or a combination of both. Preferably, the trafficking sequences (being included in the first domain of the chimeric peptide as used herein) may comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK trafficking sequences in a blockwise, a non-blockwise or in an alternate manner.

According to one alternative embodiment, the trafficking sequence of the chimeric (poly-)peptide as used herein may be exclusively composed of L-amino acids. More preferably, the trafficking sequence of the chimeric peptide as used herein comprises or consists of at least one "native" trafficking sequence as defined above. In this context, the term "native" is referred to non-altered trafficking sequences, entirely composed of L-amino acids.

According to another alternative embodiment the trafficking sequence of the chimeric (poly-) peptide as used herein may be exclusively composed of D-amino acids. More preferably, the trafficking sequence of the chimeric peptide as used herein may comprise a D retro-inverso peptide of the sequences as presented above.

The trafficking sequence of the first domain of the chimeric (poly-)peptide as used herein may be obtained from naturally occurring sources or can be produced by using genetic engineering techniques or chemical synthesis (see e.g. Sambrook, J., Fritsch, E. F., Maniatis, T. (1989) Molecular cloning: A laboratory manual. 2nd edition. Cold Spring Harbor Laboratory Press, Cold Spring Harbor, N.Y.).

Sources for the trafficking sequence of the first domain may be employed including, e.g. native proteins such as e.g. the TAT protein (e.g. as described in U.S. Pat. Nos. 5,804,604 and 5,674,980, each of these references being incorporated herein by reference), VP22 (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), trafficking sequences derived from Antennapedia (e.g. the antennapedia carrier sequence) or from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine. Furthermore, variants, fragments and derivatives of one of the native proteins used as trafficking sequences are disclosed herewith. With regard to variants, fragments and derivatives it is referred to the definition given above for JNK inhibitor sequences as used herein. Variants, fragments as well as derivatives are correspondingly defined as set forth above for JNK inhibitor sequences as used herein. Particularly, in the context of the trafficking sequence, a variant or fragment or derivative may be defined as a sequence sharing a sequence identity with one of the native proteins used as trafficking sequences as defined above of at least about 30%, 50%, 70%, 80%, 90%, 95%, 98%, or even 99%.

In a preferred embodiment of the chimeric (poly-)peptide as used herein, the trafficking sequence of the first domain comprises or consists of a sequence derived from the human immunodeficiency virus (HIV) 1 TAT protein, particularly some or all of the 86 amino acids that make up the TAT protein.

For a trafficking sequence (being included in the first domain of the chimeric peptide as used herein), partial sequences of the full-length TAT protein may be used forming a functionally effective fragment of a TAT protein, i.e. a TAT peptide that includes the region that mediates entry and uptake into cells. As to whether such a sequence is a functionally effective fragment of the TAT protein can be determined using known techniques (see e.g. Franked et al., Proc. Natl. Acad. Sci, USA 86: 7397-7401 (1989)). Thus, the trafficking sequence in the first domain of the chimeric peptide as used herein may be derived from a functionally effective fragment or portion of a TAT protein sequence that comprises less than 86 amino acids, and which exhibits uptake into cells, and optionally the uptake into the cell nucleus. More preferably, partial sequences (fragments) of TAT to be used as carrier to mediate permeation of the chimeric peptide across the cell membrane, are intended to comprise the basic region (amino acids 48 to 57 or 49 to 57) of full-length TAT.

According to a more preferred embodiment, the trafficking sequence (being included in the first domain of the chimeric peptide as used herein) may comprise or consist of an amino acid sequence containing TAT residues 48-57 or 49 to 57, and most preferably a generic TAT sequence $NH_2$—$X_n^b$—RKKRRQRRR-$X_n^b$—COOH (L-generic-TAT (s)) [SEQ ID NO: 7] and/or XXXXRKKRRQ RRRXXXX (L-generic-TAT) [SEQ ID NO: 21], wherein X or $X_n^b$ is as defined above. Furthermore, the number of "$X_n^b$" residues in SEQ ID NOs:8 is not limited to the one depicted, and may vary as described above. Alternatively, the trafficking sequence being included in the first domain of the chimeric peptide as used herein may comprise or consist of a peptide containing e.g. the amino acid sequence $NH_2$-GRKKRRQRRR—COOH (L-TAT) [SEQ ID NO: 5].

According to another more preferred embodiment the trafficking sequence (being included in the first domain of the chimeric peptide as used herein) may comprise a D retro-inverso peptide of the sequences as presented above, i.e. the D retro-inverso sequence of the generic TAT sequence having the sequence $NH_2$—$X_n^b$—RRRQRRKKR—$X_n^b$—COOH (D-generic-TAT (s)) [SEQ ID NO: 8] and/or XXXXRRRQRRKKRXXXX (D-generic-TAT) [SEQ ID NO: 22]. Also here, $X_n^b$ is as defined above (preferably representing D amino acids). Furthermore, the number of "$X_n^b$" residues in SEQ ID NOs:8 is not limited to the one depicted, and may vary as described above. Most preferably, the trafficking sequence as used herein may comprise the D retro-inverso sequence $NH_2$—RRRQRRKKRG-COOH (D-TAT) [SEQ ID NO: 6].

According to another embodiment the trafficking sequence being included in the first domain of the chimeric peptide as used herein may comprise or consist of variants of the trafficking sequences as defined above. A "variant of a trafficking sequence" is preferably a sequence derived from a trafficking sequence as defined above, wherein the variant comprises a modification, for example, addition, (internal) deletion (leading to fragments) and/or substitution of at least one amino acid present in the trafficking sequence as defined above. Such (a) modification(s) typically comprise(s) 1 to 20, preferably 1 to 10 and more preferably 1 to 5 substitutions, additions and/or deletions of amino acids. Furthermore, the variant preferably exhibits a sequence identity with the trafficking sequence as defined above, more preferably with any of SEQ ID NOs: 5 to 8 or 21-22, of at least about 30%, 50%, 70%, 80%, 90%, 95%, 98% or even 99%.

Preferably, such a modification of the trafficking sequence being included in the first domain of the chimeric peptide as used herein leads to a trafficking sequence with increased or decreased stability. Alternatively, variants of the trafficking sequence can be designed to modulate intracellular localization of the chimeric peptide as used herein. When added exogenously, such variants as defined above are typically designed such that the ability of the trafficking sequence to enter cells is retained (i.e. the uptake of the variant of the trafficking sequence into the cell is substantially similar to that of the native protein used a trafficking sequence). For example, alteration of the basic region thought to be important for nuclear localization (see e.g. Dang and Lee, J. Biol. Chem. 264: 18019-18023 (1989); Hauber et al., J. Virol. 63: 1181-1187 (1989); et al., J. Virol. 63: 1-8 (1989)) can result in a cytoplasmic location or partially cytoplasmic location of the trafficking sequence, and therefore, of the JNK inhibitor sequence as component of the chimeric peptide as used herein. Additional to the above, further modifications may be introduced into the variant, e.g. by linking e.g. cholesterol or other lipid moieties to the trafficking sequence to produce a trafficking sequence having increased membrane solubility. Any of the above disclosed variants of the trafficking sequences being included in the first domain of the chimeric peptide as used herein can be produced using techniques typically known to a skilled person (see e.g. Sambrook, J., Fritsch, E. F., Maniatis, T. (1989) Molecular cloning: A laboratory manual. 2nd edition. Cold Spring Harbor Laboratory, Cold Spring Harbor, N.Y.)

As a second domain the chimeric peptide as used herein typically comprises an JNK inhibitor sequence, selected from any of the JNK inhibitor sequences as defined above, including variants, fragments and/or derivatives of these JNK inhibitor sequences.

Both domains, i.e. the first and the second domain(s), of the chimeric peptide as used herein, may be linked such as to form a functional unit. Any method for linking the first and second domain(s) as generally known in the art may be applied.

According to one embodiment, the first and the second domain(s) of the chimeric peptide as used herein are preferably linked by a covalent bond. A covalent bond, as defined herein, may be e.g. a peptide bond, which may be obtained by expressing the chimeric peptide as defined above as a fusion protein. Fusion proteins, as described herein, can be formed and used in ways analogous to or readily adaptable from standard recombinant DNA techniques, as described below. However, both domains may also be linked via side chains or may be linked by a chemical linker moiety.

The first and/or second domains of the chimeric peptide as used herein may occur in one or more copies in said chimeric peptide. If both domains are present in a single copy, the first domain may be linked either to the N-terminal or the C-terminal end of the second domain. If present in multiple copies, the first and second domain(s) may be arranged in any possible order. E.g. the first domain can be present in the chimeric peptide as used herein in a multiple copy number, e.g. in two, three or more copies, which are preferably arranged in consecutive order. Then, the second domain may be present in a single copy occurring at the N- or C-terminus of the sequence comprising the first domain. Alternatively, the second domain may be present in a multiple copy number, e.g. in two, three or more copies, and the first domain may be present in a single copy. According to both alternatives, first and second domain(s) can take any place in a consecutive arrangement. Exemplary arrangements are shown in the following: e.g. first domain—first domain—first domain—second domain; first domain—first domain—second domain—first domain; first domain—second domain—first domain—first domain; or e.g. second domain—first domain—first domain—first domain. It is well understood for a skilled person that these examples are for illustration purposes only and shall not limit the scope of the invention thereto. Thus, the number of copies and the arrangement may be varied as defined initially.

Preferably, the first and second domain(s) may be directly linked with each other without any linker. Alternatively, they may be linked with each other via a linker sequence comprising 1 to 10, preferably 1 to 5 amino acids. Amino acids forming the linker sequence are preferably selected from glycine or proline as amino acid residues. More preferably, the first and second domain(s) may be separated by each other by a hinge of two, three or more proline residues between the first and second domain(s).

The chimeric peptide as defined above and as used herein, comprising at least one first and at least one second domain, may be composed of L-amino acids, D-amino acids, or a combination of both. Therein, each domain (as well as the linkers used) may be composed of L-amino acids, D-amino acids, or a combination of both (e.g. D-TAT and L-IB1(s) or L-TAT and D-IB1(s), etc.). Preferably, the chimeric peptide as used herein may comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the chimeric peptide as used herein in a blockwise, a non-blockwise or in an alternate manner.

According to a specific embodiment the chimeric peptide as used herein comprises or consists of the L-amino acid chimeric peptides according to the generic L-TAT-IB peptide $NH_2-X_n^b-RKKRRQRRR-X_n^b-X_n^a-RPTTLXLX$ XX-XXXXQD-$X_n^b$—COOH (L-TAT-IB (generic) (s)) [SEQ ID NO: 10], wherein X, $X_n^a$ and $X_n^b$ are preferably as defined above. More preferably, the chimeric peptide as used herein comprises or consists of the L-amino acid chimeric peptide $NH_2$-GRKKRRQRRRPPRPKRPTTLNLFPQVPRSQDC-OOH (L-TAT-IB (s)) [SEQ ID NO: 9]. Alternatively or additionally, the chimeric peptide as used herein comprises or consists of the L-amino acid chimeric peptide sequence GRKKRRQRRR PPDTYRPKRP TTLNLFPQVP RSQDT (L-TAT-IB1) [SEQ ID NO: 23], or XXXXXXXXRKK RRQRRRXXXX XXXXRPTTLX LXXXXXXXQD S/TX (L-TAT-IB generic) [SEQ ID NO: 24], wherein X is preferably also as defined above, or the chimeric peptide as used herein comprises or consists of the L-amino acid chimeric peptide sequence RKKRRQRRRPPRPKRPTTLNLFPQ-VPRSQD (L-TAT-IB1(s1)) [SEQ ID NO: 27], GRKKRR-QRRR$X_n^c$RPKRPTTLNLFPQVPRSQD (L-TAT-IB1(s2)) [SEQ ID NO: 28], or RKKRRQRRR$X_n^c$RPKRPTTLNLF-PQVPRSQD (L-TAT-IB1(s3)) [SEQ ID NO: 29]. In this context, each X typically represents an amino acid residue as defined above, more preferably $X_n^c$ represents a contiguous stretch of peptide residues, each X independently selected from each other from glycine or proline, e.g. a monotonic glycine stretch or a monotonic proline stretch, wherein n (the number of repetitions of $X_n^c$) is typically 0-5, 5-10, 10-15, 15-20, 20-30 or even more, preferably 0-5 or 5-10. $X_n^c$ may represent either D or L amino acids.

According to an alternative specific embodiment the chimeric peptide as used herein comprises or consists of D-amino acid chimeric peptides of the above disclosed L-amino acid chimeric peptides. Exemplary D retro-inverso chimeric peptides according to the present invention are e.g. the generic D-TAT-IB peptide NH$_2$—X$_n^b$-DQXXXXXXX-LXLTTPR—X$_n^a$—X$_n^b$—RRRQRRKKR—X$_n^b$—COOH (D-TAT-IB (generic) (s)) [SEQ ID NO: 12]. Herein, X, X$_n^a$ and X$_n^b$ are preferably as defined above (preferably representing D amino acids). More preferably, the chimeric peptide as used herein comprises or consists of D-amino acid chimeric peptides according to the TAT-IB1 peptide NH$_2$-DQSRPVQPFLNLTTPRKPRPPRRRQRRKKRG-C-OOH (D-TAT-IB1(s)) [SEQ ID NO: 11]. Alternatively or additionally, the chimeric peptide as used herein comprises or consists of the D-amino acid chimeric peptide sequence TDQSRPVQPFLNLTTPRKPRYTDPPRRRQRRKKRG (D-TAT-IB1) [SEQ ID NO: 25], or XT/SDQXXXX-XXXLXLTTPRXXXXXXXXXRRRQRRKKRXXXXXXX (D-TAT-IB generic) [SEQ ID NO: 26], wherein X is preferably also as defined above, or the chimeric peptide as used herein comprises or consists of the D-amino acid chimeric peptide sequence DQSRPVQPFLNLTTPRKPRPPRRR-QRRKKR (D-TAT-IB1(s1)) [SEQ ID NO: 30], DQSRPVQPFLNLTTPRKPRX$_n^c$RRRQRRKKRG (D-TAT-IB1(s2)) [SEQ ID NO: 31], or DQSRPVQPFLNLTT-PRKPRX$_n^c$RRQRRKKR (D-TAT-IB1(s3)) [SEQ ID NO: 32]. $X_n^c$ may be as defined above.

The first and second domain(s) of the chimeric peptide as defined above may be linked to each other by chemical or biochemical coupling carried out in any suitable manner known in the art, e.g. by establishing a peptide bond between the first and the second domain(s) e.g. by expressing the first and second domain(s) as a fusion protein, or e.g. by cross-linking the first and second domain(s) of the chimeric peptide as defined above.

Many known methods suitable for chemical crosslinking of the first and second domain(s) of the chimeric peptide as defined above are non-specific, i.e. they do not direct the point of coupling to any particular site on the transport polypeptide or cargo macromolecule. As a result, use of non-specific crosslinking agents may attack functional sites or sterically block active sites, rendering the conjugated proteins biologically inactive. Thus, preferably such cross-linking methods are used, which allow a more specific coupling of the first and second domain(s).

In this context, one way to increasing coupling specificity is a direct chemical coupling to a functional group present only once or a few times in one or both of the first and second domain(s) to be crosslinked. For example, cysteine, which is the only protein amino acid containing a thiol group, occurs in many proteins only a few times. Also, for example, if a polypeptide contains no lysine residues, a crosslinking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity. Cysteine residues may be replaced when they occur in parts of a polypeptide sequence where their participation in a crosslinking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for crosslinking purposes. When a cysteine residue is introduced, introduction at or near the amino or carboxy terminus is preferred. Conventional methods are available for such amino acid sequence modifications, wherein the polypeptide of interest is produced by chemical synthesis or via expression of recombinant DNA.

Coupling of the first and second domain(s) of the chimeric peptide as defined above and used herein can also be accomplished via a coupling or conjugating agent. There are several intermolecular crosslinking reagents which can be utilized (see for example, Means and Feeney, CHEMICAL MODIFICATION OF PROTEINS, Holden-Day, 1974, pp. 39-43). Among these reagents are, for example, N-succinimidyl 3-(2-pyridyldithio) propionate (SPDP) or N,N'-(1,3-phenylene) bismaleimide (both of which are highly specific for sulfhydryl groups and form irreversible linkages); N, N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other crosslinking reagents useful for this purpose include: p,p'-difluoro-m, m'-dinitrodiphenylsulfone which forms irreversible crosslinkages with amino and phenolic groups); dimethyl adipimidate (which is specific for amino groups); phenol-1,4 disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Crosslinking reagents used for crosslinking the first and second domain(s) of the chimeric peptide as defined above may be homobifunctional, i.e. having two functional groups that undergo the same reaction. A preferred homobifunctional crosslinking reagent is bismaleimidohexane ("BMH"). BMH contains two maleimide functional groups, which react specifically with sulfhydryl-containing compounds under mild conditions (pH 6.5-7.7). The two male-imide groups are connected by a hydrocarbon chain. Therefore, BMH is useful for irreversible crosslinking of polypeptides that contain cysteine residues.

Crosslinking reagents used for crosslinking the first and second domain(s) of the chimeric peptide as defined above may also be heterobifunctional. Heterobifunctional cross-linking agents have two different functional groups, for example an amine-reactive group and a thiol-reactive group, that will crosslink two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these crosslinkers reacts with a primary amine, and the thiol-reactive maleimide forms a covalent bond with the thiol of a cysteine residue.

Crosslinking reagents suitable for crosslinking the first and second domain(s) of the chimeric peptide as defined above often have low solubility in water. A hydrophilic moiety, such as a sulfonate group, may thus be added to the crosslinking reagent to improve its water solubility. In this respect, Sulfo-MBS and Sulfo-SMCC are examples of crosslinking reagents modified for water solubility, which may be used according to the present invention.

Likewise, many crosslinking reagents yield a conjugate that is essentially non-cleavable under cellular conditions. However, some crosslinking reagents particularly suitable for crosslinking the first and second domain(s) of the chimeric peptide as defined above contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable crosslinkers. The use of a cleavable crosslinking reagent permits the cargo moiety to separate from the transport polypeptide after delivery into the target cell. Direct disulfide linkage may also be useful.

Numerous crosslinking reagents, including the ones discussed above, are commercially available. Detailed instructions for their use are readily available from the commercial suppliers. A general reference on protein crosslinking and conjugate preparation is: Wong, CHEMISTRY OF PROTEIN CONJUGATION AND CROSSLINKING, CRC Press (1991).

Chemical crosslinking of the first and second domain(s) of the chimeric peptide as defined above may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the crosslinking reagent, such as in "long-chain SPDP" (Pierce Chem. Co., Rockford, Ill., cat. No. 21651 H).

Furthermore, variants, fragments or derivatives of one of the above disclosed chimeric peptides may be used herein. With regard to fragments and variants it is generally referred to the definition given above for JNK inhibitor sequences.

Particularly, in the context of the present invention, a "variant of a chimeric peptide" is preferably a sequence derived from any of the sequences according to SEQ ID NOs: 9 to 12 and 23 to 32, wherein the chimeric variant comprises amino acid alterations of the chimeric peptides according to SEQ ID NOs: 9 to 12 and 23 to 32 as used herein. Such alterations typically comprise 1 to 20, preferably 1 to 10 and more preferably 1 to 5 substitutions, additions and/or deletions (leading to fragments) of amino acids according to SEQ ID NOs: 9 to 12 and 23 to 32, wherein the altered chimeric peptide as used herein exhibits a sequence identity with any of the sequences according to SEQ ID NOs: 9-12 and 23 to 32 of at least about 30%, 50%, 70%, 80%, or 95%, 98%, or even 99%. Preferably, these variants retain the biological activity of the first and the second domain as contained in the chimeric peptide as used herein, i.e. the trafficking activity of the first domain as disclosed above and the activity of the second domain for binding JNK and/or inhibiting the activation of at least one JNK activated transcription factor.

Accordingly, the chimeric peptide as used herein also comprises fragments of the afore disclosed chimeric peptides, particularly of the chimeric peptide sequences according to any of SEQ ID NOs: 9 to 12 and 23 to 32. Thus, in the context of the present invention, a "fragment of the chimeric peptide" is preferably a sequence derived any of the sequences according to SEQ ID NOs: 9 to 12 and 23 to 32, wherein the fragment comprises at least 4 contiguous amino acids of any of SEQ ID NOs: 9 to 12 and 23 to 32. This fragment preferably comprises a length which is sufficient to allow specific recognition of an epitope from any of these sequences and to transport the sequence into the cells, the nucleus or a further preferred location. Even more preferably, the fragment comprises 4 to 18, 4 to 15, or most preferably 4 to 10 contiguous amino acids of any of SEQ ID NOs: 9 to 12 and 23 to 32. Fragments of the chimeric peptide as used herein further may be defined as a sequence sharing a sequence identity with any of the sequences according to any of SEQ ID NOs: 99 to 12 and 23 to 32 of at least about 30%, 50%, 70%, 80%, or 95%, 98%, or even 99%.

Finally, the chimeric peptide as used herein also comprises derivatives of the afore disclosed chimeric peptides, particularly of the chimeric peptide sequences according to any of SEQ ID NOs: 9 to 12 and 23 to 32.

A particularly preferred use of the present invention is the use of a JNK inhibitor (poly-)peptide consisting of or comprising the amino acid sequence of SEQ ID NO: 11, or consisting of or comprising an amino acid sequence sharing a sequence identity of at least about 30%, 50%, 70%, 80%, 90%, 92% or even 95% with SEQ ID NO: 11, for the treatment of inflammatory eye diseases, in particular for the treatment of uveitis, for example for the treatment of anterior uveitis, intermediate uveitis, posterior uveitis or panuveitis. The JNK inhibitor (poly-)peptide consisting of or comprising the amino acid sequence of SEQ ID NO: 11, or consisting of or comprising an amino acid sequence sharing a sequence identity of at least about 30%, 50%, 70%, 80%, 90%, 92% or even 95% with SEQ ID NO: 11 may be administered for example locally to the eye or systemically. However, the present application also clearly contemplates the use of other JNK inhibitor chimeric (poly-)peptides, i.e. where the JNK inhibitor poly-)peptide used does not consist of or comprise the amino acid sequence of SEQ ID NO: 11 for the treatment of inflammatory eye diseases, in particular for the treatment of uveitis, for example for the treatment of anterior uveitis, intermediate uveitis, posterior uveitis or panuveitis.

Furthermore, the inventors also clearly contemplate the use of the JNK inhibitor (poly-)peptides of the present invention, in particular where the JNK inhibitor poly-)peptide used consists of or comprises the amino acid sequence of SEQ ID NO: 11 or consists of or comprises an amino acid sequence sharing a sequence identity of at least about 30%, 50%, 70%, 80%, 90%, 92% or even 95% with SEQ ID NO: 11, for the treatment of inflammatory eye diseases other than inflammation of the uvea and/or retina, e.g. for the treatment of inflammatory eye diseases which are not uveitis and/or retinitis. Moreover, it must be noted that the present invention does in particular not contemplate the treatment of (non-inflammatory) retinopathy.

The present invention additionally refers to the use of nucleic acid sequences encoding JNK inhibitor sequences as defined above, chimeric peptides or their fragments, variants or derivatives, all as defined above, for the preparation of a pharmaceutical composition for treating non-chronic or chronic inflammatory eye diseases in a subject as defined herein. A preferable suitable nucleic acid encoding an JNK inhibitor sequence as used herein is typically chosen from human IB1 nucleic acid (GenBank Accession No. (AF074091), rat IB1 nucleic acid (GenBank Accession No. AF 108959), or human IB2 (GenBank Accession No AF218778) or from any nucleic acid sequence encoding any of the sequences as defined above, i.e. any sequence according to SEQ ID NO: 1-26.

Nucleic acids encoding the JNK inhibitor sequences as used herein or chimeric peptides as used herein may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Additionally, nucleic acid sequences are disclosed herein as well, which hybridize under stringent conditions with the appropriate strand coding for a (native) JNK inhibitor sequence or chimeric peptide as defined above. Preferably, such nucleic acid sequences comprise at least 6 (contiguous) nucleic acids, which have a length sufficient to allow for specific hybridization. More preferably, such nucleic acid sequences comprise 6 to 38, even more preferably 6 to 30, and most preferably 6 to 20 or 6 to 10 (contiguous) nucleic acids.

"Stringent conditions" are sequence dependent and will be different under different circumstances. Generally, stringent conditions can be selected to be about 5° C. lower than the thermal melting point (TM) for the specific sequence at a defined ionic strength and pH. The TM is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

"High stringency conditions" may comprise the following, e.g. Step 1: Filters containing DNA are pretreated for 8 hours to overnight at 65° C. in buffer composed of 6*SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5-20*10$^6$ cpm of $^{32}$P-labeled probe. Step 3: Filters are washed for 1 hour at 37° C. in a solution containing 2*SSC, 0.01% PVP, 0.01% Ficoll, and 0.01% BSA. This is followed by a wash in 0.1*SSC at 50° C. for 45 minutes. Step 4: Filters are autoradiographed. Other conditions of high stringency that may be used are well known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

"Moderate stringency conditions" can include the following: Step 1: Filters containing DNA are pretreated for 6 hours at 55° C. in a solution containing 6*SSC, 5*Denhardt's solution, 0.5% SDS and 100 mg/ml denatured salmon sperm DNA. Step 2: Filters are hybridized for 18-20 hours at 55° C. in the same solution with 5-20*10$^6$ cpm $^{32}$P-labeled probe added. Step 3: Filters are washed at 37° C. for 1 hour in a solution containing 2*SSC, 0.1% SDS, then washed twice for 30 minutes at 60° C. in a solution containing 1*SSC and 0.1% SDS. Step 4: Filters are blotted dry and exposed for autoradiography. Other conditions of moderate stringency that may be used are well-known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

Finally, "low stringency conditions" can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe. Step 3: Filters are washed for 1.5 hours at 55 C in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g. as employed for cross-species hybridizations). See e.g. Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

The nucleic acid sequences as defined above according to the present invention can be used to express peptides, i.e. an JNK inhibitor sequence as used herein or an chimeric peptide as used herein for analysis, characterization or therapeutic use; as markers for tissues in which the corresponding peptides (as used herein) are preferentially expressed (either constitutively or at a particular stage of tissue differentiation or development or in disease states). Other uses for these nucleic acids include, e.g. molecular weight markers in gel electrophoresis-based analysis of nucleic acids.

According to a further embodiment of the present invention, expression vectors may be used for the above purposes for recombinant expression of one or more JNK inhibitor sequences and/or chimeric peptides as defined above. The term "expression vector" is used herein to designate either circular or linear DNA or RNA, which is either double-stranded or single-stranded. It further comprises at least one nucleic acid as defined above to be transferred into a host cell or into a unicellular or multicellular host organism. The expression vector as used herein preferably comprises a nucleic acid as defined above encoding the JNK inhibitor sequence as used herein or a fragment or a variant thereof, or the chimeric peptide as used herein, or a fragment or a variant thereof. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, LCRs (e.g. described by Blackwood and Kadonaga (1998), Science 281, 61-63) or matrix/scaffold attachment regions (e.g. described by Li, Harju and Peterson, (1999), Trends Genet. 15, 403-408). In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more nucleic acid sequences as defined above, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured by any assay known in the art (see e.g. Wood, de Wet, Dewji, and DeLuca, (1984), Biochem Biophys. Res. Commun. 124, 592-596; Seliger and McElroy, (1960), Arch. Biochem. Biophys. 88, 136-141) or commercially available from Promega®).

An "enhancer region" to be used in the expression vector as defined herein, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-á-vis the gene to be expressed, and may be enhancing, augmenting, improving, or ameliorating expression of more than one promoter.

The promoter/enhancer sequences to be used in the expression vector as defined herein, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter). Alternatively, or in addition, they may include animal transcriptional control regions, e.g. (i) the insulin gene control region active within pancreatic beta-cells (see e.g. Hanahan, et al., 1985. Nature 315: 115-122); (ii) the immunoglobulin gene control region active within lymphoid cells (see e.g. Grosschedl, et al., 1984, Cell 38: 647-658); (iii) the albumin gene control region active within liver (see e.g. Pinckert, et al., 1987. Genes and Dev 1: 268-276; (iv) the myelin basic protein gene control region active within brain oligodendrocyte cells (see e.g. Readhead, et al., 1987, Cell 48: 703-712); and (v) the gonadotropin-releasing hormone gene control region active within the hypothalamus (see e.g. Mason, et al., 1986, Science 234: 1372-1378), and the like.

Additionally, the expression vector as defined herein may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD).

Exemplary expression vectors or their derivatives suitable for the present invention particularly include, e.g. human or animal viruses (e.g. vaccinia virus or adenovirus); insect viruses (e.g. baculovirus); yeast vectors; bacteriophage vectors (e.g. lambda phage); plasmid vectors and cosmid vectors.

The present invention additionally may utilize a variety of host-vector systems, which are capable of expressing the peptide coding sequence(s) of nucleic acids as defined above. These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Preferably, a host cell strain, suitable for such a host-vector system, may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptide. Moreover, different host cells possess characteristic and specific mechanisms for the translational and post-translational processing and modification (e.g. glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an non-glycosylated core peptide; whereas expression within mammalian cells ensures "native" glycosylation of a heterologous peptide.

The present invention further provides the use of antibodies directed against the JNK inhibitor sequences and/or chimeric peptides as described above, for preparing a pharmaceutical composition for the treatment of non-chronic or chronic inflammatory eye diseases as defined herein. Furthermore, efficient means for production of antibodies specific for JNK inhibitor sequences according to the present invention, or for chimeric peptides containing such an inhibitor sequence, are described and may be utilized for this purpose.

According to the invention, JNK inhibitor sequences and/or chimeric peptides as defined herein, as well as, fragments, variants or derivatives thereof, may be utilized as immunogens to generate antibodies that immunospecifically bind these peptide components. Such antibodies include, e.g. polyclonal, monoclonal, chimeric, single chain, Fab fragments and a Fab expression library. In a specific embodiment the present invention provides antibodies to chimeric peptides or to JNK inhibitor sequences as defined above. Various procedures known within the art may be used for the production of these antibodies.

By way of example, various host animals may be immunized for production of polyclonal antibodies by injection with any chimeric peptide or JNK inhibitor sequence as defined above. Various adjuvants may be used thereby to increase the immunological response which include, but are not limited to, Freund's (complete and incomplete) adjuvant, mineral gels (e.g. aluminum hydroxide), surface active substances (e.g. lysolecithin, pluronic polyols, polyanions, peptides, oil emulsions, dinitrophenol, etc.), CpG, polymers, Pluronics, and human adjuvants such as Bacille Calmette-Guerin and *Corynebacterium parvum*.

For preparation of monoclonal antibodies directed towards a chimeric peptide or a JNK inhibitor sequence as defined above, any technique may be utilized that provides for the production of antibody molecules by continuous cell line culture. Such techniques include, but are not limited to, the hybridoma technique (see Kohler and Milstein, 1975. Nature 256: 495-497); the trioma technique; the human B-cell hybridoma technique (see Kozbor, et al., 1983, Immunol Today 4: 72) and the EBV hybridoma technique to produce human monoclonal antibodies (see Cole, et al., 1985. In: Monoclonal Antibodies and Cancer Therapy, Alan R. Liss, Inc., pp. 77-96). Human monoclonal antibodies may be utilized in the practice of the present invention and may be produced by the use of human hybridomas (see Cote, et al., 1983. Proc Natl Acad Sci USA 80: 2026-2030) or by transforming human B-cells with Epstein Barr Virus in vitro (see Cole, et al., 1985. In: Monoclonal Antibodies and Cancer Therapy (Alan R. Liss, Inc.), pp. 77-96).

According to the invention, techniques can be adapted for the production of single-chain antibodies specific to the JNK inhibitor sequences and/or chimeric peptides (see e.g. U.S. Pat. No. 4,946,778) as defined herein. In addition, methods can be adapted for the construction of Fab expression libraries (see e.g. Huse et al., 1989. Science 246: 1275-1281) to allow rapid and effective identification of monoclonal Fab fragments with the desired specificity for these JNK inhibitor sequences and/or chimeric peptides. Non-human antibodies can be "humanized" by techniques well known in the art (see e.g. U.S. Pat. No. 5,225,539). Antibody fragments that contain the idiotypes to a JNK inhibitor sequences and/or chimeric peptide as defined herein may be produced by techniques known in the art including, e.g. (i) a F(ab')$_2$ fragment produced by pepsin digestion of an antibody molecule; (ii) a Fab fragment generated by reducing the disulfide bridges of an F(ab'), fragment; (iii) a Fab fragment generated by the treatment of the antibody molecule with papain and a reducing agent and (iv) Fv fragments.

In one embodiment of this invention, methods, that may be utilized for the screening of antibodies and which possess the desired specificity include, but are not limited to, enzyme-linked immunosorbent assay (ELISA) and other immunologically-mediated techniques known within the art. In a specific embodiment, selection of antibodies that are specific to a particular epitope of an JNK inhibitor sequence and/or an chimeric peptide as defined herein (e.g. a fragment thereof typically comprising a length of from 5 to 20, preferably 8 to 18 and most preferably 8 to 11 amino acids) is facilitated by generation of hybridomas that bind to the fragment of an JNK inhibitor sequence and/or an chimeric peptide, as defined herein, possessing such an epitope. These antibodies that are specific for an epitope as defined above are also provided herein.

The antibodies as defined herein may be used in methods known within the art referring to the localization and/or quantification of an JNK inhibitor sequence (and/or correspondingly to a chimeric peptide as defined above), e.g. for use in measuring levels of the peptide within appropriate physiological samples, for use in diagnostic methods, or for use in imaging the peptide, and the like.

The JNK inhibitor sequences, chimeric peptides, nucleic acids, vectors, host cells and/or antibodies as defined according to the invention can be formulated in a pharmaceutical composition, which may be applied in the prevention or treatment of any of the diseases as defined herein, particularly in the prevention or treatment of non-chronic or chronic inflammatory eye diseases as defined herein. Typically, such a pharmaceutical composition used according to the present invention includes as an active component, e.g.: (i) any one or more of the JNK inhibitor sequences and/or chimeric peptides as defined above, and/or variants, fragments or derivatives thereof, particularly JNK inhibitor sequences according to any of sequences of SEQ ID NOs: 1 to 4 and 13 to 20 and 33-100 and/or chimeric peptides according to any of sequences of SEQ ID NOs: 9 to 12 and 23 to 32, and/or JNK inhibitor sequences according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions; and/or (ii) nucleic acids encoding an JNK inhibitor sequence and/or an chimeric peptide as defined above and/or variants or fragments thereof, and/or (iii) cells comprising any one or more of the JNK inhibitor sequences and/or chimeric peptides, and/or variants, fragments or derivatives thereof, as defined above and/or (iv) cells transfected with a vector and/or nucleic acids encoding an JNK inhibitor sequence and/or an chimeric peptide as defined above and/or variants or fragments thereof.

According to a preferred embodiment, such a pharmaceutical composition as used according to the present invention typically comprises a safe and effective amount of a component as defined above, preferably of at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5-8 and 21 to 22, or variants or fragments thereof within the above definitions, or at least one nucleic acids encoding same, or at least one vector, host cell or antibody as defined above.

The amount of a JNK-inhibitor sequence and chimeric peptide, respectively, in the pharmaceutical composition to be administered to a subject, may—without being limited thereto—have a very low dose. Thus, the dose may be much lower than for peptide drugs known in the art, such as DTS-108 (Florence Meyer-Losic et al., Clin Cancer Res., 2008, 2145-53). This has several positive aspects, for example a reduction of potential side reactions and a reduction in costs.

Preferably, the dose (per kg bodyweight) is in the range of up to 10 mmol/kg, preferably up to 1 mmol/kg, more preferably up to 100 µmol/kg, even more preferably up to 10 µmol/kg, even more preferably up to 1 µmol/kg, even more preferably up to 100 nmol/kg, most preferably up to 50 nmol/kg.

Thus, the dose range may preferably be from about 1 pmol/kg to about 1 mmol/kg, from about 10 pmol/kg to about 0.1 mmol/kg, from about 10 pmol/kg to about 0.01 mmol/kg, from about 50 pmol/kg to about 1 µmol/kg, from about 100 pmol/kg to about 500 nmol/kg, from about 200 pmol/kg to about 300 nmol/kg, from about 300 pmol/kg to about 100 nmol/kg, from about 500 pmol/kg to about 50 nmol/kg, from about 750 pmol/kg to about 30 nmol/kg, from about 250 pmol/kg to about 5 nmol/kg, from about 1 nmol/kg to about 10 nmol/kg, or a combination of any two of said values.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980. Accordingly, a "safe and effective amount" as defined above for components of the pharmaceutical compositions as used according to the present invention means an amount of each or all of these components, that is sufficient to significantly induce a positive modification of a non-chronic or chronic inflammatory eye diseases as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of such a component will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

The pharmaceutical composition as used according to the present invention may furthermore comprise, in addition to one of these substances, a (compatible) pharmaceutically acceptable carrier, excipient, buffer, stabilizer or other materials well known to those skilled in the art.

In this context, the expression "(compatible) pharmaceutically acceptable carrier" preferably includes the liquid or non-liquid basis of the composition. The term "compatible" means that the constituents of the pharmaceutical composition as used herein are capable of being mixed with the pharmaceutically active component as defined above and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated.

If the pharmaceutical composition as used herein is provided in liquid form, the pharmaceutically acceptable carrier will typically comprise one or more (compatible) pharmaceutically acceptable liquid carriers. The composition may comprise as (compatible) pharmaceutically acceptable liquid carriers e.g. pyrogen-free water; isotonic saline or buffered (aqueous) solutions, e.g. phosphate, citrate etc. buffered solutions, vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid, etc. Particularly for injection of the pharmaceutical composition as used herein, a buffer, preferably an aqueous buffer, may be used.

If the pharmaceutical composition as used herein is provided in solid form, the pharmaceutically acceptable carrier will typically comprise one or more (compatible) pharmaceutically acceptable solid carriers. The composition may comprise as (compatible) pharmaceutically acceptable solid carriers e.g. one or more compatible solid or liquid fillers or diluents or encapsulating compounds may be used as well, which are suitable for administration to a person. Some examples of such (compatible) pharmaceutically acceptable solid carriers are e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulphate, etc.

The precise nature of the (compatible) pharmaceutically acceptable carrier or other material may depend on the route of administration. The choice of a (compatible) pharmaceutically acceptable carrier may thus be determined in principle by the manner in which the pharmaceutical composition as used according to the invention is administered. The pharmaceutical composition as used according to the invention can be administered, for example, systemically. Routes for administration include, for example, parenteral routes (e.g. via injection), such as intravenous, intramuscular, subcutaneous, intradermal, or transdermal routes, etc., enteral routes, such as oral, or rectal routes, etc., topical routes, such as nasal, or intranasal routes, etc., or other routes, such as epidermal routes or patch delivery. Particularly preferred is also the local administration at/in the eye, e.g. intravitreous administration, subconjuntival administration and/or instillation.

The suitable amount of the pharmaceutical composition to be used can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the compound is to be administered perorally, tablets, capsules and the like are the preferred unit dose form. The pharmaceutically acceptable carriers for the preparation of unit dose forms, which can be used for oral administration are well known in the prior art. The choice thereof will depend on secondary considerations such as taste, costs and storability, which are not critical for the purposes of the present invention, and can be made without difficulty by a person skilled in the art.

Pharmaceutical compositions for oral administration may be in tablet, capsule, powder or liquid form. A tablet may include a solid carrier as defined above, such as gelatin, and optionally an adjuvant. Liquid pharmaceutical compositions for oral administration generally may include a liquid carrier as defined above, such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated.

Prevention and/or treatment of a disease as defined herein typically includes administration of a pharmaceutical composition as defined above. The term "modulate" includes the suppression of expression of JNK when it is over-expressed in any of the above diseases. It also includes, without being limited thereto, suppression of phosphorylation of c-jun, ATF2 or NFAT4 in any of the above diseases, for example, by using at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, as a competitive inhibitor of the natural c-jun, ATF2 and NFAT4 binding site in a cell. The term "modulate" also includes suppression of hetero- and homomeric complexes of transcription factors made up of, without being limited thereto, c-jun, ATF2, or NFAT4 and their related partners, such as for example the AP-1 complex that is made up of c-jun, AFT2 and c-fos. When a non-chronic or chronic inflammatory eye disease is associated with JNK overexpression, such suppressive JNK inhibitor sequences can be introduced to a cell. In some instances, "modulate" may then include the increase of JNK expression, for example by use of an IB peptide-specific antibody that blocks the binding of an IB-peptide to JNK, thus preventing JNK inhibition by the IB-related peptide.

Prevention and/or treatment of a subject with the pharmaceutical composition as disclosed above may be typically accomplished by administering (in vivo) an ("therapeutically effective") amount of said pharmaceutical composition to a subject, wherein the subject may be e.g. any mammal, e.g. a human, a primate, mouse, rat, dog, cat, cow, horse or pig. The term "therapeutically effective" means that the active component of the pharmaceutical composition is of sufficient quantity to ameliorate the non-chronic or chronic inflammatory eye disease.

Accordingly, peptides as defined above, e.g. at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, may be utilized in a specific embodiment of the present invention to treat non-chronic or chronic inflammatory eye diseases.

Peptides as defined above and as contained in the inventive pharmaceutical composition may be also encoded by nucleic acids. This is particularly advantageous, if the above peptides are administered for the purpose of gene therapy. In this context, gene therapy refers to therapy that is performed by administration of a specific nucleic acid as defined above to a subject, e.g. by way of a pharmaceutical composition as defined above, wherein the nucleic acid(s) exclusively comprise(s) L-amino acids. In this embodiment of the present invention, the nucleic acid produces its encoded peptide(s), which then serve(s) to exert a therapeutic effect by modulating function of the disease or disorder. Any of the methods relating to gene therapy available within the art may be used in the practice of the present invention (see e.g. Goldspiel, et al., 1993. Clin Pharm 12: 488-505).

In a preferred embodiment, the nucleic acid as defined above and as used for gene therapy is part of an expression vector encoding and expressing any one or more of the IB-related peptides as defined above within a suitable host, i.e. an JNK inhibitor sequence according to any of sequences of SEQ ID NOs: 1 to 4 and 13 to 20 and 33-100 and/or a chimeric peptide according to any of sequences of SEQ ID NOs: 9 to 12 and 23 to 32, and/or an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions. In a specific embodiment, such an expression vector possesses a promoter that is operably-linked to coding region(s) of a JNK inhibitor sequence. The promoter may be defined as above, e.g. inducible or constitutive, and, optionally, tissue-specific.

In another specific embodiment, a nucleic acid molecule as defined above is used for gene therapy, in which the coding sequences of the nucleic acid molecule (and any other desired sequences thereof) as defined above are flanked by regions that promote homologous recombination at a desired site within the genome, thus providing for intra-chromosomal expression of these nucleic acids (see e.g. Koller and Smithies, 1989. Proc Natl Acad Sci USA 86: 8932-8935).

Delivery of the nucleic acid as defined above according to the invention into a patient for the purpose of gene therapy, particular in the context of the above mentioned non-chronic or chronic inflammatory eye diseases as defined above may be either direct (i.e. the patient is directly exposed to the nucleic acid or nucleic acid-containing vector) or indirect (i.e. cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g. constructing the nucleic acid as part of an appropriate nucleic acid expression vector and administering the same in a manner such that it becomes intracellular (e.g. by infection using a defective or attenuated retroviral or other viral vector; see U.S. Pat. No. 4,980,286); directly injecting naked DNA; using microparticle bombardment (e.g. a "GeneGun"; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see e.g. Wu and Wu, 1987.J Biol Chem 262: 4429-4432), which can be used to "target" cell types that specifically express the receptors of interest, etc.

An additional approach to gene therapy in the practice of the present invention involves transferring a nucleic acid as defined above into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g. antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including e.g. transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methods that ensure that the necessary developmental and physiological functions of the recipient cells are not disrupted by the transfer. See e.g. Loeffler and Behr, 1993. Meth Enzymol 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g. injection of epithelial cells (e.g. subcutaneously), application of recombinant skin cells as a skin graft onto the patient, and intravenous injection of recombinant blood cells (e.g. hematopoietic stem or progenitor cells). The total amount of cells that are envisioned for use depend upon the desired effect, patient state, and the like, and may be determined by one skilled within the art. Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g. as obtained from bone marrow, umbilical cord blood, peripheral blood, fetal liver, and the like. In a preferred embodiment, the cells utilized for gene therapy are autologous to the patient.

Alternatively and/or additionally, for treating diseases as mentioned herein targeting therapies may be used to deliver the JNK inhibitor sequences, chimeric peptides, and/or nucleic acids as defined above more specifically to certain types of cell, by the use of targeting systems such as (a targeting) antibody or cell specific ligands. Antibodies used for targeting are typically specific for cell surface proteins of cells associated with any of the diseases as defined below. By way of example, these antibodies may be directed to cell surface antibodies such as e.g. B cell-associated surface proteins such as MHC class II DR protein, CD18 (LFA-1 beta chain), CD45RO, CD40 or Bgp95, or cell surface proteins selected from e.g. CD2, CD2, CD4, CD5, CD7, CD8, CD9, CD10, CD13, CD16, CD19, CD20, CD21, CD22, CD23, CD24, CD25, CD30, CD33, CD34, CD38, CD39, CD4, CD43, CD45, CD52, CD56, CD68, CD71, CD138, etc. Targeting constructs may be typically prepared by covalently binding the JNK inhibitor sequences, chimeric peptides, and nucleic acids as defined herein according to the invention to an antibody specific for a cell surface protein or by binding to a cell specific ligand. Proteins may e.g. be bound to such an antibody or may be attached thereto by a peptide bond or by chemical coupling, crosslinking, etc. The targeting therapy may then be carried out by administering the targeting construct in a pharmaceutically efficient amount to a patient by any of the administration routes as defined below, e.g. intraperitoneal, nasal, intravenous, oral and patch delivery routes. Preferably, the JNK inhibitor sequences, chimeric peptides, or nucleic acids as defined herein according to the invention, being attached to the targeting antibodies or cell specific ligands as defined above, may be released in vitro or in vivo, e.g. by hydrolysis of the covalent bond, by peptidases or by any other suitable method. Alternatively, if the JNK inhibitor sequences, chimeric peptides, or nucleic acids as defined herein according to the invention are attached to a small cell specific ligand, release of the ligand may not be carried out. If present at the cell surface, the chimeric peptides may enter the cell upon the activity of its trafficking sequence. Targeting may be desirable for a variety of reasons; for example if the JNK inhibitor sequences, chimeric peptides, and nucleic acids as defined herein according to the invention are unacceptably toxic or if it would otherwise require a too high dosage.

Instead of administering the JNK inhibitor sequences and/or chimeric peptides as defined herein according to the invention directly, they could be produced in the target cells by expression from an encoding gene introduced into the cells, e.g. from a viral vector to be administered. The viral vector typically encodes the JNK inhibitor sequences and/or chimeric peptides as defined herein according to the invention. The vector could be targeted to the specific cells to be treated. Moreover, the vector could contain regulatory elements, which are switched on more or less selectively by the target cells upon defined regulation. This technique represents a variant of the VDEPT technique (virus-directed enzyme prodrug therapy), which utilizes mature proteins instead of their precursor forms.

Alternatively, the JNK inhibitor sequences and/or chimeric peptides as defined herein could be administered in a precursor form by use of an antibody or a virus. These JNK inhibitor sequences and/or chimeric peptides may then be converted into the active form by an activating agent produced in, or targeted to, the cells to be treated. This type of approach is sometimes known as ADEPT (antibody-directed enzyme prodrug therapy) or VDEPT (virus-directed enzyme prodrug therapy); the former involving targeting the activating agent to the cells by conjugation to a cell-specific antibody, while the latter involves producing the activating agent, e.g. a JNK inhibitor sequence or the chimeric peptide, in a vector by expression from encoding DNA in a viral vector (see for example, EP-A-415731 and WO 90/07936).

According to a further embodiment, the JNK inhibitor sequences, chimeric peptides, nucleic acid sequences or antibodies to JNK inhibitor sequences or to chimeric peptides as defined herein, e.g. an JNK inhibitor sequence according to any of sequences of SEQ ID NOs: 1 to 4 and 13 to 20 and 33-100 and/or a chimeric peptide according to any of sequences of SEQ ID NOs: 9 to 12 and 23 to 32, and/or an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, may be utilized in (in vitro) assays (e g immunoassays) to detect, prognose, diagnose, or monitor various conditions and disease states selected from non-chronic or chronic inflammatory eye diseases as defined above, or monitor the treatment thereof. The immunoassay may be performed by a method comprising contacting a sample derived from a patient with an antibody to an JNK inhibitor sequence, a chimeric peptide, or a nucleic acid sequence, as defined above, under conditions such that immunospecific-binding may occur, and subsequently detecting or measuring the amount of any immunospecific-binding by the antibody. In a specific embodiment, an antibody specific for an JNK inhibitor sequence, a chimeric peptide or a nucleic acid sequence may be used to analyze a tissue or serum sample from a patient for the presence of JNK or a JNK inhibitor sequence; wherein an aberrant level of JNK is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc. Alternatively, (in vitro) assays may be performed by delivering the JNK inhibitor sequences, chimeric peptides, nucleic acid sequences or antibodies to JNK inhibitor sequences or to chimeric peptides, as defined above, to target cells typically selected from e.g. cultured animal cells, human cells or micro-organisms, and to monitor the cell response by biophysical methods typically known to a skilled person. The target cells typically used therein may be cultured cells (in vitro) or in vivo cells, i.e. cells composing the organs or tissues of living animals or humans, or microorganisms found in living animals or humans.

The present invention additionally provides the use of kits for diagnostic or therapeutic purposes, particular for the treatment, prevention or monitoring of non-chronic or chronic inflammatory eye diseases as defined above, wherein the kit includes one or more containers containing JNK inhibitor sequences, chimeric peptides, nucleic acid sequences and/or antibodies to these JNK inhibitor sequences or to chimeric peptides as defined above, e.g. an anti-JNK inhibitor sequence antibody to an JNK inhibitor sequence according to any of sequences of SEQ ID NOs: 1 to 4 and 13 to 20 and 33-100, to a chimeric peptide according to any of sequences of SEQ ID NOs: 9 to 12 and 23 to 32, to an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or to or variants or fragments thereof within the above definitions, or such an anti-JNK inhibitor sequence antibody and, optionally, a labeled binding partner to the antibody. The label incorporated thereby into the antibody may include, but is not limited to, a chemiluminescent, enzymatic, fluorescent, colorimetric or radioactive moiety. In another specific embodiment, kits for diagnostic use in the treatment, prevention or monitoring of non-chronic or chronic inflammatory eye diseases as defined above are provided which comprise one or more containers containing nucleic acids that encode, or alternatively, that are the complement to, an JNK inhibitor sequence and/or a chimeric peptide as defined above, optionally, a labeled binding partner to these nucleic acids, are also provided. In an alternative specific embodiment, the kit may be used for the above purposes as a kit, comprising one or more containers, a pair of oligonucleotide primers (e.g. each 6-30 nucleotides in length) that are capable of acting as amplification primers for polymerase chain reaction (PCR; see e.g. Innis, et al., 1990. PCR PROTOCOLS, Academic Press, Inc., San Diego, Calif.), ligase chain reaction, cyclic probe reaction, and the like, or other methods known within the art used in context with the nucleic acids as defined above. The kit may, optionally, further comprise a predetermined amount of a purified JNK inhibitor sequence as defined above, a chimeric peptide as defined above, or nucleic acids encoding these, for use as a diagnostic, standard, or control in the assays for the above purposes.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

Immunohistochemistry against SEQ ID NO: 11 was carried out on ocular histological sections from untreated and IV or IVT injected animals (vehicle or SEQ ID NO: 11), both in (A-L) healthy and (M-W) LPS-induced inflammatory conditions (n=3 eyes analyzed per condition; time point: 24 h). (A-C) SEQ ID NO: 11 was undetectable in ocular tissues 24 hours after IV injection in healthy eyes. (D-L) After IVT injection in healthy eyes, SEQ ID NO: 11 was found in iris epithelium (D, G), ciliary body epithelium (E, J), GCL (H), INL (K), IS (I) and RPE (L). In eyes with uveitis, SEQ ID NO: 11 was detected in infiltrating inflammatory cells after IV injection of SEQ ID NO: 11 (M-P), but not after IV or IVT injections of vehicle (not shown) or in untreated EIU eyes (V,W). (Q-U) In uveitic eyes treated by IVT of SEQ ID NO: 11, distribution of SEQ ID NO: 11 was similar to that of healthy treated eyes but was also detected in migrating resident inflammatory cells (S-T). Scale bar: 50 µm. c: cornea; ir: iris; l: lens; cb: ciliary body; st: stroma; ep: epithelium; GCL: ganglion cell layer; INL: inner nuclear layer; ONL: outer nuclear layer; RPE: retinal pigment epithelium; IS: photoreceptor inner segment; aq. h: aqueous humor.

Figure 5:
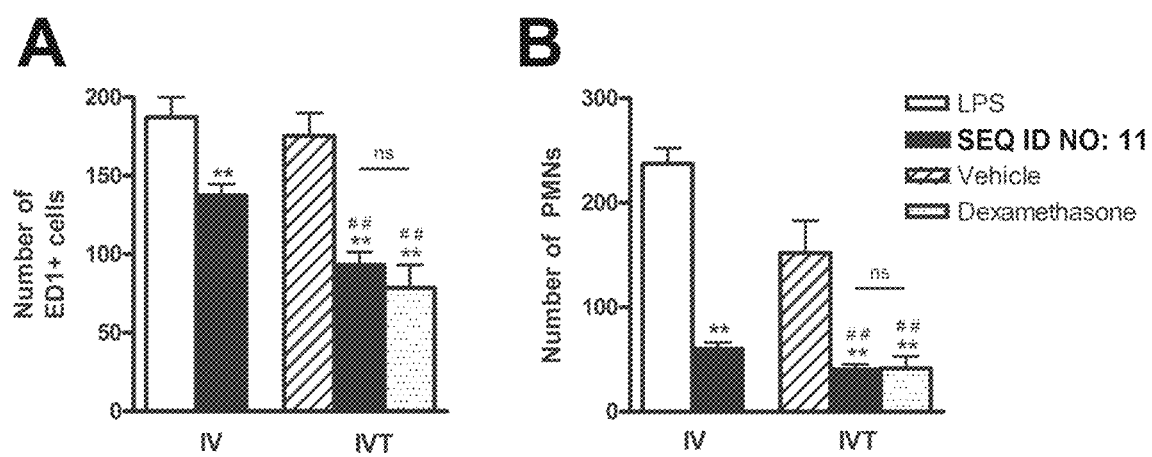
Figure 6:
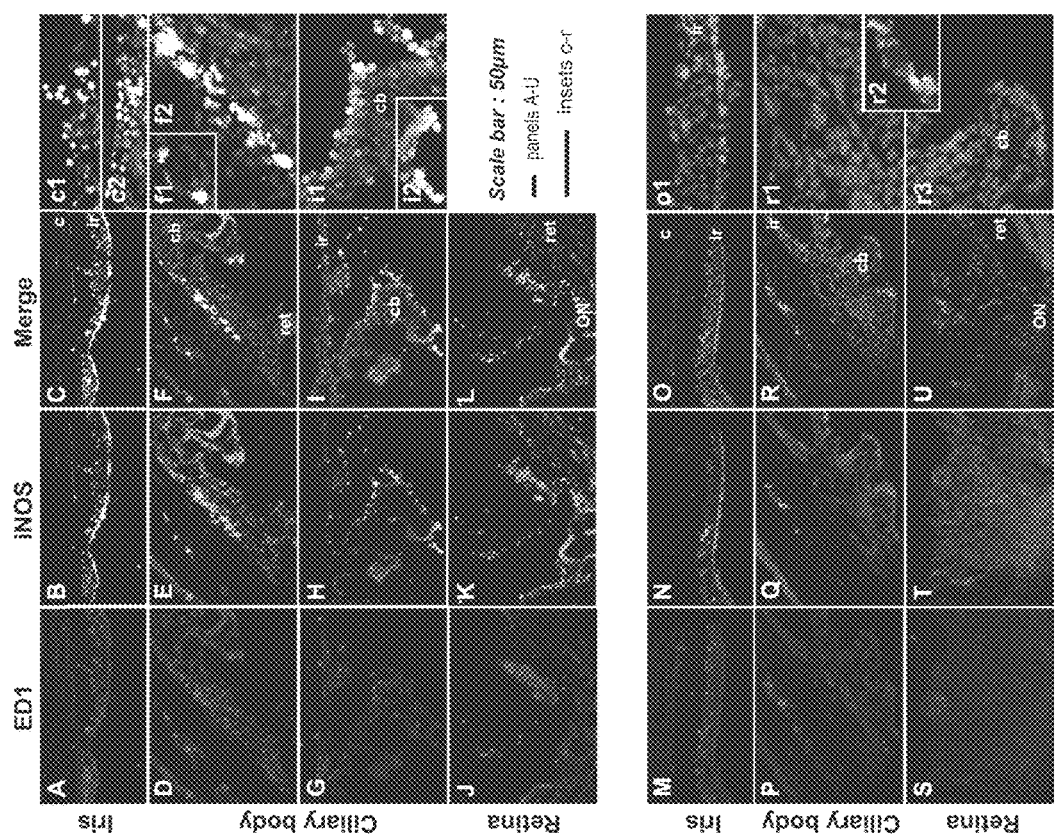

FIG. 5 Reduction of LPS-induced inflammatory cell infiltration by the JNK-inhibitor (poly-)peptide of SEQ ID NO: 11:

Infiltration of (A) macrophages (ED1 immunopositive cells) and (B) polymorphonuclear leukocytes (PMNs) was quantified on histological sections (n=6 sections per group) stained by immunohistochemistry (illustrated on FIG. 6). (A) Intravenous (IV) (p<0.005 vs LPS) and intravitreous (IVT) ( p<0.005 vs LPS; ##p<0.009 vs Vehicle) injections of the (poly-)peptide of SEQ ID NO: 11 reduced the number of ED1+. (B) the (poly-)peptide of SEQ ID NO: 11 decreased the number of PMNs after intravenous (IV) (p<0.005 vs LPS) and intravitreous (IVT) (p<0.005 vs LPS; ##p<0.009 vs Vehicle) administrations. No statistical difference (ns) was observed between IVT of the (poly-)peptide of SEQ ID NO: 11 and dexamethasone that was used as a positive control.

FIG. 6 Effect of the (poly-)peptide of SEQ ID NO: 11 on ED1+ cells, polymorphonuclear leukocytes and inducible nitric oxide synthase (iNOS) expression in LPS-induced uveitis:

ED1 and iNOS antigens expression was analyzed by immunohistochemistry on eye cryosections of untreated or treated (IV or IVT, vehicle or SEQ ID NO: 11) uveitic rats (n=3 eyes per condition; time point: 24 h). Nuclei were stained with DAPI. Numerous inflammatory cells expressing ED1 (A, D, G, J) and/or iNOS (B, E, H, K) infiltrated the anterior (A-I) and the posterior segment (J-L) of untreated EIU eyes. A few number of ED1+/iNOS+ cells were found in the iris/ciliary body (yellow cells, panels c1-2 and f1-2) but most iNOS+ cells were ED-cells suggesting that mostly PMNs produced iNOS. IV (M-U) and IVT (not shown) injections of SEQ ID NO:11 reduced the inflammatory infiltrate expressing ED1 (M, P, S) and iNOS (N, Q, T). In eyes treated by IV (M-U) and IVT (not shown) of SEQ ID NO:11, a reduced number of ED1+ cells (M, P, S) and iNOS+ cells (N, Q, T) was observed. Scale bar: 50 µm. c: cornea; ir: iris; cb: ciliary body; ret: retina; ON: optic nerve.

Figure 7:
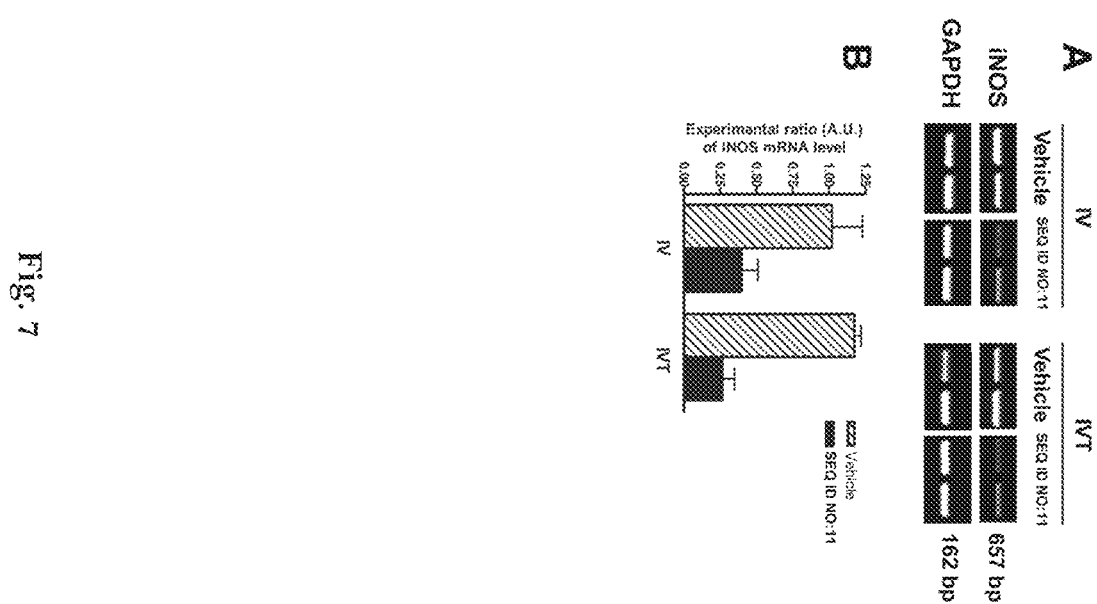
Figure 8A:
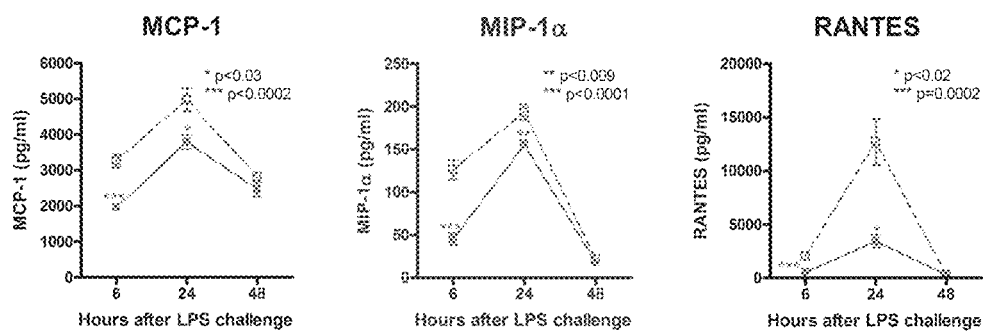
Figure 8B:
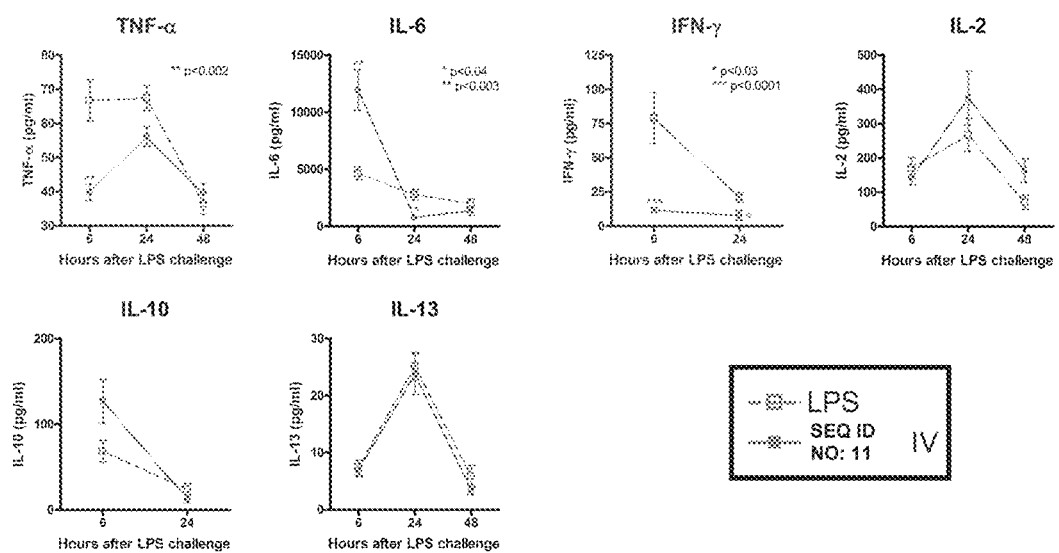

FIG. 7 Down-regulation of LPS-induced iNOS expression by the (poly-)peptide of SEQ ID NO: 11:

RT-PCR analysis of inducible nitric oxide synthase (iNOS) mRNA levels in neuroretinas 24 hours after IV or IVT injections of SEQ ID NO:11 or vehicle (n=2 eyes per group) in EIU conditions. Down-regulation of iNOS mRNA was visualized on (A) agarose gel under ultraviolet transilluminator (upper lane: 657 bp iNOS cDNA amplification product; bottom lane: 162 bp GAPDH cDNA amplification product) and confirmed by (B) densitometric quantitation FIGS. 8A and 8B Modulation of intraocular LPS-induced Chemokine/Cytokine profiles following intravenous (IV) administration of (poly-)peptide of SEQ ID NO: 11: Multiplex analysis was performed on ocular fluids collected 6 h, 24 h and 48 h after EIU induction. Comparison was made between uninjected control uveitic rats or with (poly-)peptide of SEQ ID NO: 11 IV treated rats (n=10 eyes analyzed per time point and per condition). Results from rats treated by IV injection of vehicle were not represented for more clarity. P values of statistical analysis are indicated on each graph (p). IV injection of (poly-)peptide of SEQ ID NO: 11 decreased chemokines production (FIG. 8A), and decreased pro-inflammatory and Th1 cytokines production at specific time points (FIG. 8B). Levels of IFN-γ and IL-10 were not represented at 48 h because of being below detectable levels.

Figure 9A:
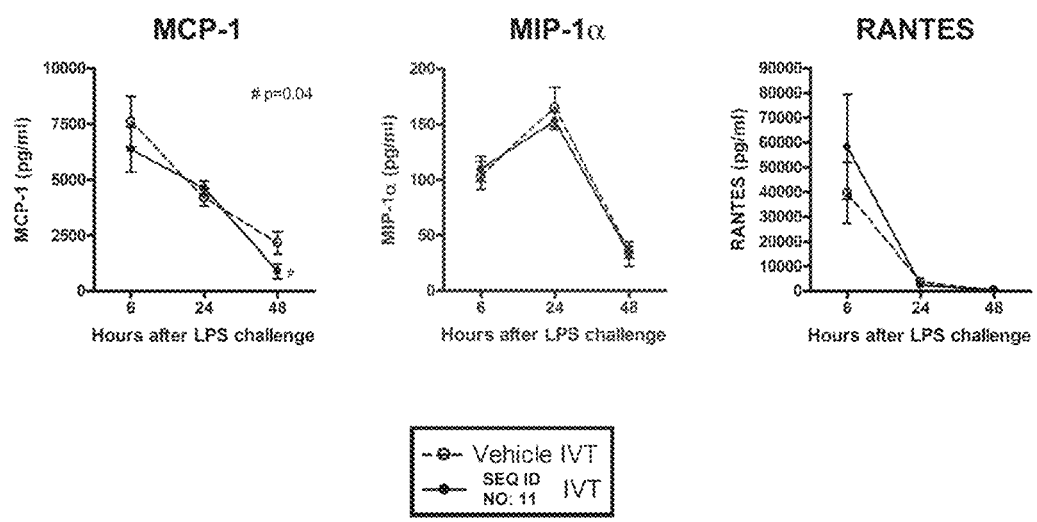
Figure 9B:
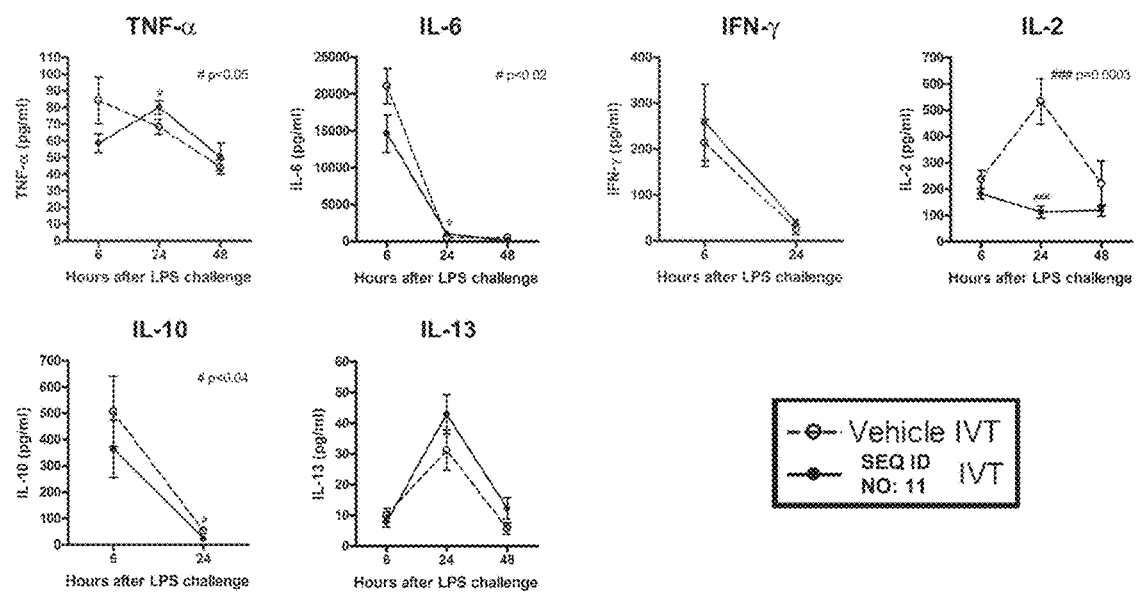

FIGS. 9A and 9B Modulation of intraocular LPS-induced Chemokine/Cytokine profiles following intravitreous (IVT) administration of (poly-)peptide of SEQ ID NO: 11: Multiplex analysis was performed on ocular fluids collected 6 h, 24 h and 48 h after EIU induction. Comparison was made between rats treated by IVT injection of vehicle and (poly-)peptide of SEQ ID NO: 11 (n=10 eyes analyzed per time point and per condition). P values of statistical analysis are indicated on each graph (p). No significant changes were observed on chemokines expression between vehicle IVT or (poly-)peptide of SEQ ID NO: 11 IVT injections except a decrease of MCP-1 (FIG. 9A). Little changes in cytokines expression were induced by IVT injection of the (poly-)peptide of SEQ ID NO: 11: lower levels of TNF-α, IL-6 and IL-2 at 6 hours, a lower level of IL-2 and a greater level of IL-13 at 24 hours (FIG. 9A).

FIG. 10 shows the the IB1 cDNA sequence from rat and its predicted amino acid sequence (SEQ ID NO:102)

FIG. 11 shows the IB1 protein sequence from rat encoded by the exon-intron boundary of the rIB1 gene-splice donor (SEQ ID NO:103)

FIG. 12 shows the IB1 protein sequence from *Homo sapiens* (SEQ ID NO:104)

FIG. 13 shows the IB1 cDNA sequence from *Homo sapiens* (SEQ ID NO:105)

EXAMPLES

Example 1

Solutions and Products

An all-D-retro-inverso JNK-inhibitor (poly-)peptide of SEQ ID NO: 11 was produced by Polypeptide Laboratories (France) and purified by High Performance Liquid Chromatography (HPLC). It was analyzed by mass spectrometry for identity and RP-HPLC for purity (Polypeptide Laboratories, France). Once lyophilized, the powder was stored at 2-8° C. One day prior to the experiment, the JNK-inhibitor (poly-)peptide of SEQ ID NO: 11 powder was dissolved under sterile conditions at the concentration of 10 µM in saline (NaCl 0.9%, Versol®, Aguettant) in a National Scientific (NSC) deactivated glass vial (NSC-C4015-S1) and stored at 4° C. until use.

For each experiment, a fraction of freshly dissolved the JNK-inhibitor (poly-)peptide of SEQ ID NO: 11 was stored at −20° C. and its concentration was confirmed by High Performance Liquid Chromatography (HPLC) analysis.

Dexamethasone sodium phosphate 4 mg/mL (Soludecadron; Laboratoire Roussel, Paris, France) was used as positive control for anti inflammatory activity on EIU.10

Animals 7 weeks old female Lewis rats weighing 175 g (Elevage Janvier, Le Genest Saint Isle, France) were used and handled in accordance with the ARVO Statement for the Use of Animals in Ophthalmic and Vision Research. Rats were anesthetized with intramuscular injection of Ketamine (88 mg/kg) (Virbac, France) and Largactil (0.6 mg/kg) (Sanofi-Aventis, France) before intravenous or ocular injection.

Injections

For intravenous (IV) injection, 100 µL of saline (NaCl 0.9%) or the JNK-inhibitor (poly-)peptide of SEQ ID NO:

11 (20 µg/kg in saline) were injected in a tail vein using a 25G-needle connected on a 1 mL syringe (Becton Dickinson, France). For intravitreous (IVT) injection, 5 µL of saline or the JNK-inhibitor (poly-)peptide of SEQ ID NO: 11 (0.2 µg/injection in saline) were injected in both eyes using a 30G disposable needle (BD-microfine syringe, nm Médical, Asnière, France). The IV dose of 20 µg/kg (i.e. 3.5 µg/rat in rats weighing 175 g) was chosen according to studies showing that the JNK-inhibitor (poly-)peptide of SEQ ID NO: 11 is active at very low doses in other models. For intravitreous injections, the inventors used the minimal dose used in direct ear application after acute noise trauma in patients. This corresponds to 5% of the dose injected intravenously. Immediately after intravenous or intravitreous treatment, Endotoxin-Induced Uveitis (EIU) was induced by a single footpad injection of 100 µL sterile pyrogen-free saline containing 200 µg of LPS (Lipopolysaccharides from Salmonella typhimurium, Sigma-Aldrich, Saint-Quentin Fallavier, France). At the end the experiments, i.e. 6, 24 or 48 h after LPS challenge, rats were anesthetized by intraperitoneal injection of pentobarbital (30 mg/kg) (Sanofi-Aventis, France) before blood was collected by intracardiac puncture. Rats were then killed with a lethal dose of pentobarbital and both eyes were enucleated.

Samples Collection

Aqueous humor and vitreous were collected and pooled from each enucleated eye. Ocular fluids were immediately centrifuged and the cell-free fractions were collected and frozen at −20° C. before analysis by Multiplex assay. Blood samples were first clotted at room temperature for 2 hours and then at 4° C. overnight. Serum was collected, centrifuged and the clear supernatant was collected and frozen at −20° C. before Multiplex analysis.

Retinas and RPE/choroid/sclera complexes were carefully dissected out on enucleated eyes, snap frozen and stored at −80° C. until being used for RT-PCR and Western-Blot analyses.

For immunohistochemistry, eyeballs were collected and fixed for 1 h at room temperature in phosphate buffered saline (PBS) containing 4% paraformaldehyde before being rinsed overnight in PBS. The next day, samples were embedded and frozen in optimal cutting-temperature (OCT) compound (Tissue-Tek®, Sakura Finetek, Zoeterwoude, Netherland) and stored at −80° C. Frozen antero-posterior sections of eyes (10 µm thick) were performed at the optic nerve level using a cryostat (Leica CM 3050S, Rueil-Malmaison, France) and mounted on super-frost slides for immunohistochemical analysis.

Experimental Design

In a first set of experiment, 70 rats were randomized into 14 experimental groups with 5 rats per group. Uveitis was induced in each group and rats were killed 6 hours (4 groups), 24 hours (6 groups) and 48 hours (4 groups) after LPS challenge. For each time point tested (i.e. 6 h, 24 h and 48 h), rats treated by intravenous or intravitreous injections of vehicle (NaCl 0.9%) or the JNK-inhibitor (poly-)peptide of SEQ ID NO: 11 were compared to untreated control uveitic rats. Two additional groups, treated by intravenous injection of vehicle and intravitreal injection of dexamethasone were used at 24 hours. Clinical ocular inflammation was recorded only at 24 hours (see Scoring of Endotoxin-Induced Uveitis (EIU) section). At each time point, intraocular fluids from each eye (n=10 per group) and serum from each animal (n=5 per group) were used for Chemokine/Cytokine Multiplex Assay.

Retinas and RPE/choroid/sclera complexes were also collected at 24 hours to analyze iNOS mRNA levels by RT-PCR and c-Jun phosphorylation state by Western-Blot. Tissues were collected only from eyes treated by IV (intravenous) injection of vehicle, IV injection of the JNK-inhibitor (poly-)peptide of SEQ ID NO: 11, IVT (intravitreal) injection of vehicle and IVT injection of the JNK-inhibitor (poly-)peptide of SEQ ID NO: 11 (n=2 eyes per condition collected from separate rats). Eyes were selected so that their EIU clinical score was representative of the mean of the experimental group they belong to, i.e 3 for eyes treated by IV and IVT injection of vehicle and 2 for eyes treated by IV or IVT injection of the JNK-inhibitor (poly-)peptide of SEQ ID NO: 11.

A second set of experiment was designed to evaluate the anti-inflammatory effect of the JNK-inhibitor (poly-)peptide of SEQ ID NO: 11 at the cellular and tissue level as well as the biodistribution of this molecule 24 hours after administration. Rats were randomized into 11 experimental groups. 6 groups of rats with uveitis: untreated uveitic rats, rats injected intravenously with NaCl or the JNK-inhibitor (poly-)peptide of SEQ ID NO: 11 and rats injected intravitreously with the vehicle, the JNK-inhibitor (poly-)peptide of SEQ ID NO: 11 or dexamethasone. The 5 additional groups without uveitis were: untreated healthy rats, rats treated by NaCl IV or the JNK-inhibitor (poly-)peptide of SEQ ID NO: 11 IV and rats injected IVT with NaCl or the JNK-inhibitor (poly-)peptide of SEQ ID NO: 11. Three eyes from separate rats were collected per group and used for immunohistochemistry.

Note that, for clinical and histological analyses, dexamethasone was used as a reference treatment.

Scoring of Endotoxin-Induced Uveitis (EIU)

Animals were examined by slit lamp at 24 hours, the clinical peak of the disease in our experiments. The intensity of clinical ocular inflammation was scored on a scale from 0 to 5 for each eye as described previously10: grade (0) indicates no inflammation; grade (1) indicates the presence of a minimal iris and conjunctival vasodilation but without the observation of flare or cells in the anterior chamber (AC); grade (2) indicates the presence of moderate iris and conjunctival vessel dilation but without evident flare or cells in the AC; grade (3) indicates the presence of intense iris vessels dilation, flare and less than 10 cells per slit lamp field in the AC; grade (4) indicates the presence of more severe clinical signs than grade 3, with more than 10 cells in the AC with or without the formation of a hypopion; grade (5) indicates the presence of intense inflammatory reaction, fibrin formation in the AC and total seclusion of the pupil. Clinical evaluation was performed in a masked manner.

Western-Blot Analysis

RPE/choroid/sclera complexes and neuroretinas (2 per experimental group) were snap frozen immediately after dissection and stored at −80° C. until use. Tissues were homogenized in 500 µL, of lysis buffer (MOPS SDS Running Buffer, Invitrogen, Cergy-Pontoise, France) supplemented with protease inhibitor cocktail (Roche Diagnostics, Meylan, France) (one tablet for 50 mL). After addition of LDS Sample Buffer (Invitrogen) and heating for 5 min at 100° C., equal amounts of proteins were subjected to electrophoresis in a NuPAGE 4-12% Bis-Tris gel (Invitrogen) using MOPS SDS Running Buffer. The bands obtained were then electrotransferred onto nitrocellulose membranes (Schleicher & Schnell BioScience, Dassel, Germany).

Western-blot analyses were carried out to analyze the effect of the JNK-inhibitor (poly-)peptide of SEQ ID NO: 11 on the three mitogen-activated protein kinase (MAPK) pathways. To analyze the JNK pathway, blots were sequentially incubated with a rabbit Phospho-c-Jun (Ser63) primary antibody (or Phospho-c-Jun (Ser73) antibody) and an anti-rabbit IgG HRP-linked secondary antibody according to the manufacturer's instruction (PhosphoPlus c-Jun (Ser63) II and c-Jun (Ser73) antibody kit (9260) purchased from Cell Signaling Technology (Ozyme, St Quentin Yvelines, France)). Bands were visualized using the ECL Western Blotting Detection Reagents Kit (Amersham Biosciences, Orsay, France). Blots were then dehybridized and rehybridized successively with a mouse anti ☐-tubulin (D-10) (sc-5274) primary antibody (dilution 1:400) and a HRP conjugated goat anti-mouse IgG secondary antibody (sc-3697) (dilution 1:5000) (both purchased from Santa Cruz Biotechnology (Tebu-bio, Le Perray en Yvelines Cedex, France)). The relative band intensity for phospho c-Jun (Ser 63 or Ser73) was calculated in comparison to that for ☐-tubulin after densitometry analysis (ImageJ software).

To analyze the ERK and p38 MAPK pathways, blots were sequentially incubated with a rabbit phospho-p44/42 MAPK (Erk1/2) (Thr202/Tyr204) (4370) primary antibody (or rabbit phospho-p38 MAPK (Thr180/Tyr182) (9215) antibody) and a horseradish peroxidase-conjugated goat anti-rabbit IgG (H+L) (PI-1000—Vector Laboratories, Cliniscences, Montrouge, France) secondary antibody at dilution 1:5000. Blots were then dehybridized and rehybridized successively with a rabbit p44/42 MAPK (Erk1/2) (4695) (or rabbit p38 MAP Kinase (9212) antibody) and the same secondary antibody as above. Primary antibodies were purchased from Cell Signaling Technology (Ozyme, St Quentin Yvelines, France) and all steps performed following the manufacturer's instruction.

Immunohistochemistry

To characterize the cellular infiltrate, sections were double-stained with ED1 and iNOS. Briefly, after permeabilization with 0.1% TritonX-100 in phosphate buffered saline (PBS) for 30 min, specimens were rinsed and saturated for 30 min with 5% skimmed milk in PBS. They were incubated overnight at 4° C. with the two following primary antibodies: a 1:50 mouse monoclonal anti-macrosialin CD68 (clone ED1), directed against a cytoplasmic antigen in rat monocytes, macrophages and dendritic cells (purchased from Serotec Ltd. (Oxford, UK)) and a polyclonal rabbit anti-iNOS (1/75e; Transduction Laboratories, Lexinton, FY). After washing, sections were incubated for 1 hour at room temperature with a secondary Alexa Fluor 594 (red)-conjugated donkey anti-mouse monoclonal antibody (mAb) and a secondary Alexa Fluor 488 (green)-conjugated goat anti-rabbit mAb each at dilution 1:250 (Invitrogen, Cergy Pontoise, France). For each step, antibodies were diluted in PBS-1% skimmed milk—0.1% TritonX100. Different controls were included in every staining run: negative controls without primary antibodies and isotype controls by incubation with normal mouse or rabbit serum immunoglobulin (Ig) in place of primary antibodies. After staining nuclei with DAPI (Sigma-Aldrich, Saint-Quentin Fallavier, France), sections were mounted in PBS/Glycerol (1/1) and observed by fluorescence photomicroscopy (FXA, Microphot, Nikon, Melville, USA). Digitized micrographs were obtained using a digital camera (Spot, BFI Optilas, Evry, France). ED1 positive cells and polymorphonuclear cells, identified by the shape of their nuclei stained with DAPI, were quantified on histological sections. The analysis was performed on 3 eyes per experimental group, with 2 different sections per eye at the optic nerve head level. Results were expressed as mean±standard error of the mean (SEM).

Immunostaining of the JNK-inhibitor (poly-)peptide of SEQ ID NO: 11 was performed on healthy and uveitic eyes to study its ocular biodistribution after systemic or local administration. Briefly, sections were permeabilized as described above before being sequentially incubated with an anti-SEQ ID NO: 11 purified rabbit IgG and a secondary Alexa 594 (red)-conjugated goat anti-rabbit IgG (Invitrogen, Cergy Pontoise, France) diluted 1:100 and 1:250 in PBS respectively. Immunostaining of untreated healthy and uveitic eyes were used as negative controls. Nuclei were stained with DAPI before mounting and observation.

Immunostaining of p-Erk1/2 was performed to evaluate the effect of the JNK-inhibitor (poly-) peptide of SEQ ID NO: 11 on the ERK pathway after IV or IVT administration. Sections were permeabilized as described above and incubated in blocking solution containing 0.1% Triton X-100 and 10% FCS (fetal calf serum) in PBS for 1 hour at room temperature. Sections were incubated overnight at 4° C. with a rabbit anti-phospho-p44/42 MAPK (Erk1/2) primary antibody (4370) purchased from Cell Signaling Technology (Ozyme, St Quentin Yvelines, France) diluted 1:400 in blocking solution. After having been rinsed three times in PBS, sections were incubated with a secondary Alexa Fluor 488 (green)-conjugated goat anti-rabbit mAb (diluted 1:300 in blocking solution) for 2 hours at room temperature. Nuclei were stained with DAPI before mounting and observation.

Evaluation of iNOS Expression in Ocular Tissues Using Semi-Quantitative PCR

Two eyes per group were used for this analysis. Immediately after dissection, retinas extracted from each eye were separately snap frozen and stored at −80° C. until use. Total RNA was extracted from tissues (RNeasy minikit, Qiagen, Courtaboeuf, France) according to the manufacturer's instructions. Reverse transcription was performed on 1 µg of total RNA in a total volume of 20 µL using Superscript II Reverse Transcriptase (Invitrogen, Cergy-Pontoise, France) following the manufacturer's instructions. To amplify GAPDH and iNOS cDNA, Polymerase-Chain Reaction (PCR) was conducted in a total volume of 25 µL containing 2 µL of first-strand reaction product, 0.4 µM forward and 0.4 µM reverse primers, 0.4 µM dNTP Mix, 1.5 mM MgCl2, 1×PCR buffer and 2.5 U Taq DNA polymerase (Invitrogen, Cergy Pontoise, France). Primers specific for GAPDH (Forward: 5'-ATGCCCCCATGTTTGTGATG-3' (SEQ ID NO:101); Reverse: 5'-ATGGCATGGACTGTGGTCAT-3' (SEQ ID NO:106)) and iNOS (Forward: 5'-TTTCTCTT-CAAAGTCAAATCCTACCA-3' (SEQ ID NO:107); Reverse: 5'-TGTGTCTGCAGATGTGCTGAAAC-3' (SEQ ID NO:108)) were obtained from Invitrogen. After an initial denaturation (3 min at 94° C.), 30 to 32 PCR cycles of denaturation (30 s, 94° C.), annealing (1 min, 58° C. (GAPDH) and 52° C. (iNOS)) and elongation (1 to 2 min, 72° C.) were performed on a Crocodile III (Appligene Oncor). The final cycle was completed by 5 min of elongation at 72° C. PCR fragments (162 bp for GAPDH and 657 bp for iNOS) were analyzed by 2.5% agarose gel electrophoresis and visualized by ethidium bromide staining under UV light. The relative band intensity for iNOS was calculated in comparison to that for GAPDH after densitometry analysis (ImageJ software).

Chemokine/Cytokine Multiplex Assay

Intraocular fluids (diluted to obtain a final volume of 25 µL) and sera (25 µL of 1:5 dilution) were subjected to multiplex bead analysis. This method uses microspheres as the solid support for immunoassays12 and allows the titration of a greater number of cytokines with increased sensitivity than occurs with ELISA.13 For each sample, seventeen analytes were quantified simultaneously using the rat Cytokine/Chemokine-17plex kit (Milliplex Map Kit, Millipore, Saint-Quentin-en-Yvelines, France) according to the manufacturer's instructions: Chemokines MCP-1/CCL2, MIP-1α/CCL3, RANTES/CCL5, IP-10/CXCL10 (IFN-inducible protein-10) and GRO/KC; proinflammatory mediators IL-1☐, IL-18 and TNF-☐; Th1/Th2/Th17 cytokines IL-2 and IFN-☐/IL-4, IL-5, IL-6, IL-10 and IL-13/IL-17. The assay was performed in a 96-well filter plate and standard curves for each cytokine were generated with a Rat Cytokine Standard provided in the kit. All incubation steps were performed under medium orbital agitation and in the dark to protect the beads from light. Data acquisition and analysis were performed with the manager software version 4.1 (Bioplex; Bio-Rad) with four or five logistic parameters for standard curves. Detection thresholds for all the analytes were estimated around 1 to 10 pg/mL.

Statistical Analysis

Numerical results were expressed as mean±standard error of the mean (SEM). Data were compared using the non-parametric Mann-Whitney U-test. P<0.05 was considered statistically significant.

Figure 1:
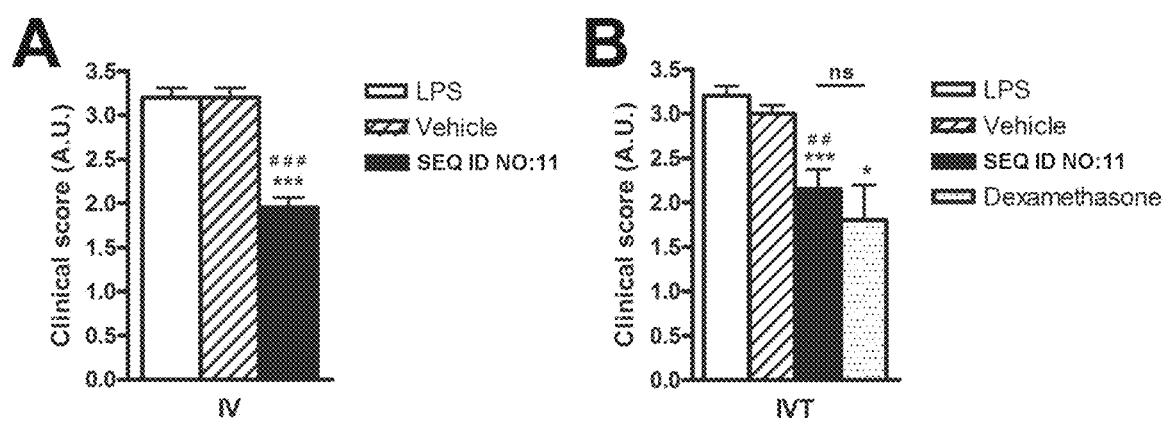
FIG. 1 Clinical efficacy of SEQ ID NO: 11 in LPS-induced uveitis: Clinical scores (expressed in arbitrary units, A.U.) were evaluated at the peak of the disease, 24 hours after (A) intravenous (IV) or (B) intravitreous (IVT) injection of JNK-inhibitor (poly-)peptide of SEQ ID NO: 11. Comparison was made with untreated uveitic eyes (LPS) and IV/IVT treatment with vehicle (n=10 eyes per group). Clinical manifestations of uveitis were reduced after (A) IV injection of JNK-inhibitor (poly-)peptide of SEQ ID NO: 11 (*$p<0.001$ vs LPS; ###$p<0.001$ vs Vehicle) and (B) IVT injection of (poly-)peptide of SEQ ID NO: 11 (*$p<0.001$ vs LPS; ##$p<0.01$ vs Vehicle) and dexamethasone (*** $p<0.05$ vs LPS). No statistical difference (ns) was observed between IVT injection of JNK-inhibitor (poly-)peptide of SEQ ID NO: 11 and dexamethasone that was used as positive control.

Results:

The all-D-retro-inverso JNK-inhibitor (poly-)peptide of SEQ ID NO: 11 significantly reduced endotoxins induced uveitis (EIU). The JNK-inhibitor (poly-)peptide of SEQ ID NO: 11 significantly reduced EIU clinical scores after 20 μg/kg intravenous (IV) injection (2.0±0.1) compared to untreated uveitic eyes (3.2±0.1, p<0.001) and vehicle IV (3.2±0.1, p<0.001) (FIG. 1A). In a similar manner, clinical scores were significantly decreased after 0.2 μg/injection intravitreous (IVT) administration of the JNK-inhibitor (poly-)peptide of SEQ ID NO: 11 (2.2±0.2) in comparison to untreated uveitic eyes (3.2±0.1, p<0.001) and vehicle IVT (3.0±0.1, p<0.01) (FIG. 1B). The effect of IVT injection of the JNK-inhibitor (poly-)peptide of SEQ ID NO: 11 on clinical signs of EIU was not statistically different from that observed after IVT of dexamethasone (1.8±0.4) suggesting that the JNK-inhibitor (poly-)peptide of SEQ ID NO: 11 was as efficient as dexamethasone in reducing EIU when administered at this time point (FIG. 1B).

Figure 2:
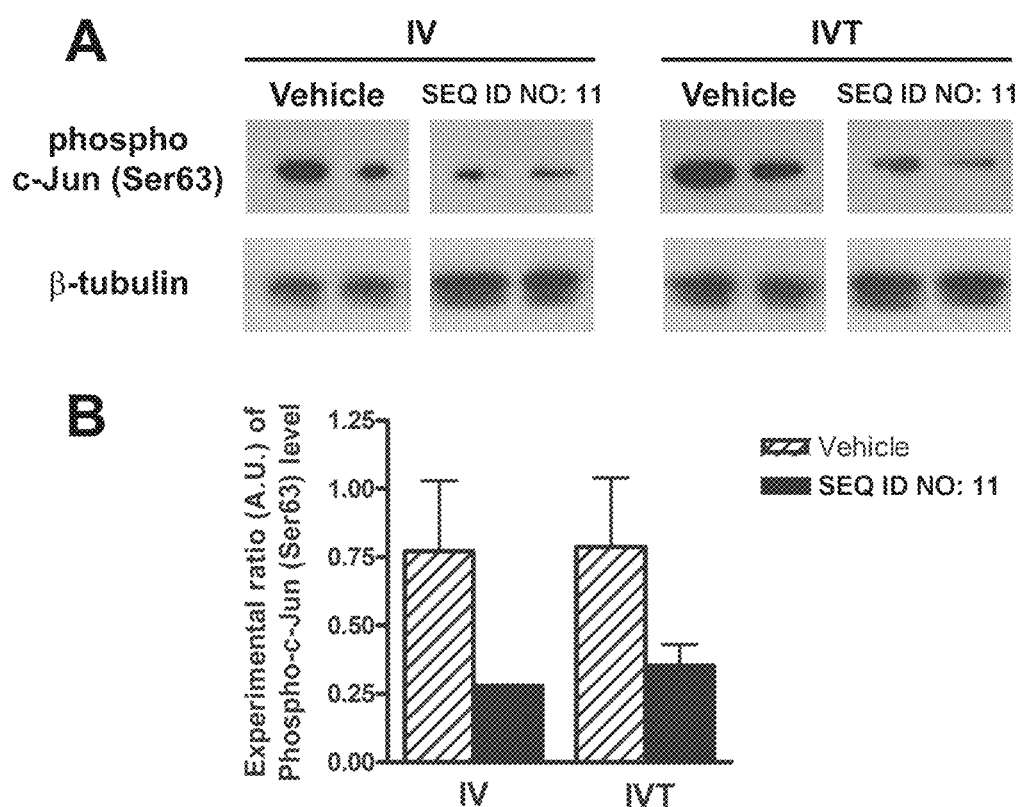
FIG. 2 Inhibition of the JNK pathway by SEQ ID NO: 11 in LPS-induced uveitis: Western-Blot analysis of c-Jun phosphorylation in RPE/choroid/sclera complexes 24 hours after IV or IVT injections of JNK-inhibitor (poly-)peptide of SEQ ID NO: if and vehicle (n=2 eyes per group) in Endotoxin-Induced Uveitis (EIU) conditions. Inhibition of c-Jun phosphorylation by JNK-inhibitor (poly-) peptide of SEQ ID NO: 11 was visualized on (A) immunoblot (upper lane: Phospho c-Jun (Ser63); bottom lane: I3-tubulin reporter protein; and confirmed by (B) densitometric quantitation.

Efficacy of the (Poly-)Peptide of SEQ ID NO: 11 Resulted from JNK Pathway Inhibition To determine whether the clinical effect of the JNK-inhibitor (poly-)peptide of SEQ ID NO: 11 was related to its mode of action, i.e. its ability to interfere with JNK signaling, 6 c-Jun phosphorylation state was analyzed in ocular tissues by Western-Blot. Phosphorylation of c-Jun on Ser63 (FIG. 2A) and Ser73 residues was reduced in RPE/choroid extracts 24 hours after the JNK-inhibitor (poly-)peptide of SEQ ID NO: 11 was injected intravenously or intravitreously. In the neuroretina, phospho c-Jun could only be faintly detected. An approximately 3-fold decrease in c-Jun phosphorylation was observed in RPE/choroid either after IV (0.28±0.01 vs 0.77±0.26 in IV of vehicle) or IVT (0.35±0.08 vs 0.79±0.25 in IVT of vehicle) administration of the JNK-inhibitor (poly-)peptide of SEQ ID NO: 11 (FIG. 2B). The ability of the JNK-inhibitor (poly-)peptide of SEQ ID NO: 11 to block c-Jun NH2-terminal kinases (JNK) activity in the eye tissues demonstrated the specific intraocular activity of the JNK-inhibitor (poly-)peptide of SEQ ID NO: 11.

Figure 3:
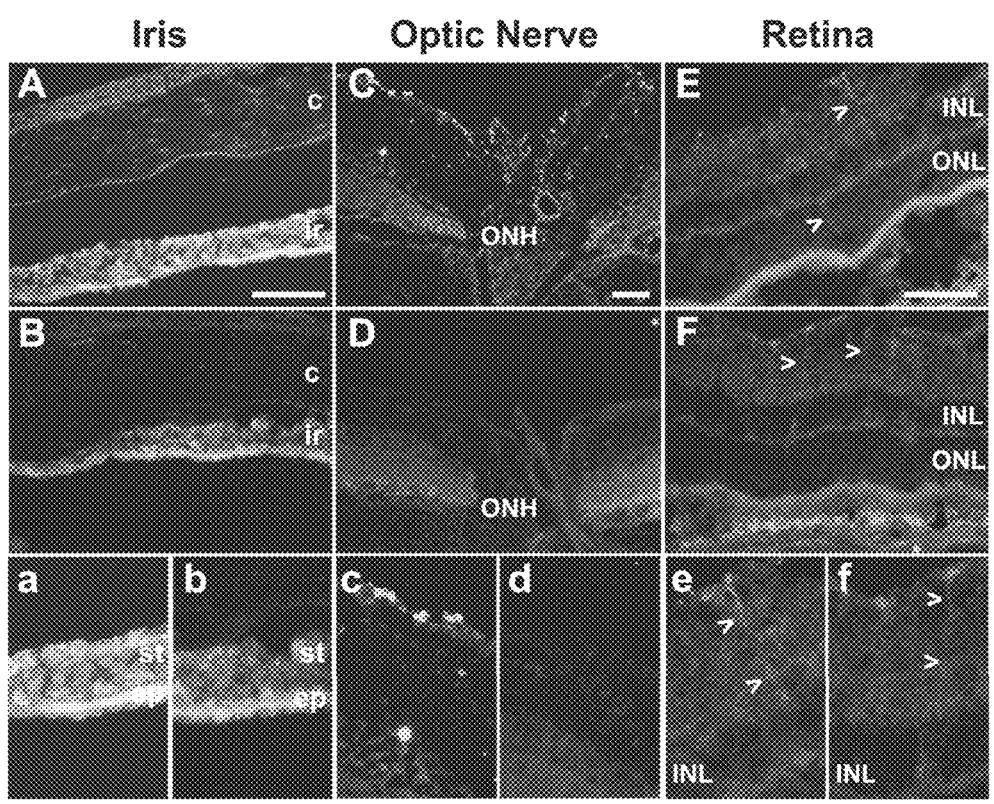
FIG. 3 Effects of SEQ ID NO: 11 on the LPS-ERK pathway activation: Immunohistochemistry against phospho-p44/42 MAPK (Erk1/2) (green) was carried out on ocular histological sections from untreated uveitic control eyes and IV or IVT injected animals (vehicle or SEQ ID NO: 11) (n=3 eyes analyzed per condition; time point: 24 h). Nuclei (in blue) were stained with DAPI. p-Erk1/2 was strongly expressed in the iris epithelium after IVT administration of vehicle (A, a) and SEQ ID NO: 11 (B, b), with no detectable difference between the two. Only a faint positive signal could be detected in retinal mutter glial cells in EIU eyes treated by IV injection of either the vehicle (E, e) or SEQ ID NO:11 (F, f) (see arrows). Scale bar: 100 μm. c: cornea; ir: iris; st: stroma; ep: epithelium; ONH: optic nerve head; INL: inner nuclear layer; ONL: outer nuclear layer.

To determine whether the JNK-inhibitor (poly-)peptide of SEQ ID NO: 11 could have any effect on the other MAPK pathways, the phosphorylation state of Erk1/2 and p38 was evaluated. Whereas Erk1/2 and p38 were detected in RPE/choroid complexes at similar levels among all groups, the phosphorylation form of these two MAPK could not be detected by western-blot analysis (data not shown). These results demonstrate that JNK is the predominantly activated MAPK pathway in RPE/choroid during EIU. Using histochemical analysis, performed without any signal amplification, we found an intense p-Erk1/2 signal in inflammatory cells infiltrating in the anterior and the posterior segments of the eye in the control LPS and saline treated eyes (FIGS. 3C, 3D). The effect of the JNK-inhibitor (poly-)peptide of SEQ ID NO: 11 either administered intravenously or intravitreously could not be evaluated on those cells, since the infiltration was almost absent in the treated eyes. However, in the neuroretina, where p-Erk1/2 could be detected and located in retinal Müller glial (RMG) cells in the control and saline treated eyes (FIG. 3E), no effect of the JNK-inhibitor (poly-)peptide of SEQ ID NO: 11 administered by either route was observed (FIG. 3F). Interestingly, in the iris, an intense p-Erk1/2 signal was observed in the epithelium of the control and saline injected eyes (FIG. 3A) with no effect of the JNK-inhibitor (poly-)peptide of SEQ ID NO: 11 treated on the p-Erk1/2 signal in these cells (FIG. 3B), strongly suggesting that the JNK-inhibitor (poly-)peptide of SEQ ID NO: 11 does not seem to directly act on p-Erk1/2 phosphorylation during EIU in our model, at least in resident cells.

Figure 4:
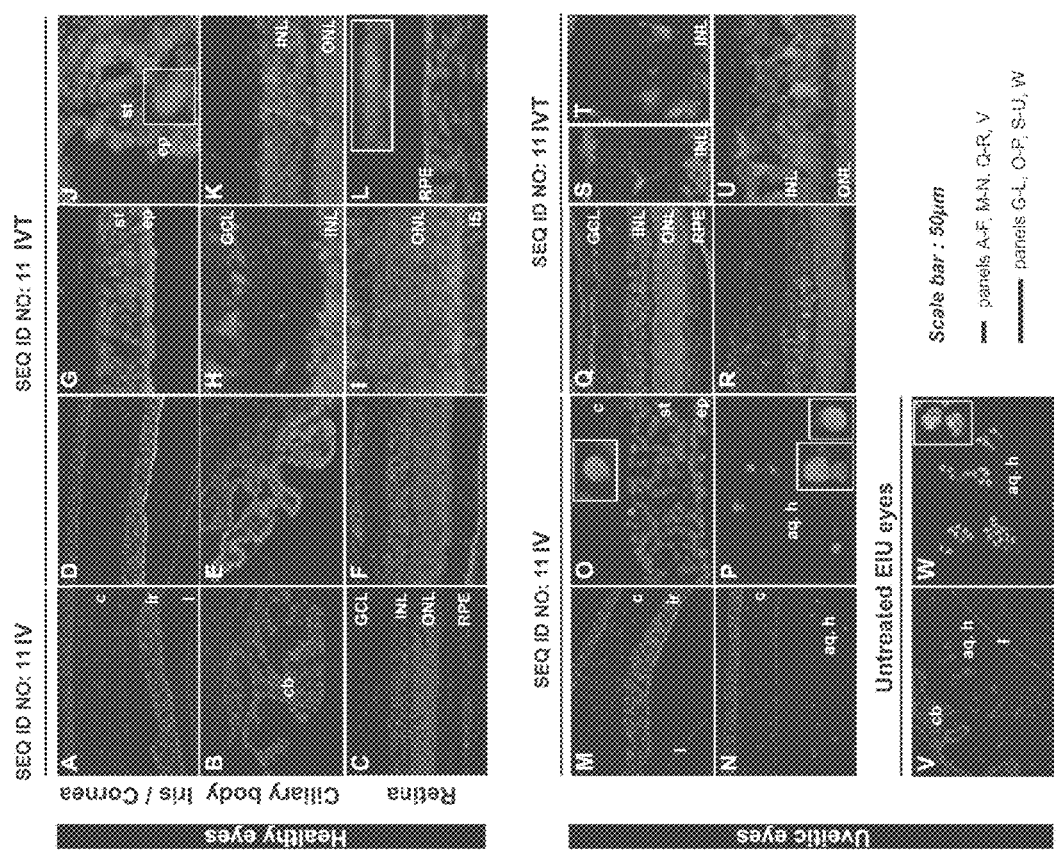
FIG. 4 Ocular biodistribution of JNK-inhibitor (poly-) peptide of SEQ ID NO: 11 in healthy and uveitic eyes.

Differential Distribution of the JNK-Inhibitor (Poly-)Peptide of SEQ ID NO: 11 in Ocular Tissues after IV and IVT Administrations Immunohistochemistry was carried out on histological sections to evaluate the biodistribution of the JNK-inhibitor (poly-)peptide of SEQ ID NO: 11 in ocular tissues 24 hours after systemic (IV) or local (IVT) administration, both in healthy eyes and in uveitic conditions (FIG. 4). No inflammatory cell infiltration was observed in healthy eyes either after IV or IVT of the JNK-inhibitor (poly-)peptide of SEQ ID NO: 11 or vehicle. No immunoreactivity against the JNK-inhibitor (poly-)peptide of SEQ ID NO: 11 was detected in untreated control eyes or in eyes treated by vehicle, demonstrating the specificity of the signal observed in the JNK-inhibitor (poly-)peptide of SEQ ID NO:11-treated eyes. Whereas no signal was observed in normal eyes after systemic (IV) injection (FIG. 4 A-C) at the dose used, the JNK-inhibitor (poly-)peptide of SEQ ID NO: 11 was distributed in almost all ocular tissues of normal rats after IVT administration (FIG. 4 D-L). Interestingly, an accumulation of the JNK-inhibitor (poly-) peptide of SEQ ID NO: 11 was detected mainly in the iris/ciliary body epithelium (panels G and J) and in the retinal pigment epithelium (panel L). Penetration of the JNK-inhibitor (poly-) peptide of SEQ ID NO: 11 was also detected in the iris stroma (panel G) as well as in the neural retina in the ganglion cell layer (GCL, panel H), the inner nuclear layer (INL, panel K) and the inner segment (IS, panel I) of photoreceptor cells (PR). In all cell types, the JNK-inhibitor (poly-) peptide of SEQ ID NO: 11 accumulated within the cytoplasm. Occasional staining was found in the corneal endothelium and in the lens capsule.

In uveitic conditions, no the JNK-inhibitor (poly-)peptide of SEQ ID NO: 11 staining was detected in ocular tissues and in infiltrating inflammatory cells of untreated eyes (FIG. 4, panels V-W). IV or IVT of vehicle gave similar results to those from untreated eyes. In EIU eyes treated by IV injection of the JNK-inhibitor (poly-)peptide of SEQ ID NO: 11, it was not detected in ocular tissues, but occasional infiltrating inflammatory cells were immunopositive in the iris (panel O) and in the aqueous humor (panel P). In uveitic eyes treated by IVT injection, the JNK-inhibitor (poly-) peptide of SEQ ID NO: 11 was mostly found in ocular tissues like in healthy eyes and in resident cells that are mobilized and participate actively to the inflammatory processes in pathological conditions such as microglial cells (panels S-T).

A Significant Reduction in Cells Infiltrating the Ocular Tissues Resulted from the JNK-Inhibitor (Poly-)Peptide of SEQ ID NO: 11 Administration To further characterize the effect of the JNK-inhibitor (poly-)peptide of SEQ ID NO: 11 in uveitis, the infiltrated inflammatory cells were quantified in ocular tissues (FIG. 5) by numeration on histological sections immunostained with ED1 and iNOS antibodies (FIG. 6). 24 hours after LPS challenge, the number of ED1 positive cells was significantly reduced in eyes treated with IV injection of the JNK-inhibitor (poly-)peptide of SEQ ID NO: 11 (137±7) (FIG. 5A, FIG. 6M, P, S) as compared to untreated uveitic eyes (LPS) (187±13, $p<0.005$) (FIG. 5A, FIG. 6A, D, G, J) or vehicle injected eyes. Similarly, IVT of the JNK-inhibitor (poly-) peptide of SEQ ID NO: 11 significantly reduced ED1 positive infiltrating cells (93±8) as compared to vehicle IVT injected eyes (175±15, $p<0.009$) and untreated uveitic eyes ($p<0.005$) (FIG. 5A). The reducing effect of the JNK-inhibitor (poly-)peptide of SEQ ID NO: 11 on ED positive cell infiltration (93±8) did not differ from that induced by dexamethasone (79±15), suggesting that both treatments have a similar efficacy on this parameter.

The number of polymorphonuclear cells (PMN) (FIG. 5B) was also significantly reduced at 24 hours after IV administration of the JNK-inhibitor (poly-)peptide of SEQ ID NO: 11 (60±6) as compared to control eyes (237±15, $p<0.005$), and after IVT injection of the JNK-inhibitor (poly-)peptide of SEQ ID NO: 11 (40±5) as compared to IVT injection of the vehicle (152±31, $p<0.009$) and control uveitic eyes ($p<0.005$). Again, the effect of the JNK-inhibitor (poly-)peptide of SEQ ID NO: 11 on PMN ocular tissue infiltration did not significantly differ from that of dexamethasone (42±11).

The JNK-inhibitor (poly-)peptide of SEQ ID NO: 11 down regulates iNOS expression Since iNOS (inducible nitric oxide synthase) has been described as a key mediator in the pathogenesis of uveitis,14,15 the effect of the JNK-inhibitor (poly-)peptide of SEQ ID NO: 11 on its expression was investigated at both the protein and mRNA levels.

As shown on FIG. 6, the number of iNOS positive cells was reduced in eyes treated with injection of the JNK-inhibitor (poly-)peptide of SEQ ID NO: 11 IV (FIG. 6N, Q, T) or IVT compared to control eyes (panels B E, H, K). Among iNOS positive cells observed in control eyes, a few number were ED1+ cells while most of them were ED1- suggesting that mostly PMNs produced iNOS (insets c, f, i). In eyes from the JNK-inhibitor-treated rats, the only cells still expressing iNOS were intra tissular ED1 positive cells located at the ciliary body root (inset r2).

The effect of the JNK-inhibitor (poly-)peptide of SEQ ID NO: 11 on iNOS expression was confirmed by RT-PCR on ocular tissues (FIG. 7). Levels of iNOS mRNA were downregulated from 1.02±0.21 to 0.40±0.11 after IV of the JNK-inhibitor (poly-)peptide of SEQ ID NO: 11 and from 1.18±0.05 to 0.27±0.09 in eyes treated by IVT injection. Comparisons were made with IV or IVT of vehicle respectively.

Chemokine/Cytokine Profiles in Ocular Media of Eyes Treated with the JNK-Inhibitor (Poly-)Peptide of SEQ ID NO: 11

To evaluate the effect of the treatment on the production of pro- and anti-inflammatory mediators, chemokines and cytokines were dosed by multiplex analysis on ocular media (FIGS. 8 and 9) and sera.

Among the 17 chemokines/cytokines tested, some were below detectable levels both in control or treated eyes: IP-10, IL-5, IL-17. Other did not differ in treated versus untreated eyes at any of the tested time points: IL-18, IL-4, IL-1β. In the serum, while some cytokines tended to change after IV administration of the JNK-inhibitor (poly-)peptide of SEQ ID NO: 11 (reduction of MIP-1α and IL-2) or after IVT (reduction of IL-2), this was not statistically significant. For the other chemokines/cytokines, their profile was different in ocular fluids from eyes treated with IV administration of the JNK-inhibitor (poly-)peptide of SEQ ID NO: 11 as compared to the IVT administration. Indeed, when the JNK-inhibitor (poly-)peptide of SEQ ID NO: 11 was injected systemically at the time of LPS challenge, it induced a significant reduction of MCP-1, MIP-1α and RANTES at 6 and 24 hours (FIG. 8A). GRO/KC was also significantly reduced at 6 hours. Th1 cytokines such as TNF-α, IL-6 and INF-γ were significantly reduced at different time points while IL-10 tended to increase at 6 hours in treated eye (but not significantly), suggesting a switch towards a Th2 profile (FIG. 8B). No statistical differences were noticed between eyes from vehicle IV injected rats and untreated uveitic control eyes.

When the JNK-inhibitor (poly-)peptide of SEQ ID NO: 11 was injected into the vitreous at the time of LPS challenge, the chemokine/cytokine profiles was not strikingly different from that of eyes injected with vehicle (FIGS. 9A and 9B). It is interesting to note though that IVT of vehicle had a marked effect on the cytokine profile as compared to untreated uveitic control eyes. At 6 hours, a trend to a decrease of MCP-1, TNF-α, IL-6, IL-2 and at 24 hours, a marked decrease of IL-2 and an increase of IL-13 were detected suggesting again a switch towards a Th2 profile.

The invention claimed is:

1. A method for treating a chronic or non-chronic inflammatory eye disease in a subject in need thereof, the method comprising administering a JNK inhibitor (poly-) peptide comprising less than 150 amino acids in length to the subject, wherein the chronic or non-chronic inflammatory eye disease is selected from the group consisting of posterior uveitis, an inflammatory eye disease of the blephera, an inflammatory eye disease of the conjunctiva, an an inflammatory eye disease of the sclera, an inflammatory eye disease of the vitreous body, and an inflammatory eye disease of the orbital bone.

2. The method of claim 1, wherein the JNK inhibitor (poly-)peptide comprises SEQ ID NO: 11.

* * * * *